United States Patent
Zhang et al.

(10) Patent No.: US 12,390,446 B2
(45) Date of Patent: Aug. 19, 2025

(54) PROLINE-BASED NEUROPEPTIDE FF RECEPTOR MODULATORS

(71) Applicant: RESEARCH TRIANGLE INSTITUTE, Research Triangle Park, NC (US)

(72) Inventors: Yanan Zhang, Apex, NC (US); Thuy Nguyen, Morrisville, NC (US)

(73) Assignee: RESEARCH TRIANGLE INSTITUTE, Research Triangle Park, NC (US)

(*) Notice: Subject to any disclaimer, the term of this patent is extended or adjusted under 35 U.S.C. 154(b) by 0 days.

(21) Appl. No.: 18/484,116

(22) Filed: Oct. 10, 2023

(65) Prior Publication Data
US 2024/0058303 A1    Feb. 22, 2024

Related U.S. Application Data

(62) Division of application No. 17/937,450, filed on Oct. 2, 2022, now Pat. No. 11,826,350, which is a division of application No. 16/485,570, filed as application No. PCT/US2018/018074 on Feb. 13, 2018, now Pat. No. 11,491,136.

(60) Provisional application No. 62/458,731, filed on Feb. 14, 2017.

(51) Int. Cl.
A61K 31/40    (2006.01)
A61P 25/00    (2006.01)

(52) U.S. Cl.
CPC .............. *A61K 31/40* (2013.01); *A61P 25/00* (2018.01)

(58) Field of Classification Search
CPC ........ A61K 31/40; A61K 31/401; A61P 25/00; A61P 25/04; A61P 25/36
See application file for complete search history.

(56) References Cited

U.S. PATENT DOCUMENTS

| | | |
|---|---|---|
| 5,962,514 A | 10/1999 | Evenden et al. |
| 7,544,691 B2 | 6/2009 | Breu et al. |
| 11,491,136 B2 | 11/2022 | Zhang et al. |
| 2006/0116515 A1 | 6/2006 | Gahman et al. |
| 2006/0194788 A1 | 8/2006 | Caroff et al. |
| 2013/0296271 A1 | 11/2013 | Sakai et al. |

(Continued)

FOREIGN PATENT DOCUMENTS

| | | |
|---|---|---|
| EP | 2716291 A1 | 4/2014 |
| JP | 2006520330 A | 9/2006 |
| WO | WO03026667 A1 | 4/2003 |

(Continued)

OTHER PUBLICATIONS

Lameh et al (JPET, 2010; 334:244-254) (Year: 2010).*

(Continued)

*Primary Examiner* — Rayna Rodriguez
(74) *Attorney, Agent, or Firm* — HULTQUIST, PLLC; Steven J. Hultquist

(57) ABSTRACT

Neuropeptide FF receptor modulators based on a proline scaffold are provided which offer NPFF receptor potencies in the nanomolar range and antagonistic selectivity for the NPFF1 receptor. Methods, compounds and compositions for modulating the function of neuropeptide FF receptors are provided for pharmacotherapies capable of influencing conditions or disorders affected by the neuropeptide FF receptors.

8 Claims, 6 Drawing Sheets

(56) References Cited

U.S. PATENT DOCUMENTS

2023/0091922 A1     3/2023     Zhang et al.

FOREIGN PATENT DOCUMENTS

| WO | WO2004080965 A1 | 9/2004 |
| WO | WO2005023781 A1 | 3/2005 |
| WO | WO2005031000 A2 | 4/2005 |
| WO | 2007039123 A2 | 4/2007 |
| WO | WO2008148689 A1 | 12/2008 |
| WO | WO2009038012 A1 | 3/2009 |
| WO | 2016020892 A1 | 2/2016 |
| WO | WO2016097869 A1 | 6/2016 |

OTHER PUBLICATIONS

Mankus et al (Future Med Chem, 2012; 4(9):1085-1092) (Year: 2012).*

Nguyen et al (J Med Chem, 2020; 63:12387-12402) (Year: 2020).*

Bihel, F., et al., "Development of a Peptidomimetic Antagonist of Neuropeptide FF Receptors for the Prevention of Opioid-Induced Hyperalgesia", ACS Chemical Neuroscience, 2015, A-H.

Bonini, J., et al., "Identification and Characterization of Two G Protein-Coupled Receptors for Neuropeptide FF", The Journal of Biological Chemistry, 2000, pp. 39324-39331, vol. 275, No. 50.

CAS Registry No. 107638-85-7, Apr. 18, 1987.

Chen, J., et al., "Neuropeptide FF Potentiates the Behavioral Sensitization to Amphetamine and Alters the Levels of Neurotransmitters in the Medial Prefrontal Cortex", Brain Research, 1999, pp. 220-224, vol. 816.

Chong, C.M., et al., "Discovery of a Novel ROCK2 Inhibitor With Anti-Migration Effects via Docking and High-Content Drug Screening", Molecular BioSystems, 2016, pp. 2713-2721, vol. 12, No. 9.

Doan, K.M., et al., "Blood-Brain Barrier Transport Studies of Organic Ganidino Cations Using an in situ Brain Perfusion Technique", Brain Research, 2000, pp. 141-147, vol. 876.

Elhabazi, K., et al., "Involvement of Neuropeptides FF Receptors in Neuroadaptive Responses to Acute and Chronic Opiate Treatments", British Journal of Pharmacology, 2012, pp. 424-435, vol. 165.

Elphick, M.R., et al., "The Evolution and Variety of RFamide-type Neuropeptides: Insights from Deuterostomian Invertebrates", Frontiers in Endocrinology, Jun. 19, 2014, pp. 1-11, vol. 5.

Fukusumi, S., et al., "Recent Advances in Mammalian RFamide Peptides: The Discovery and Functional Analyses of PrRP, RFRPs and QRFP", Peptides, 2006, pp. 1073-1086, vol. 27.

Gaubert, G., et al., "Discovery of Selective Nonpeptidergic Neuropeptide FF2 Receptor Agonists", J. Med. Chem., 2009, pp. 6511-6514, vol. 52.

Gealageas, R., et al., "Development of Sub-Nanomolar Dipeptide Ligands of Neuropeptide FF Receptors", Bioorganic and Medicinal Chemistry Letters, 2012, pp. 7471-7474, vol. 22.

German, N., et al., "Diarylureas as Allosteric Modulators of the Cannabinoid CB1 Receptor: Structure-Activity Relationship Studies on 1-(4-Chlorophenyl)-3-{3-[6-(Pyrrolidin-1-yl) Pyridin-2-yl] Phenyl}Urea (PSNCBAM-1)", Journal of Medicinal Chemistry, 2014, pp. 7758-7769, vol. 57.

Gouarderes, "Functional Differences Between NPFF1 and NPFF2 Receptor Coupling: High Intrinsic Activities of RFAMIDE-Related Peptides on Stimulation of [35S]GTPyS Binding", Neuropharmacology, 2007, pp. 376-386, vol. 52.

English Translation of Examination Report in Japanese Patent Application No. 2022-040355 on Mar. 22, 2023.

Kotlinska, J., et al., "Neuropeptide FF (NPFF) Reduces the Expression of Cocaine-Induced Conditioned Place Preference and Cocaine-Induced Sensitization in Animals", Peptides, 2008, pp. 933-939, vol. 29.

Lameh, J., et al., "Neuropeptide FF Receptors Have Opposing Modulatory Effects on Nociception", The Journal of Pharmacology and Experimental Therapeutics, 2010, pp. 244-254, vol. 334, No. 1.

Liu, Q., et al., "Identification and Characterization of Novel Mammalian Neuropeptide FF-like Peptides That Attenuate Morphine-Induced Antinociception", The Journal of Biological Chemistry, Oct. 5, 2001, pp. 36961-36969, vol. 276, No. 40.

Malin, D.H., et al., "Nicotine Abstinence Syndrome Precipitated by an Analog of Neuropeptide FF", Pharmacology Biochemistry and Behavior, 1996, pp. 581-585, vol. 54, No. 3.

Marchand, S., et al., "A Neuropeptide FF Agonist Blocks the Acquisition of Conditioned Place Preference to Morphine in C57B1/6J Mice", Peptides, 2006, pp. 964-972, vol. 27.

Mishra, R.K., et al., "In Silico Modeling-Based Identification of Glucose Transporter 4 (GLUT4)-Selective Inhibitors for Cancer Therapy", The Journal of Biological Chemistry, 2015, pp. 14441-14453, vol. 290, No. 23.

Mouledous, L., et al., "Opioid-Modulating Properties of the Neuropeptide FF System", BioFactors, 2010, pp. 423-429.

Nguyen, T., et al., "Structure-Activity Relationships of Substituted 1H-Indole-2-Carboxamides as CB1 Receptor Allosteric Modulators", Bioorg Med Chem., May 1, 2015, pp. 2195-2203, vol. 23, No. 9.

Nguyen, T., et al., "Discovery of Novel Proline-Based Neuropeptide FF Receptor Antagonists", Neuroscience, 2017, pp. 2290-2308, vol. 8.

Quintanar-Audelo, M., et al., "Design and Synthesis of Indole-Based Peptoids as Potent Noncompetitive Antagonists of Transient Receptor Potential Vanilloid 1", J. Med. Chem., 2007, pp. 6133-6143, vol. 50.

Sandvik, G.K., et al., "RFamide Peptides in Early Vertebrate Development", Frontiers in Endocrinology, Dec. 4, 2014, pp. 1-18, vol. 5.

Simonin, F., et al., "RF9, a Potent and Selective Neuropeptide FF Receptor Antagonist, Prevents Opioid-Induced Tolerance Associated With Hyperalgesia", PNAS, Jan. 10, 2006, pp. 466-471, vol. 103, No. 2.

Simonin, F., et al., "RF9, A Potent and Selective Neuropeptide FF Receptor Antagonist, Prevents Opioid-Induced Tolerance Associated with Hyperalgesia—Correction", PNAS, Oct. 24, 2006, pp. 16057-16058, vol. 103, No. 43.

Vyas, N., et al., "Structure-Activity Relationships of Neuropeptide FF and Related Peptidic and Non-Peptidic Derivatives", Peptides, 2006, pp. 990-996, vol. 27.

Wang, Q., et al., "Evaluation of the MDR-MDCK Cell Line as a Permeability Screen for the Blood-Brain Barrier", International Journal of Pharmaceutics, 2005, pp. 349-359, vol. 288.

Warszycki, D., et al., "From Homology Models to a Set of Predicting Binding Pockets—a 5-HT1A Receptor Case Study", Journal of Chemical Information and Modeling, Feb. 27, 2017, pp. 311-321, vol. 57, No. 2.

Williams, et al., "Foye's Principles of Medicinal Chemistry", 2002, pp. 37-67, vol. 5th edition.

Wu, C.H., et al., "Distribution of Neuropeptide FF (NPFF) Receptors in Correlation With Morphine-Induced Reward in the Rat Brain", Peptides, 2010, pp. 1374-1382, vol. 31.

Xu, Z., et al., "Utilization of Halogen Bond in Lead Optimization: A Case Study of Rational Design of Potent Phosphodiesterase Type 5 (PDE5) Inhibitors", Journal of Medicinal Chemistry, 2011, pp. 5607-5611, vol. 54, Publisher: ACS Publications.

Yang, H., et al., "Isolation Sequencing, Synthesis, and Pharmacological Characterization of Two Brain Neuropeptides That Modulate the Action of Morphine", Proc. Natl. Acad. Sci., Nov. 1985, pp. 775-7761, vol. 82.

Yang, H., et al., "Modulatory Role of Neuropeptide FF System in Nociception and Opiate Analgesia", Neuropeptides, 2008, pp. 1-18, vol. 42.

Yang, H., et al., "Modulatory Roles of the NPFF System in Pain Mechanisms at the Spinal Level", Peptides, 2006, pp. 943-952, vol. 27.

Zhang, Y., et al., "Synthesis and Biological Evaluation of Bivalent Ligands for the CB1 Receptor", J. Med. Chem., 2010, pp. 7048-7060, vol. 53, No. 19.

* cited by examiner

Compound 1

Ke NPFF1 : 1620 ± 379 nM
Ke NPFF2 : 7251 ± 1734 nM

A

B

A

B

A

B

PROLINE-BASED NEUROPEPTIDE FF RECEPTOR MODULATORS

CROSS-REFERENCE TO RELATED APPLICATIONS

This is a divisional under 35 USC § 120 of U.S. patent application Ser. No. 17/937,450 filed Oct. 2, 2022 in the names of Yanan Zhang and Thuy Nguyen for "PROLINE-BASED NEUROPEPTIDE FF RECEPTOR MODULATORS", which in turn is a divisional under 35 USC § 120 of U.S. patent application Ser. No. 16/485,570 filed Aug. 13, 2019 in the names of Yanan Zhang and Thuy Nguyen for "PROLINE-BASED NEUROPEPTIDE FF RECEPTOR MODULATORS", which in turn is a U.S. national phase under 35 USC § 371 of International Patent Application No. PCT/US18/18074 filed Feb. 13, 2018 in the names of Yanan Zhang and Thuy Nguyen for "PROLINE-BASED NEUROPEPTIDE FF RECEPTOR MODULATORS", which in turn claims the benefit under 35 USC § 119 of U.S. Provisional Patent Application No. 62/458,731 filed Feb. 14, 2017 in the names of Yanan Zhang and Thuy Nguyen for "PROLINE-BASED NEUROPEPTIDE FF RECEPTOR MODULATORS". The disclosures of all such applications are hereby incorporated herein by reference, in their respective entireties, for all purposes.

FIELD

The present disclosure relates to proline-based compounds specific for neuropeptide FF (NPFF) receptors. The present disclosure further relates to methods, compounds and compositions for modulating the function of neuropeptide FF receptors to provide pharmacotherapies capable of influencing conditions or disorders affected by the neuropeptide FF receptors.

DESCRIPTION OF THE RELATED ART

Neuropeptide FF (NPFF) belongs to a family of neuropeptides called RFamide peptides, members of which all contain an Arg-Phe-NH$_2$ (RF-amide) motif at their C terminus. Neuropeptide FF is an endogenous peptide that binds to and activates two G protein-coupled receptors (GPCR), NPFF1 (GPR147) and NPFF2 (GPR74). These receptors are members of the rhodopsin family and predominantly couple to the G$\alpha_{i/o}$ proteins. Originally isolated from bovine brain, NPFF and its receptors have been identified in the central nervous system (CNS) of various animal species. Ligand binding studies performed on rodents confirmed that both receptor subtypes are widely expressed in the brain, whereas only NPFF2 receptors are expressed in the spine at detectable levels. The NPFF system has been implicated in the regulation of a variety of physiological processes, such as insulin release, food intake, memory, blood pressure, electrolyte balance, and neural regeneration. The NPFF system has also been shown to play an important role in modulating the effects of opioids and several other classes of drugs of abuse.

It is well documented that NPFF, having no affinity for the opioid receptors, is a modulator of opioid receptor function and attenuates the tolerance and dependence to opioids. Several studies have shown that the effects of NPFF on opioid modulation are dependent on the route of administration. For example, intracerebroventricular (i.c.v.) administration of NPFF in rats attenuated morphine-induced analgesia and locomotion, and precipitated opioid withdrawal syndromes in morphine-dependent rats, whereas intrathecal (i.t.) administration produced opioid-induced analgesia and also prolonged morphine-induced analgesia (Malin et al., *Peptides*, 11, 277-280 (1990); Yang et al., *Proc Natl Acad Sci USA*, 82, 7757-61, 1985; Gouarderes et al., Eur. J. Pharmacol., 237, 73-81 (1993)). Injection (i.c.v.) of 1Dme, a peptidic NPFF analog, inhibited morphine induced analgesia as well as the acquisition of place conditioning by morphine (Marchand et al., *Peptides*, 27, 964-72, 2006). Ventricular injection of NPFF antiserum restored the analgesic response to morphine in morphine-tolerant rats but did not affect opiate-naïve rats (Lake et al., *Neurosci. Lett.*, 132(1):29-32, 1991). RF9, a dipeptide NPFF1/2 receptor antagonist, dose-dependently blocked the long-lasting hyperalgesia produced by either acute fentanyl or chronic morphine administration (Elhabazi et al., *Br. J. Pharmacol.*, 165, 424-435, 2012; Simonin et al., *Proc. Natd. Acad. Sci. USA*, 103, 466-471, 2006). This effect appears to be mainly mediated by the NPFF1 receptor, as the selective NPFF1 antagonist AC-262620 also reduced opioid tolerance (Lameh et al., *J. Phamacol. Exp. Ther.*, 334, 244-254, 2010).

Opioids remain the most effective analgesics for many pain conditions, particularly for chronic pain; however, the adverse effects related to opioid use such as physical dependence, hyperalgesia and tolerance preclude adequate dosing and effective pain control in a large population of pain sufferers. Combination therapy which combines opioids with other drugs that may increase the efficacy of opioids and/or reduce the untoward effects offers a promising alternative strategy for pain management.

In view of the biological activity believed to be modulated by NPFF, the art is seeking compounds and compositions which provide inhibition or activation of the functional effects of NPFF.

SUMMARY

The present disclosure relates to neuropeptide FF and the discovery of proline-based neuropeptide FF receptor modulators. In one aspect, the disclosure relates to such proline-based neuropeptide FF receptor modulators according to Formula (I):

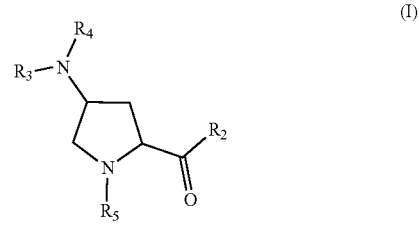

wherein R$_2$ is selected from —N—(C$_2$-C$_8$alkyl)$_2$ and NH—R$_1$, wherein R$_1$ is selected from C$_2$-C$_9$ alkyl, heterocyclealkyl, cycloalkylalkyl, aminoalkyl, and arylalkyl; R$_3$ is selected from C$_3$-C$_9$ alkyl, aryl, heteroaryl, heterocycle, heteroarylalkyl, heterocyclealkyl, and arylalkyl; R$_4$ is selected from H and C$_1$-C$_2$ alkyl; and R$_5$ is selected from C$_3$-C$_9$ alkyl, heteroarylalkyl, heteroaryl, heterocyclealkyl, heterocycle, cycloalkylalkyl, and arylalkyl. Proline-based neuropeptide FF receptor modulators according to Formulas II, IIA, III and IV are also provided.

In another aspect, the disclosure relates to a pharmaceutical composition comprising a proline-based neuropeptide FF receptor modulator represented by Formulas I, II, IIA, III or IV or a pharmaceutically acceptable salt thereof and a pharmaceutically acceptable carrier.

In a further aspect, the disclosure relates to a method for treating a subject having or susceptible to a condition or disorder where modulation of neuropeptide FF receptor activity is of therapeutic benefit, comprising administering to said subject having or susceptible to said condition or disorder a therapeutically effective amount of a compound according to Formulas I, II, IIA, III or IV or a pharmaceutically acceptable salt thereof.

Other aspects, features and embodiments of the disclosure will be more fully apparent from the ensuing description and appended claims.

DETAILED DESCRIPTION

The present disclosure relates to proline-based neuropeptide FF receptor modulators. The modulators exhibit affinity for and activity at the neuropeptide FF receptors. The molecules may thus be useful in the treatment of disorders, syndromes and conditions mediated by modulation of the neuropeptide FF receptors.

Research has found that NPFF precipitates a nicotine withdrawal syndrome, also suggesting that NPFF participates in the processes of dependence and drug addiction. (Malin et al., *Pharmacol. Biochem. Behav.*, 54, 581-585, 1996) It has further been shown that chronic administration of NPFF into the lateral ventricle potentiated the behavioral sensitization to amphetamine. (Chen et al., *Brain Res.*, 816, 220-224, 1999) More recently, it was demonstrated that stimulation of NPFF receptors decreased the expression of amphetamine-induced condition-placed preference, while the inhibition of NPFF receptors decreased amphetamine withdrawal anxiety. (Kotlinska et al., *Peptides*, 33, 156-163, 2012) Moreover, it has been suggested that NPFF is involved in the mechanism of expression of sensitization to cocaine hyperlocomotion, although this effect could be non-specific. (Kotlinska et al., *Peptides*, 29, 933-939, 2008) Consistent with these observations, there appears to be evidence that NPFF binding sites are abundant in the ventral tegmental area (VTA), while NPFF-like immunoreactivity was detected in the nucleus accumbens (NAc), two brain regions belonging to the mesolimbic dopamine (DA) projections which are known to be involved in drug addiction. (Wu et al., *Peptides*, 31, 1374-1382, 2010) Together, these findings make the NPFF system appear to be a viable target for the treatment of drug addiction.

Figure 1:
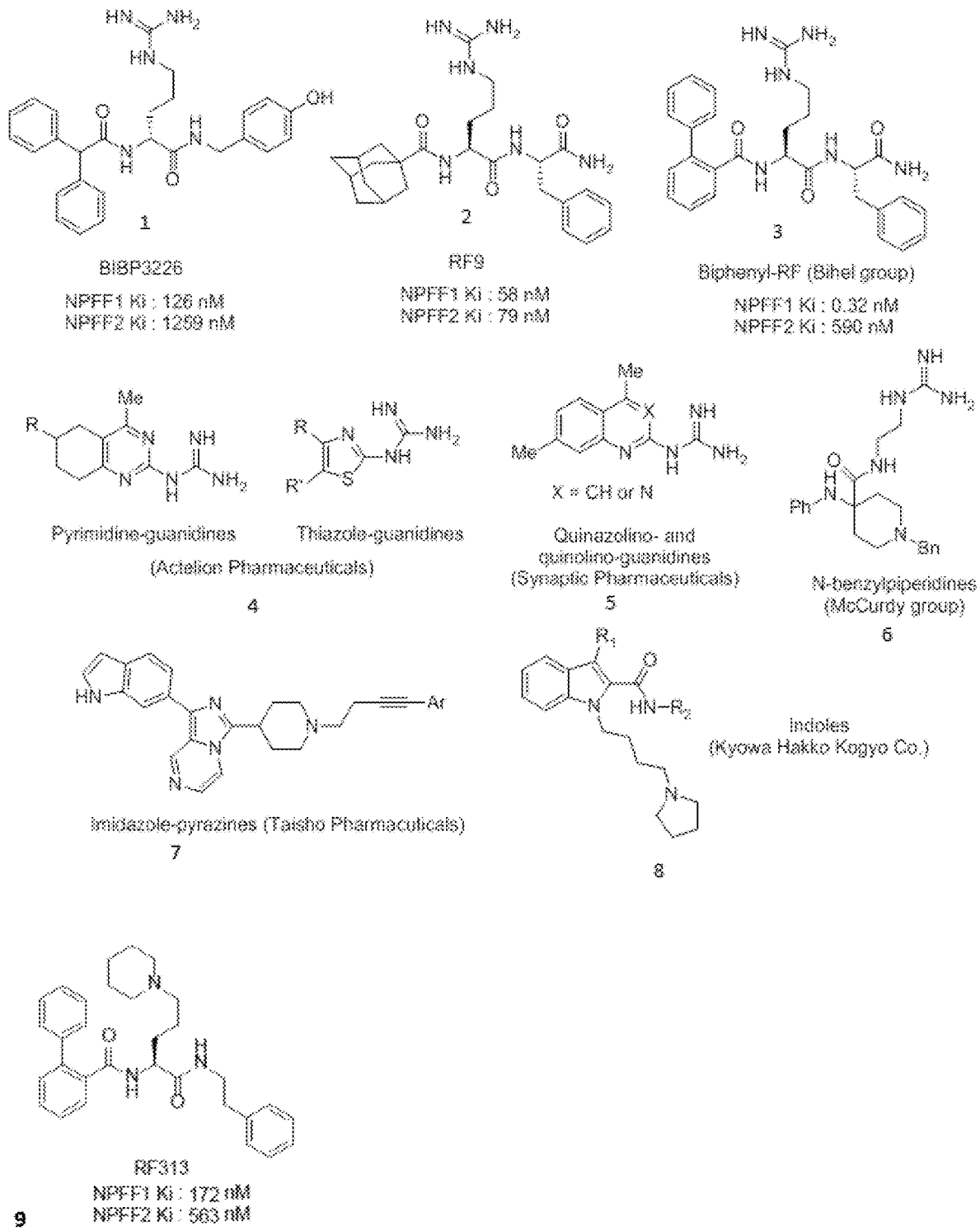
FIG. 1 depicts the chemical structures of various NPFF ligands described in the art.

In addition to NPFF, several other neuropeptides from the RFamide family have been found to activate one or both NPFF receptors, including NPSF (neuropeptide SF), NPAF (neuropeptide AF) and NPVF (neuropeptide VF). A number of peptidomimetic NPFF ligands have been reported, which include the guanidine functional group (FIG. 1). In these ligands, acylation of the last two amino acid residues (RF) have been reported to be critical for NPFF activities (BIBP3226 (Bonini et al., *J. Biol. Chem.* 275(50):39324-39331 (2000), chemical structure 1, FIG. 1) and RF9 (Simonin et al., *PNAS* 103(2): 466-471 (2006), chemical structure 2, FIG. 1). Modification of RF9 led to the NPFF1 selective dipeptide biphenyl-RF and peptidomimetic RF313 (Bihel et al., *ACS Chem Neurosci.*, 6(3): 438-445 (2015), chemical structure 3, FIG. 1; Gealageas, et al., *Bioorg. Med. Chem. Lett.* 22, 7471-7474 (2012); Elhabazi, et al., *Neuropharmacol.*, 118, 188-198 (2017)). These peptides or peptidomimetics were found to be effective in preventing fentanyl-induced hyperalgesia in rats by subcutaneous or oral administration, acting as antagonists.

Several classes of non-peptide NPFF ligands have also been disclosed. Quinazolino-, pyrimidine-, thiazole- and quinolino-guanidines were reported as NPFF ligands (WO 03/026667, chemical structure 5, FIG. 1; U.S. Pat. No. 7,544,691, chemical structures 4, FIG. 1). A series of N-benzylpiperidines were found to have mixed activities as agonists/antagonists at NPFF1 and antagonists at NPFF2 (Journigan et al, *J. Med. Chem.*, 57, 8903-27, 2014, chemical structure 6, FIG. 1). These series have the guanidine functionality. While the guanidine functionality has been in some cases associated with high plasma-protein binding and limited BBB penetration, some of these guanidine-containing ligands have been reported to enter the CNS, although to a relatively small extent. So far, only two series of small molecule NPFF ligands that do not possess the guanidine functionality have been reported, but the in vivo effects of these ligands are yet to be investigated (WO 2009/038012, chemical structure 7, FIG. 1; WO 2004/080965, chemical structure 8, FIG. 1).

Figure 2:
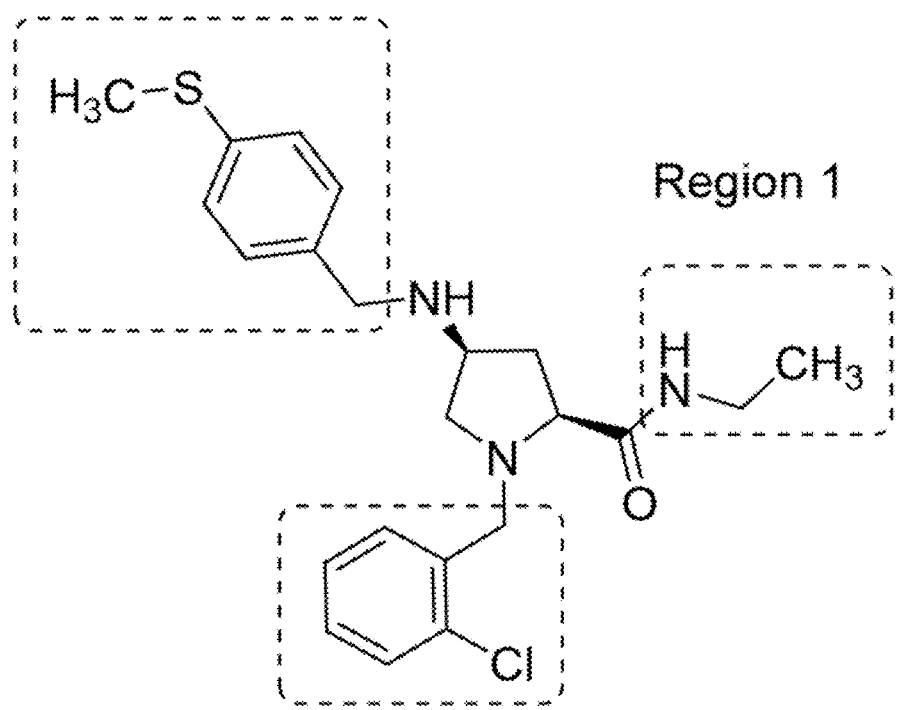
FIG. 2 depicts the chemical structure of proline-based compound 1.

Small non-peptidic compounds are not subject to peptidolytic degradation and thus are more favorable tools to explore biological roles of NPFF receptors. In an effort to develop novel small molecule NPFF ligands, a high throughput screen of a GPCR-oriented compound library was conducted. Compound 1 with a proline scaffold, shown in FIG. 2, emerged as a promising lead with moderate activities on two NPFF subtypes with reasonable physiochemical properties. A synthetic route to this scaffold was developed and a focused library of proline analogs was prepared in order to explore the structure-activity relationships (SARs) at three regions of this scaffold (FIG. 2).

The initial SAR investigation focused on three regions, the carboxamide, the amino center and the 4-position of the proline and revealed substitution at these positions influenced the NPFF antagonism and subtype selectivity. A number of compounds with submicromolar NPFF1 potency have been identified. For example, compound 16 with an n-pentyl amino functionality had a $K_e$ value of 720 nM at NPFF1 and >4 fold preference over NPFF2. Compound 33 with a 4-nitrophenethyl substituent emerged as the most potent analog at NPFF1 ($K_e$=245 nM) and ~3 fold preference over NPFF2. In general, these compounds were more potent at the NPFF1 receptor, but selectivity was only modest against NPFF2. Results from the secondary cAMP assay further confirmed the NPFF antagonistic activities of these compounds and radioligand binding assays demonstrated that the ligands bind to the NPFF receptors with moderate affinity.

The representative compounds 16 and 33 possess moderate solubility and blood-brain barrier permeability, demonstrating the proline scaffold as a potential druglike and potent NPFF template.

The compounds obtained were characterized in calcium mobilization assays to evaluate their activities at both NPFF receptors. Several compounds were further evaluated for their effect in modulating cellular levels of cyclic adenosine monophosphate (cAMP) and their binding affinity to the two NPFF receptors. The drug-like properties such as solubility and blood-brain barrier permeability were then examined. Finally, the effects of these compounds in reversing fentanyl-induced hyperalgesia were investigated.

Traditionally, NPFF activity has been examined using assays such as radiolabeled (radioligand) binding, GTP-γ-S or cAMP assay. To establish a platform allowing for low-cost high-throughput screening, calcium mobilization assays were developed using Chinese hamster ovary (CHO) cells simultaneously over expressing $G\alpha_{i/o}$ protein and either human NPFF1 or NPFF2 receptors. The NPFF1 and NPFF2 stable cell lines were created by transfecting the expression plasmids into RD-HGA16 CHO cells (Molecular Devices), selecting for positive clones using antibiotic resistance, and testing for functional expression of NPFF1 and NPFF2 receptors following procedures previously disclosed (Zhang, Y. et al., *J Med Chem*, 53, 7048-60, 2010; German, N. et al., *J Med Chem*, 57, 7758-69, 2014; Nguyen, T. et al., *Bioorg Med Chem*, 23, 2195-203, 2015). Clones were first screened against 10 μM NPFF to identify clones that had functional NPFF receptors. Eight clones with the highest maximal NPFF response were further evaluated with NPFF concentration-response curves; the clone with the most potent and efficacious NPFF response was chosen as the working clone.

Figure 3:
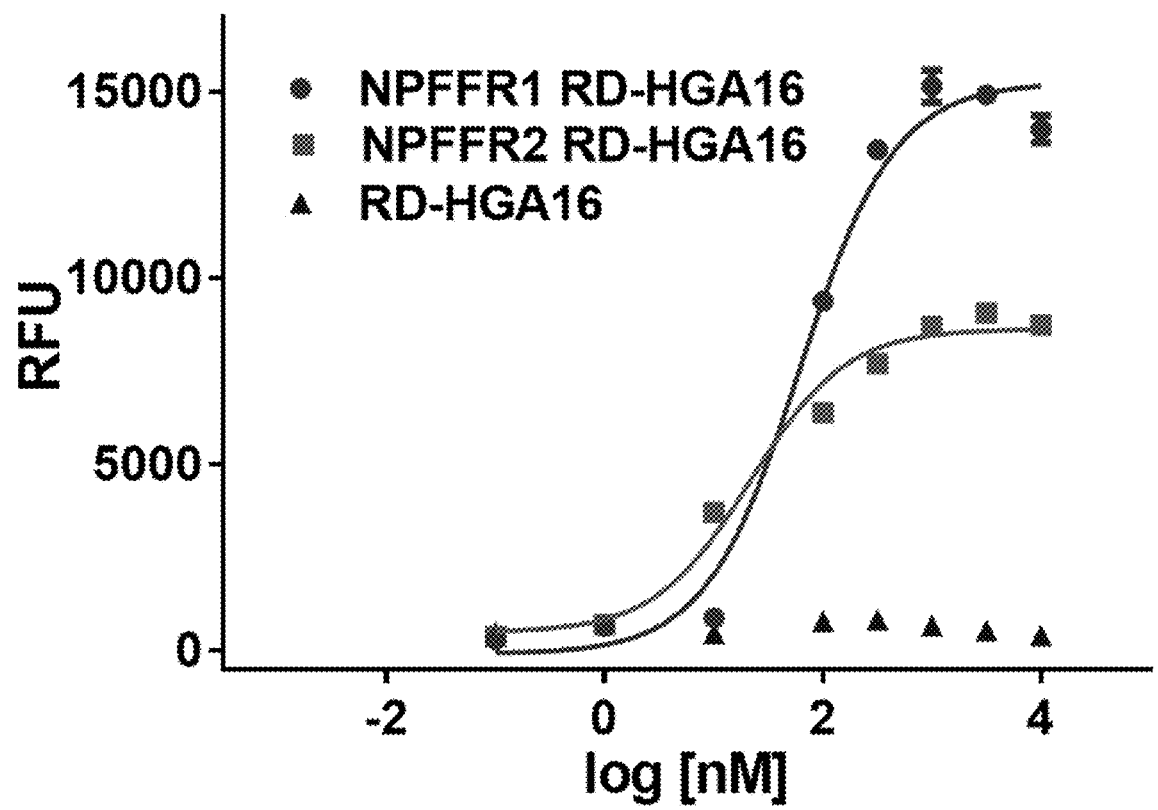
FIG. 3 is a graphical representation of NPFF $EC_{50}$ in calcium mobilization assays, showing data obtained when stable NPFF1 and NPFF2 cell lines were treated with NPFF.

FIG. 3 shows the data obtained when the stable NPFF1 and NPFF2 cell lines were treated with NPFF. In the NPFF1-RD-HGA16 cells, NPFF has an $EC_{50}$ value of ~62 nM and the signal window is 15,000 relative fluorescent units (RFUs). In the NPFF2-RD-HGA16 cells, NPFF has an $EC_{50}$ value of ~22 nM and the signal window is 8,200 RFUs. These NPFF $EC_{50}$ values are consistent with results from other cAMP and GTP-γ-S assays (Gouarderes, C. et al., *Neuropharmacology*, 52, 376-86, 2007; Lameh, J. et al., *J Pharmacol. Exp. Ther.*, 334, 244-54, 2010; Vyas, N. et al., *Peptides*, 27, 990-60, 2006).

In parental RD-HGA-16 CHO cells, there was no response to NPFF, confirming its signaling through NPFF receptors. The NPFF1 stable cell line was successfully miniaturized from 96- to 384-wells (Z' factor=0.75) for library screening.

The NPFF1 FLIPR-based (fluorometric imaging plate reader) calcium mobilization assay was used for the high throughput screen for ligands from an in house GPCR-enriched library as well as to characterize the synthetic compounds obtained. The screened library was highly diverse, including 22,000 compounds, and its content and properties were critically appraised for screening against GPCRs based on a number of factors including maximum diversity, optimal ADME parameters, structural novelty (minimal overlap with scaffolds found in known GPCR ligands and drugs), and pharmacophoric compliance with characteristics prototypical of GPCR ligands.

Library compounds were screened at 10 μM final concentration for both agonist and antagonist activities as part of a 3-addition protocol that was developed, enabling evaluation of both modes of activity with a single assay plate, thereby reducing the overall time and cost of the screening. Concentration-response curves were run with 37 selected antagonists (27 with >65% inhibition and 10 with >85% inhibition) resulting in the confirmed activities of these compounds.

Thus, all of the synthesized compounds were first characterized in NPFF1 and NPFF2 calcium mobilization assays for their ability to antagonize NPFF stimulated calcium influx. Since the NPFF receptors natively couple to $G\alpha_{i/o}$ proteins and inhibit adenylate cyclase, active compounds with apparent dissociation constant $K_e$ values of <1 μM in NPFF1 or NPFF2 calcium assays were selected, and further evaluated in PerkinElmer's Lance cAMP assays.

In both functional assays, $EC_{50}$ curves of the agonist NPFF were obtained alone and together with the test compound, and the right-shift of the agonist curve was measured. The apparent dissociation constant $K_e$ was calculated from compound-mediated inhibition of NPFF activity as previously described (Perrey et al., *J. Med. Chem.*, 56, 6901-16, 2013; Perrey et al., *ACS Chem. Neurosci.* 6, 599-614, 2015). As indicated above, all compounds were tested for agonist activity using the calcium mobilization assay; none showed any significant agonist activity at the either the NPFF1 or NPFF2 receptors (<20% of NPFF $E_{max}$ at 10 μM final). These compounds were also characterized in a radioligand binding assay to measure affinity and confirm that the proline scaffold is a bona fide template as an NPFF ligand. Kinetic solubility and bidirectional MDCK-MDR1 permeability assays of the compounds were performed by Paraza Pharma Inc. (Montreal, Canada) according to their standard protocols.

As a result of the above-described research, proline-based NPFF receptor modulators were discovered according to Formula I.

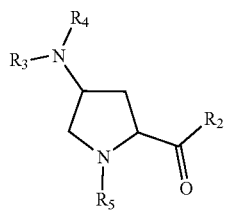

(I)

wherein $R_2$ is selected from $-N-(C_2-C_8 alkyl)_2$ and $NH-R_1$, wherein $R_1$ is selected from $C_2-C_9$ alkyl, heterocyclealkyl, cycloalkylalkyl, aminoalkyl, and arylalkyl; $R_3$ is selected from $C_3-C_9$ alkyl, aryl, heteroaryl, heterocycle, heteroarylalkyl, heterocyclealkyl, and arylalkyl; $R_4$ is selected from H and $C_1-C_2$ alkyl; and $R_5$ is selected from $C_3-C_9$ alkyl, heteroarylalkyl, heteroaryl, heterocyclealkyl, heterocycle, cycloalkylalkyl, and arylalkyl; or a pharmaceutically acceptable salt, amide, ester or prodrug thereof.

Formula I represents proline-based NPFF modulators where each of the three regions of the proline scaffold of Compound 1 may be optimized.

In embodiments of Formula I, wherein $R_1$ is selected from heterocyclealkyl, cycloalkylalkyl, aminoalkyl, and arylalkyl; $R_3$ is selected from heteroarylalkyl, heterocyclealkyl, and arylalkyl; and/or $R_5$ is selected from heteroarylalkyl, heterocyclealkyl, cycloalkylalkyl, and arylalkyl, the alkyl group is $C_1$, $C_2$ or $C_3$. Suitable examples of such groups are shown in the Tables below.

In certain embodiments of Formula I, $R_2$ is $-N-(C_5-C_6 alkyl)_2$.

In certain embodiments of Formula I, $R_2$ is $NH-R_1$. In further embodiments of Formula I, when $R_2$ is $NH-R_1$, $R_1$ is $C_3-C_6$ alkyl.

In some other embodiments of Formula I, when $R_2$ is $NH-R_1$, $R_1$ is benzyl or phenethyl, substituted or unsubstituted. In certain embodiments where $R_1$ is substituted phenethyl, the phenethyl is substituted by lower alkoxy such as methoxy, nitro, lower alkyl, halogen, or halogenated lower alkyl such as $CF_3$. The phenethyl group may be monosubstituted or disubstituted.

Embodiments of $R_2$ as described herein may be combined with any combination of embodiments of $R_3$, $R_4$ and $R_5$ described herein.

In certain embodiments of Formula I, $R_3$ is substituted benzyl or substituted phenethyl with a diversity of substituents. By way of example, the substituents may be halogen, methoxy, methyl, cyano, $N-CH_2$, among others.

In certain embodiments of Formula I, $R_3$ is benzyl or substituted benzyl and $R_4$ is H. In such embodiments where $R_3$ is substituted benzyl, the benzyl is mono- or di-substituted with methoxy.

In certain other embodiments of Formula I, $R_3$ is benzyl or substituted benzyl and $R_4$ is methyl.

In embodiments of Formula I where $R_3$ is monosubstituted benzyl or phenethyl, the substituent is at the 4-position.

In some embodiments of Formula I, $R_5$ is benzyl or substituted benzyl. In such embodiments where $R_5$ is substituted benzyl, the substituents may be halogen or methoxy. In further embodiments where $R_5$ is substituted benzyl, the benzyl is monosubstituted and the substituents may be ortho-substituted halogen or methoxy.

In one embodiment, the proline-based NPFF receptor modulators may be represented by Formula II:

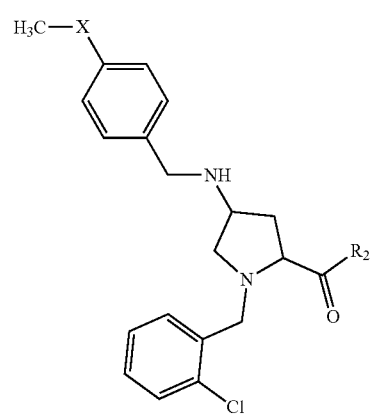

(II)

wherein $R_2$ is selected from $-N-(C_2-C_8 alkyl)_2$ and $NH-R_1$, wherein $R_1$ is selected from $C_2-C_9$ alkyl, heterocyclealkyl, cycloalkylalkyl, aminoalkyl, and arylalkyl; and X is S, SO, $SO_2$, O, NH or $CH_2$. Proline-based NPFF modulators represented by Formula II have modifications in Region 1, the carboxamide region, of Compound 1.

In certain embodiments of Formula II, $R_2$ is $-N-(C_5-C_6 alkyl)_2$.

In certain embodiments of Formula II, X is S or O.

According to some embodiments of Formula II, $R_2$ is $NH-R_1$, wherein $R_1$ is selected from $C_2-C_9$ alkyl, heterocyclealkyl, cycloalkylalkyl, aminoalkyl, and arylalkyl; and X is S, SO, $SO_2$, O, NH or $CH_2$. This embodiment is represented by Formula IIA:

(IIA)

In certain embodiments of Formula IIA, $R_1$ is $C_3-C_6$ alkyl; and X is oxygen. In other embodiments of Formula IIA, $R_1$ is benzyl or phenethyl, substituted or unsubstituted and X is oxygen. In certain embodiments where $R_1$ is substituted phenethyl, the phenethyl is substituted by lower alkoxy, such as methoxy, nitro, lower alkyl, halogen, or halogenated lower alkyl such as $CF_3$.

Table 1 lists the SAR, determined as discussed above, of embodiments corresponding to Formula II, wherein X is oxygen.

TABLE 1
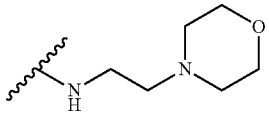 [SMILES: *NCCN1CCOCC1]
| Compound | R₂ | NPFF1 Ke (nM)[a] | NPFF2 Ke (nM)[a] |
| --- | --- | --- | --- |
| 10 | NHMe | >10,000[b] | >10,000[b] |
| 11 | NHEt | >10,000[b] | >10,000[b] |
| 12 | NH(n-Pr) | 2,600 ± 150 | 9,080 ± 220[b] |
| 13 | NH(n-Bu) | 1,240 ± 140 | d |
| 14 | NH(s-Bu) | 1,500 ± 60 | 3,680 ± 350[b] |
| 15 | NH(t-Bu) | 1,880 ± 210 | 1,260 ± 80[c] |
| 16 | NH(n-Pentyl) | 720 ± 10 | 3,090 ± 580[b] |
| 17 | NH(i-Pentyl) | 1,320 ± 90 | 1,540 ± 130[c] |
| 18 | NH(n-hexyl) | 820 ± 80 | 1,490 ± 200[c] |
| 19 | NH(n-decyl) | >10,000[b,c] | d |
| 20 | 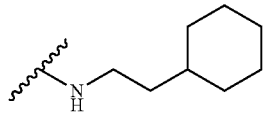 [SMILES: *NCCC1CCCCC1] | 1,960 ± 70 | d |
| 21 | 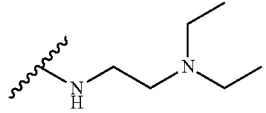 [SMILES: *NCCN(CC)CC] | 1,120 ± 230 | 1,220 ± 360[c] |
| 22 | 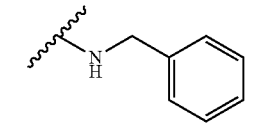 [SMILES: *NCc1ccccc1] | 5,460 ± 490[b] | d |
| 23 | 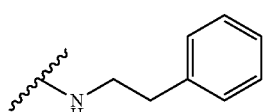 | 780 ± 80[c] | 2,010 ± 440[c] |
| 24 | 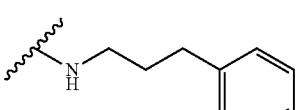 | 850 ± 140 | >10,000[b] |
| 25 | 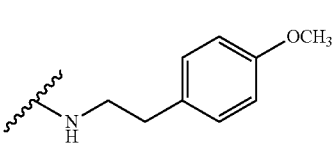 [SMILES: *NCCc1ccc(OC)cc1] | >10,000 | 2,600 ± 280[c] |
| 26 |  | 670 ± 60 | 1,750 ± 110[c] |

TABLE 1-continued
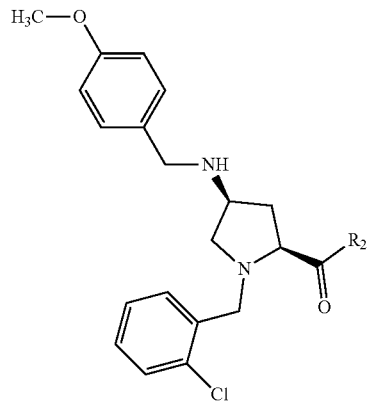
| Compound | R₂ | NPFF1 Ke (nM)[a] | NPFF2 Ke (nM)[a] |
|---|---|---|---|
| 27 | 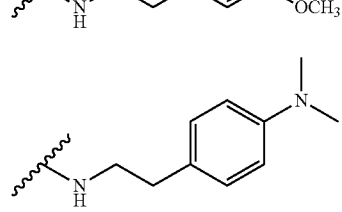 | 1,030 ± 50 | d |
| 28 | 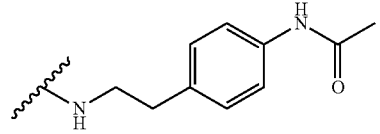 [SMILES: *NCCc1ccc(NC(C)=O)cc1] | 1,200 ± 250 | 2,080 ± 380[d] |
| 29 | 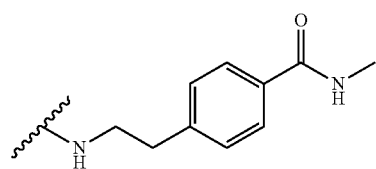 [SMILES: *NCCc1ccc(C(=O)NC)cc1] | 2,510 ± 80 | >10,000[b] |
| 30 | 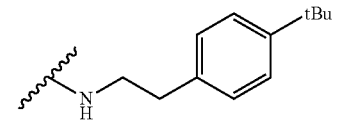 [SMILES: *NCCc1ccc(C(C)(C)C)cc1] | 7,500 ± 1,850[b] | >10,000[b] |
| 31 | 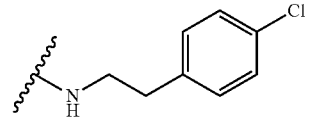 [SMILES: *NCCc1ccc(Cl)cc1] | e | 2,420 ± 260[c] |
| 32 | 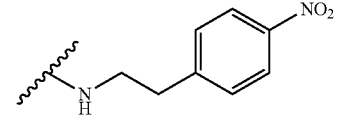 [SMILES: *NCCc1ccc([N+](=O)[O-])cc1] | 990 ± 220[c] | 1,830 ± 90[c] |
| 33 | 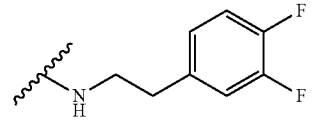 [SMILES: *NCCc1ccc(F)c(F)c1] | 250 ± 60[c] | 690 ± 140[c] |
| 34 |  | 610 ± 130 | 3,490 ± 1,370[b,c] |

TABLE 1-continued

[Core structure: (2S,4S)-4-((4-methoxybenzyl)amino)-1-(2-chlorobenzyl)pyrrolidine-2-carboxamide with R₂ substituent]

| Compound | R₂ | NPFF1 Ke (nM)[a] | NPFF2 Ke (nM)[a] |
|---|---|---|---|
| 35 | -NH-CH₂CH₂-C₆H₄-F (para) | 1,130 ± 110 | 9,880 ± 180[b] |
| 36 | -NH-CH₂CH₂-C₆H₄-CF₃ (para) | 1,670 ± 220 | d |
| 37 | -NH-CH₂CH₂-(4-pyridyl) | 1,820 ± 200 | d |
| 38 | -NH-CH₂CH₂-C₆H₄-C(O)CH₃ (para) | >10,000[b] | >10,000[b] |
| 39 | -NH-CH₂CH₂-C₆H₄-SO₂CH₃ (para) | 1,880 ± 250 | d |
| 40 | NEt₂ | 2,900 ± 150 | 4,930 ± 20[b] |
| 41 | N(n-Pr)₂ | 880 ± 120[c] | 1,730 ± 270[c] |
| 42 | 4-phenylpiperazin-1-yl | 1,330 ± 290[c] | 2,080 ± 300[c] |

[a]Values are the mean ± SEM of at least three independent experiments in duplicate.
[b]Values are the mean ± SME of two independent experiments in duplicate.
[c]Pre-incubation of antagonist and test compound was 45 min or 1 hr.
[d]Compound was inactive in antagonist screen at 10 μM final (N = 2).
[e]Compound appeared cytotoxic in the assay and potency was not determined.

Analogs with a 4-methoxybenzyl group at the 4-position of the proline core, instead of the 4-(methylthio)benzyl group in compound 1, were used in the SAR studies at the carboxamide region because the methoxy moiety is known to have better metabolic stability. Moreover, the corresponding starting materials for the methoxy analogs are more readily available compared to the 4-(methylthio)benzaldehyde. As can be seen from Table 1, the NPFF1 antagonist activity of this series was sensitive to the length of the R₁ substituent of the amide functionality. Methyl and ethyl analogs (10 and 11) were inactive at 10 μM at both NPFF receptors. The antagonist activities at the NPFF1 receptor increased from n-propyl to n-pentyl (12, 13, 16), then decreased slightly with n-hexyl (18) and was completely abolished with n-decyl chain (19). Among the three butyl isomers (13-15), the NPFF1 antagonist activity slightly decreased in the order of n-butyl, s-butyl and t-butyl. In contrast, the NPFF2 antagonist activity increased significantly in the same order, indicating that a linear chain is preferred for NPFF1 selectivity. A similar trend was observed with n-pentyl and iso-pentyl isomers (16 and 17). Between these two isomers, n-pentyl is the more potent and selective NPFF1 antagonist (NPFF1 $K_e$=720 nM, NPFF2 $K_e$=3,090 nM).

When the cyclohexyl (21) was replaced by a phenyl group (24), the NPFF1 activity was slightly improved while retaining selectivity over the NPFF2 receptor. Shortening (23) or lengthening (25) the distance between the phenyl ring and the proline core resulted in weaker potency. Compound 24 (NPFF1 $K_e$=850 nM) emerged as a potent selective NPFF1 antagonist.

Among electron-donating substituents at the para position of the phenyl ring (26-31), 4-methoxy (26, NPFF1 $K_e$=670 nM) was the most potent NPFF1 antagonist. 3,4-Dimethoxy (27), and 4-dimethylamino (28) were slightly less potent. Bulky groups such as 4-acetamido (29), 4-(methylamino) carbonyl (30), and t-butyl (31) were not well tolerated, in agreement with the previous observation that there is limited space at the binding pocket. Turning to electron-withdrawing substituents, 4-nitro (33, NPFF1 $K_e$=250 nM) demonstrated the best NPFF1 antagonist potency among all proline analogs. The results indicate that strong electron-withdrawing groups are favored for good NPFF1 antagonist activity as 3,4-difluoro (34, NPFF1 $K_e$=610 nM) was more potent than 4-chloro (32, NPFF1 $K_e$=990 nM), 4-fluoro (35, NPFF1 $K_e$=1,130 nM) and 4-trifluoromethyl (36, NPFF1 $K_e$=1,670 nM). 4-Pyridinyl (37) which has been used as an isosteric replacement of 4-nitrophenyl, only displayed moderate NPFF1 activity ($K_e$=1,820 nM).

Finally, the NPFF1 antagonist activity of the two bulky electron-withdrawing groups, acetyl (38) and 4-methylsulfonyl (39) was significantly dampened compared to the 4-nitro analog. These data imply that small, strong electron-withdrawing substituents were preferred whereas bulky groups proved to be deleterious for NPFF1 antagonist activity. Similar to the aliphatic series, these phenethyl analogs were not potent at the NPFF2 receptor except 4-methoxy (26), diethylamino (28), 4-chloro (32), 4-nitro (33), and 3,4-difluoro (34).

Next, the effect of disubstituted amides at this region was also investigated. Diethylamino and dipropylamino analogs (40, NPFF1 $K_e$=2,900 nM and 41, NPFF1 $K_e$=880 nM) were more potent at the NPFF1 receptor compared to their monosubstituted amide counterparts (11, NPFF1 $K_e$>10,000 nM and 12, NPFF1 $K_e$=9,080 nM). Compound 42 (NPFF1 $K_e$=1,330 nM) with a rigid spacer between the phenyl ring and the amide was less active at the NPFF1 receptor compared to 24 (NPFF1 $K_e$=850 nM) with a flexible ethylene linker.

TABLE 2

SAR at the carboxamide region of the 4-(4-methylthio)benzylamino series.

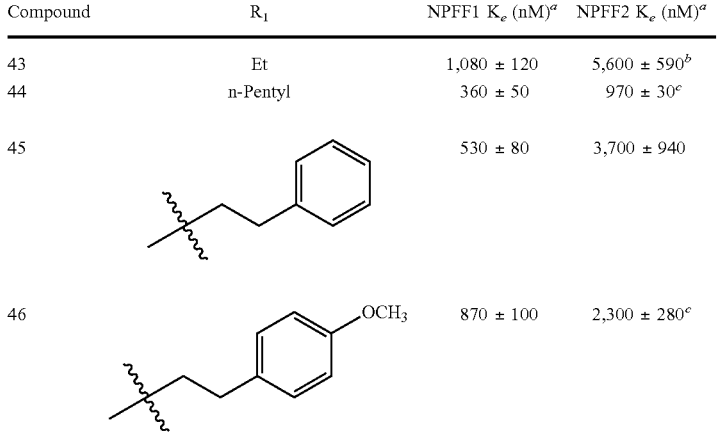

| Compound | $R_1$ | NPFF1 $K_e$ (nM)[a] | NPFF2 $K_e$ (nM)[a] |
|---|---|---|---|
| 43 | Et | 1,080 ± 120 | 5,600 ± 590[b] |
| 44 | n-Pentyl | 360 ± 50 | 970 ± 30[c] |
| 45 | phenethyl | 530 ± 80 | 3,700 ± 940 |
| 46 | 4-methoxyphenethyl | 870 ± 100 | 2,300 ± 280[c] |

TABLE 2-continued

SAR at the carboxamide region of the 4-(4-methylthio)benzylamino series.

| Compound | R$_1$ | NPFF1 K$_e$ (nM)$^a$ | NPFF2 K$_e$ (nM)$^a$ |
|---|---|---|---|
| 47 | (4-nitrophenethyl) | 370 ± 70$^c$ | 1,350 ± 200 |
| 48 | (3,4-difluorophenethyl) | 470 ± 60 | 880 ± 160$^c$ |

$^a$Values are the mean ± SEM of at least three independent experiments in duplicate.
$^b$Values are the mean ± SME of two independent experiments in duplicate.
$^c$Pre-incubation of antagonist and test compound was 1 hr.

Since the initial compound 1 has a 4-methylthio at the 4-benzyl group on the proline scaffold, after exploring various substituents at the carboxamide region with a 4-(4-methoxybenzyl) substitution of the proline scaffold, several of the more potent analogs from Table 1 were selected and the effects examined of the 4-methylthio substitution. As shown in Table 2, the resynthesized 43 (NPFF1 K$_e$=1,080 nM, NPFF2 K$_e$ 5,600 nM) had comparable potency at both receptors to 1 (NPFF1 K$_e$=1,620 nM, NPFF2 K$_e$=7,250 nM) from the screening library. Two (methylthio)benzyl analogs with alkyl groups at the carboxamide were more potent NPFF1 antagonists than their methoxy counterparts (NPFF1: 43 K$_e$=1,080 nM vs. 11 K$_e$>10,000 nM; 44 K$_e$=360 nM vs. 16 K$_e$=720 nM). Similarly, phenethyl (45) and 3,4-difluorophenethyl (48) analogs demonstrated slightly better NPFF1 activities in the thioether series than their methoxy counterparts (45 K$_e$=530 nM vs. 24 K$_e$=850 nM; 48 K$_e$=470 nM vs. 34 K$_e$=610 nM). On the other hand, the 4-methoxy (46) and 4-nitro (47) analogs were slightly less potent than their methoxy equivalents (46 K$_e$=870 nM vs. 26 K$_e$=670 nM, 47 K$_e$=370 nM vs. 33 K$_e$=250 nM). At the NPFF2 receptor, this series appeared to be more active and thus, less selective for NPFF1 receptor, compared to the 4-(4-methoxybenzyl)amino analogs except for 46 and 47.

Collectively, these results highlight the importance of the substituent size and a preference for lipophilicity and some flexibility at this binding pocket. The most potent NPFF1 ligand is 4-nitro (33) with a NPFF1 K$_e$=250 nM. Several ligands with moderate activity against NPFF1 with no/weak NPFF2 activity were also identified. Throughout the course of these studies, most of the compounds we tested displayed competitive antagonism in the curve-shift assays; however, some compounds (23, 32, 33, 41, 42, 46) showed evidence of insurmountable antagonism by shifting the curve to the right and also depressing the maximal NPFF signal. While allosteric modulators commonly produce such a response, this type of antagonism can also be observed with competitive orthosteric antagonists with slow dissociation rates. Such antagonists have been worked with previously and showed that by performing the curve-shift assays with longer antagonist-receptor incubation periods, the system reaches equilibrium, and hence the compounds produce a typical competitive antagonist profile. Indeed, when the longer incubations were applied to the NPFF assays, the compounds displayed the typical competitive antagonist activity profile.

In another embodiment, the NPFF modulators may be represented by Formula III:

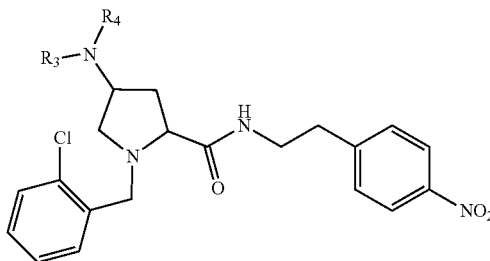

(III)

wherein $R_3$ is selected from $C_3$-$C_9$ alkyl, aryl, heteroaryl, heterocycle, heteroarylalkyl, heterocyclealkyl, and arylalkyl; and $R_4$ is selected from H and $C_1$-$C_2$ alkyl.

In certain embodiments of Formula III, $R_3$ is substituted benzyl or substituted phenethyl with a diversity of substituents. By way of example, the substituents may be halogen, methoxy, methyl, cyano, N—CH$_2$, among others.

In certain embodiments of Formula III, $R_3$ is benzyl or substituted benzyl, phenethyl or substituted phenethyl, and $R_4$ is H. In some embodiments where $R_3$ is substituted benzyl, the benzyl is substituted by methoxy.

In certain other embodiments of Formula III, $R_3$ is benzyl or substituted benzyl and $R_4$ is methyl.

In other embodiments of Formula III, $R_3$ is $C_3$-$C_6$ alkyl.

Table 3 lists the SAR, determined as discussed above, of analogs of Compound 1 substituted at region 2, including embodiments corresponding to Formula III.

TABLE 3

| Compound | R$_3$ | R$_4$ | NPFF1 K$_e$ (nM) | NPFF2 K$_e$ (nM) |
|---|---|---|---|---|
| 52 | n-Pr | H | 5,160 ± 770 | >10,000 |
| 53 | n-Bu | H | 6,120 ± 2,200 | >10,000 |
| 54 | n-Pentyl | H | 2,480 ± 280 | >10,000 |
| 55 | n-Hexyl | H | 2,320 ± 320 | 4,470 ± 2,110 |
| 56 | benzyl | H | 1,230 ± 240 | 1,400 ± 350 |
| 57 | benzyl | Me | 1,930 ± 180 | 1,500 ± 810 |
| 58 | phenethyl | H | 1,150 ± 260 | 1,130 ± 240 |
| 33 | 4-methoxybenzyl | H | 250 ± 60[b] | 690 ± 140[b] |
| 59 | 3-methoxybenzyl | H | 1,390 ± 290 | 2,820 ± 1,420 |
| 60 | 3,4-dimethoxybenzyl | H | 1,920 ± 790 | 3,150 ± 560 |
| 61 | 4-hydroxybenzyl | H | 4,790 ± 1,390 | 6,370 ± 1,700 |
| 62 | 4-CF$_3$-benzyl | H | 2,060 ± 180 | 6,380 ± 4,670 |
| 63 | 4-chlorobenzyl | H | 680 ± 180 | 1,860 ± 620 |
| 64 | 4-fluorobenzyl | H | 960 ± 690 | >10,000 |

[a]Values are the mean ± SEM of at least three independent experiments performed in duplicate.
[b]Pre-incubation of antagonist and test compound was 1 hour.

To explore the SARs at the region 2,4-nitrophenethylamino was selected as an optimal substituent at $R_1$ and various substituents were introduced at the amine center at the 4-position of the proline scaffold (Table 3). A similar trend of the substituent size in the aliphatic series as discussed above was observed (52-55). As the length of the side chains increased from n-propyl to n-hexyl, the NPFF1 activity became more potent against both receptors. The activity appeared to plateau as the side chain reached 5 to 6 carbons. Phenylmethyl (56) and phenethyl (58) had similar activities against both receptors. N-methylation of the amino group resulting in the tertiary amine analog (57) slightly dampened the activities at both NPFF subtypes. This trend is believed to imply that this binding pocket also has a limited space similar to that of the region 1.

The effects of substituents at different positions on the benzyl rings (33, 59-64) were further probed. Switching the 4-OMe to 3-position or addition of another OMe at the 3-position on the phenyl decreased activities on both receptor subtypes. The electronic effect did not appear to be a determining factor for the ring substitution. Replacing the 4-OMe by another electron-donating group 4-OH caused a loss of activity. The electron-withdrawing trifluoromethyl group was not active while the other two halogen analogs had good activity against NPFF1. It is noteworthy that compound 64 has more than 10 fold selectivity for NPFF1 receptor.

In another embodiment, the NPFF modulators may be represented by Formula IV:

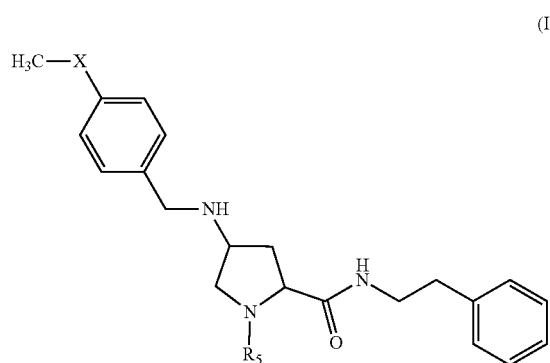

(IV)

wherein $R_5$ is selected from $C_3$-$C_9$ alkyl, heteroarylalkyl, heteroaryl, heterocyclealkyl, heterocycle, cycloalkylalkyl, and arylalkyl; and X is S, SO, $SO_2$, O, NH or $CH_2$.

In certain embodiments of Formula IV, $R_5$ is selected from $C_3$-$C_9$ alkyl, heteroarylalkyl, heterocyclealkyl, cycloalkylalkyl, and arylalkyl and X is O.

In certain embodiments of Formula IV, $R_5$ is selected from $C_3$-$C_9$ alkyl, heteroarylalkyl, heterocyclealkyl, cycloalkylalkyl, and arylalkyl and X is S.

In certain embodiments of Formula IV, $R_5$ is selected from $C_3$-$C_9$ alkyl, heteroarylalkyl, heterocyclealkyl, cycloalkylalkyl, and arylalkyl and X is NH.

In some embodiments of Formula I, $R_5$ is benzyl or substituted benzyl and X is O. In such embodiments where $R_5$ is substituted benzyl, the substituents may be halogen or methoxy. In further embodiments where $R_5$ is substituted benzyl, the benzyl is monosubstituted and the substituents may be halogen or methoxy at the 2- or 3-position.

Table 4 lists the SAR, determined as discussed above, of analogs of Compound 1, substituted at region 3 of compound 1, including embodiments corresponding to Formula IV.

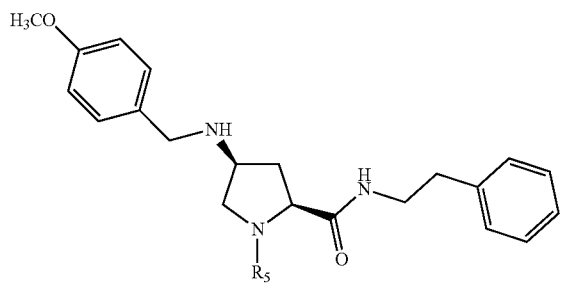

TABLE 4

| Compound | $R_5$ | NPFF1 $K_e$ (nM)[a] | NPFF2 $K_e$ (nM)[a] |
|---|---|---|---|
| 74 | n-hexyl | 1,450 ± 150 | 7,100 ± 760 |
| 75 | cyclohexylmethyl | 650 ± 70 | 3,640 ± 830 |
| 76 | benzyl | 1,270 ± 140 | >10,000 |
| 24 | 2-Cl-benzyl | 850 ± 140 | 9,390 ± 4,670 |
| 77 | 3-Cl-benzyl | 580 ± 50 | 4,100 ± 1,490 |
| 78 | 4-Cl-benzyl | 2,150 ± 430 | 4,850 ± 190 |
| 79 | 2-OMe-benzyl | 1,230 ± 240 | 5,110 ± 900 |
| 80 | 3-OCH$_3$-benzyl | 2,460 ± 390 | >10,000 |
| 81 | 3,4-diOCH$_3$-benzyl | 9,020 ± 900 | 5,360 ± 720 |
| 82 | 2-Me-benzyl | 490 ± 70 | 3,940 ± 550 |
| 83 | 4-Me-benzyl | 1,320 ± 220 | >10,000 |
| 84 | 4-OH-benzyl | >10,000 | >10,000 |

TABLE 4-continued

| Compound | R₅ | NPFF1 $K_e$ (nM)[a] | NPFF2 $K_e$ (nM)[a] |
|---|---|---|---|
| 85 | 4-NMe₂-benzyl | 3,510 ± 860 | >10,000 |
| 86 | 4-CN-benzyl | 3,830 ± 260 | >10,000 |
| 87 | 2-naphthylmethyl | 1,720 ± 240 | 7,220 ± 2,360 |
| 88 | 3,4-methylenedioxybenzyl | 1,860 ± 430 | >10,000 |

[a]Values are the mean ± SEM of at least three independent experiments in duplicate.

In the synthesis, the nitro group is easily reduced under the conditions employed to remove protective groups of the proline nitrogen and the amino group at the 4-position. In order to simplify the synthetic effort to prepare a series of analogs at the region 3, analogs with a phenethyl group in region 1 were explored, instead of 4-nitrophenylethyl, and the 4-methoxybenzyl group was used in region 2.

As illustrated in Table 4, $R_5$ could be an acyclic (i.e. n-hexyl, 74), cyclic alkyl (i.e. cyclohexylmethyl, 75), or benzyl substituent (24, 76-88). The position of the substituents has a strong influence in the activities. Among the substituted benzyl analogs, substitutions at the 2- and 3-positions were preferred to the 4-position. Within the three chloro substituted isomers, substitution at the 3-position is the most potent analog (77, $K_e$=580 nM) with a moderate subtype selectivity (>10 fold) over the NPFF2 receptor. On the other hand, the methoxy (79) and methyl (82) groups seems to prefer the 2-position. Similarly, other substituents such as 4-hydroxy (84), 4-dimethylamino (85), and 4-cyano (86) groups weakened the NPFF activities. A bulky substituent such as 2-naphthylmethyl (87) or 3,4-methylenedioxybenzyl (88) was also not favored.

Several compounds were further characterized in radioligand binding and cAMP assays (Table 5). In general, the data obtained from all three assays compare well with each other. Compounds that were potent antagonists in the calcium mobilization assays were also potent antagonists in the secondary cAMP assay that measure native G-protein coupling. Further, the binding assays showed that all compounds bind to the NPFF receptors and that potent compounds (e.g., compounds 33 and 34) in the NPFF1 functional assays have potent binding affinities.

TABLE 5

Results from the cAMP, radioligand binding and calcium mobilization assays of representative compounds.

| Compound # | R₁ | Radioligand assay $K_i$ NPFF1 (nM) | Radioligand assay $K_i$ NPFF2 (nM) | cAMP assay[b] $K_e$ NPFF1 (nM) | cAMP assay[b] $K_e$ NPFF2 (nM)[a] | Calcium mobilization assay[b] $K_e$ NPFF1 (nM) | Calcium mobilization assay[b] $K_e$ NPFF2 (nM) |
|---|---|---|---|---|---|---|---|
| 16 | n-Pentyl | 890 ± 50 | 1,440 ± 130 | 340 ± 80 | 2,150 ± 360 | 720 ± 10 | 3,090 ± 580 |
| 24 | phenethyl | 710 ± 20 | 1,230 ± 270 | 770 ± 120 | 3,790 ± 450 | 850 ± 140 | >10,000[b] |
| 26 | 4-OCH₃-phenethyl | 920 ± 30 | 1,460 ± 50 | 570 ± 150[c] | 2,560 ± 200 | 670 ± 60 | 1,750 ± 110[c] |
| 33 | 4-NO₂-phenethyl | 610 ± 30 | 1,670 ± 60 | 490 ± 90 | 1170 ± 360 | 250 ± 60[c] | 690 ± 140[c] |
| 34 | 3,4-difluoro-phenethyl | 560 ± 40 | 1,490 ± 270 | 570 ± 170 | 2,160 ± 300 | 610 ± 130 | 3,490 ± 1,370[b,c] |

TABLE 5-continued

Results from the cAMP, radioligand binding and calcium mobilization assays of representative compounds.

| Compound # | R$_1$ | Radioligand assay | | cAMP assay[b] | | Calcium mobilization assay[b] | |
|---|---|---|---|---|---|---|---|
| | | K$_i$ NPFF1 (nM) | K$_i$ NPFF2 (nM) | K$_e$ NPFF1 (nM) | K$_e$ NPFF2 (nM)[a] | K$_e$ NPFF1 (nM | K$_e$ NPFF2 (nM) |
| 63 | 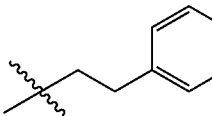 | d | d | 1,552 | 1,757 | 510 ± 180 | 1,860 ± 620 |
| 64 | 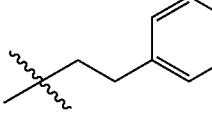 | d | d | 1,445 | 960 | 960 ± 690 | >10,000 |

[a]Values are the mean ± SEM of at least two independent experiments in duplicate.
[b]Values are the mean ± SEM of at least three independent experiments in duplicate.
[c]Pre-incubation of antagonist and receptor was 1 hour.
[d]Not determined One of major challenges for CNS drugs is their ability to cross the blood-brain barrier (BBB) and reach the CNS. For a majority of drugs, the blood brain barrier permeability is affected by two factors, the ability to permeate through the BBB passively and the avoidance of being effluxed out by the transport proteins such as the P-glycoprotein. Thus, representative compound 33 was evaluated, which has good antagonist activities in the bidirectional transport assay using the MDCK-MDR1 cells which are stably transfected with human MDR1 cDNA so that they express a higher level of the P-glycoprotein (Pgp) than the wild type. Compound 33 traversed the cell barrier from the apical (A) to basolateral (B) at a rate of $2.7 \times 10^{-6}$ cm/s, and the reverse direction B to A at a rate of $3.6 \times 10^{-6}$ cm/s, demonstrating a moderate BBB permeability (within the range of $3\text{-}6 \times 10^{-6}$ cm/s).[33] The efflux ratio ($P_{B \to A}/P_{A \to B}$) is 1.3, indicating that the compound is not a Pgp substrate. (Di et al., *In Drug-Like Properties: Concepts, Structure Design and Methods from ADME to Toxicity Optimization*, Academic Press, pp. 141-159 (2016)). In addition, the compound also has a solubility 45.9±7.7 µM (Mean±% CV) which falls in the range of 10-60 µg/ml for compounds with moderate to good solubility according to Di et al., *In Drug-Like Properties: Concepts, Structure Design and Methods from ADME to Toxicity Optimization*, Academic Press, pp. 56-85 (2016).

The activity shown indicates the proline-based neuropeptide FF receptor modulators are useful as NPFF antagonists.

Terms are used within their accepted meanings. The following definitions are meant to clarify, but not limit, the terms defined.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the disclosure.

Accordingly, $C_3$-$C_9$ alkyl, by way of example, is intended to include propyl, butyl, pentyl, hexyl, heptyl, octyl, and nonyl, including straight chain as well as branched groups of such types, such as isopropyl and tert-butyl. It therefore is to be appreciated that identification of a carbon number range, e.g., $C_1$-$C_{12}$ or $C_1$-$C_6$, as broadly applicable to a substituent moiety, enables, in specific embodiments of the disclosure, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the disclosure, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The term "lower alkyl" includes any of $C_1$, $C_2$, or $C_3$ alkyl.

When the term "alkyl" used as a suffix in conjunction with a second group, as in "arylalkyl", "aminoalkyl," "cycloalkylalkyl", or "heterocyclealkyl" the second group is then connected to the rest of the molecule via an alkyl radical. By way of example, where "arylalkyl", "aminoalkyl," "cycloalkylalkyl", or "heterocyclealkyl" etc., is used, the alkyl radical may be any of $C_1$, $C_2$, $C_3$ or $C_4$ alkyl.

"Cycloalkyl" refers to an optionally substituted non-aromatic cyclic hydrocarbon ring. Unless otherwise indicated, cycloalkyl is composed of three to eight carbon atoms. Exemplary "cycloalkyl" groups include, but are not limited to, cyclopropyl, cyclobutyl, cyclopentyl, cyclohexyl, and cycloheptyl. The cycloalkyl group may be substituted or unsubstituted, for, example by a halogen, or a $C_1$-$C_3$-alkyl.

"Heterocycle" refers to saturated cyclic radicals containing one or more heteroatoms (e.g., O, N, S) as part of the ring structure and having two to seven carbon atoms in the ring. In embodiments, a heterocycle may be fused to an aryl group such as phenyl. The heterocycle may be substituted or unsubstituted, for example, by a halogen, amino, cyano, nitro, carbonyl, amido, acetyl, carboxymethyl, $C_1$-$C_3$-alkyl or $C_1$-$C_3$ alkoxy.

"Heteroaryl" refers to unsaturated aromatic cyclic radicals containing one or more heteroatoms (e.g., O, N, S) as part of the ring structure and having two to seven carbon atoms in the ring. Heteroaryl groups may include furanyl, thienyl, pyridyl, pyrrolyl, pyrrolo, pyrimidyl, pyrazinyl, imidazolyl and the like. The heteroaryl group may be substituted or unsubstituted, for example, by a halogen, amino, cyano, nitro, carbonyl, amido, acetyl, carboxymethyl, $C_1$-$C_3$-alkyl or $C_1$-$C_3$ alkoxy.

In addition, the term "heteroaryl" is used to include fused bicyclic ring systems that contain one or more heteroatoms. Examples of such heteroaryl groups include benzodioxole, benzisoxazolyl, benzofuranyl.

"Aryl" as used herein includes hydrocarbons derived from benzene or a benzene derivative that are unsaturated aromatic carbocyclic groups of from 6 to 10 carbon atoms. The aryls may have a single or multiple rings. Examples include phenyl, benzyl, or naphthyl. The aryl group may be substituted or unsubstituted, for example, by a halogen, amino, cyano, nitro, carbonyl, amido, acetyl, carboxymethyl, $C_1$-$C_3$-alkyl or $C_1$-$C_3$ alkoxy.

"Arylalkyl" includes, by way of example, benzyl and phenethyl.

"Alkylcycloalkyl" includes, by way of example, a methylcyclohexyl group.

The compounds of the disclosure may be further specified in specific embodiments by provisos or limitations excluding specific substituents, groups, moieties or structures, in relation to various specifications and exemplifications thereof set forth herein. Thus, the disclosure contemplates restrictively defined compositions, e.g., a composition wherein R is $C_1$-$C_{12}$ alkyl, with the proviso that R≠$C_i$ alkyl when $R_1$ is a specified molecular component, and i is a specific carbon number. The substituents may be selected and combined with each other in any manner resulting in a compound according to Formulas I, II, IIA, III or IV.

Certain of the compounds disclosed herein may exist as stereoisomers including optical isomers. Scope of the disclosure includes all stereoisomers in both the racemic mixtures of such stereoisomers as well as the individual enantiomers which may be separated according to methods that are well known to those of ordinary skill in the art. When chiral centers are present, the stereochemistry of the structures includes both R and S configuration, unless otherwise indicated.

The disclosure, as variously set out herein in respect of various described features, aspects and embodiments, may in particular implementations be constituted as comprising, consisting, or consisting essentially of, some or all of such features, aspects and embodiments, as well as elements and components thereof being aggregated to constitute various further implementations of the disclosure. The disclosure contemplates such features, aspects and embodiments in various permutations and combinations, as being within the scope of the disclosure. The disclosure may therefore be specified as comprising, consisting or consisting essentially of, any of such combinations and permutations of these specific features, aspects and embodiments, or a selected one or ones thereof.

The term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The NPFF receptor modulators may be useful in pain management to reduce opioid tolerance and hyperalgesia, addiction disorders, anti-inflammation, feeding, blood pressure, insulin release, attenuation of fever, reduction of anxiety, attenuation of limbic seizure activity, attenuation of opioid-induced hypothermia, and cardiovascular modulation, by way of example.

In one aspect, the NPFF receptor modulators may be used in combination with other drugs or agents, or in conjunction with a variety of psychotherapies useful in the treatment of the type of conditions and disorders modulated by NPFF receptors Drugs or agents which may be used with the NPFF receptor modulators and compositions containing same may include typical and/or atypical antipsychotics such as haloperidol and aripiperazole or monoamine reuptake inhibitors such as fluoxetine and sertraline.

In view of the opioid-modulating properties of the NPFF system, other combination therapy applications of the NPFF receptor modulators and compositions of the present disclosure include their contemporaneous administration with opioids, e.g., fentanyl, morphine, oxycodone, hydrocodone, buprenorphine, etc., to combat hyperalgesia and tolerance effects of the opioids.

In another aspect of the disclosure, a method for treating a subject having or susceptible to a condition or disorder where modulation of neuropeptide FF receptor activity is of therapeutic benefit is provided, the method comprising administering to said subject having or susceptible to said condition or disorder an effective amount of a neuropeptide FF modulator according to Formula I:

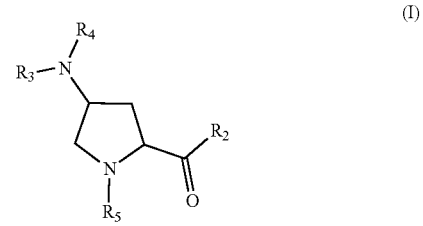

(I)

wherein $R_2$ is selected from —N—($C_2$-$C_5$alkyl)$_2$, and NH—$R_1$, wherein $R_1$ is selected from $C_2$-$C_9$ alkyl, heterocyclealkyl, cycloalkylalkyl, aminoalkyl, and arylalkyl; $R_3$ is selected from $C_3$-$C_9$ alkyl, aryl, heteroaryl, heterocycle, heteroarylalkyl, heterocyclealkyl, and arylalkyl; $R_4$ is selected from H and $C_1$-$C_2$ alkyl; and $R_5$ is selected from $C_3$-$C_9$ alkyl, heteroarylalkyl, heteroaryl, heterocyclealkyl, heterocycle, cycloalkylalkyl, and arylalkyl; or a pharmaceutical salt, amide, ester or prodrug thereof.

In embodiments of Formula I, wherein $R_1$ is selected from heterocyclealkyl, cycloalkylalkyl, aminoalkyl, and arylalkyl; $R_3$ is selected from heteroarylalkyl, heterocyclealkyl, and arylalkyl; and/or $R_5$ is selected from heteroarylalkyl, heterocyclealkyl, cycloalkylalkyl, and arylalkyl, the alkyl group is $C_1$, $C_2$ or $C_3$. Suitable examples of such groups are shown in the Tables above.

In certain embodiments of Formula I, $R_2$ is NH—$R_1$. In further embodiments of Formula I, when $R_2$ is NH—$R_1$, $R_1$ is $C_3$-$C_6$ alkyl.

In some other embodiments of Formula I, when $R_2$ is NH—$R_1$, $R_1$ is benzyl or phenethyl, substituted or unsubstituted. In certain embodiments where $R_1$ is substituted phenethyl, the phenethyl is substituted by lower alkoxy such as methoxy, nitro, lower alkyl, halogen, or halogenated lower alkyl such as $CF_3$. In certain embodiments, the phenethyl group is monosubstituted or disubstituted.

Embodiments of $R_2$ as described herein may be combined with any combination of embodiments of $R_3$, $R_4$ and $R_5$ described herein.

In certain embodiments of Formula I, $R_3$ is substituted benzyl or substituted phenethyl with a diversity of substituents. By way of example, the substituents may be halogen, methoxy, methyl, cyano, N—$CH_2$, among others.

In certain embodiments of Formula I, $R_3$ is benzyl or substituted benzyl and $R_4$ is H. In such embodiments where $R_3$ is substituted benzyl, the benzyl is mono- or di-substituted with methoxy.

In certain other embodiments of Formula I, $R_3$ is benzyl or substituted benzyl and $R_4$ is methyl.

In embodiments of Formula I where $R_3$ is monosubstituted benzyl or phenethyl, the substituent is at the 4-position.

In some embodiments of Formula I, $R_5$ is benzyl or substituted benzyl. In such embodiments where $R_5$ is substituted benzyl, the substituents may be halogen or methoxy. In further embodiments where $R_5$ is substituted benzyl, the benzyl is monosubstituted and the substituents may be ortho-substituted halogen or methoxy.

In one embodiment, the proline-based NPFF modulators may be represented by Formula II:

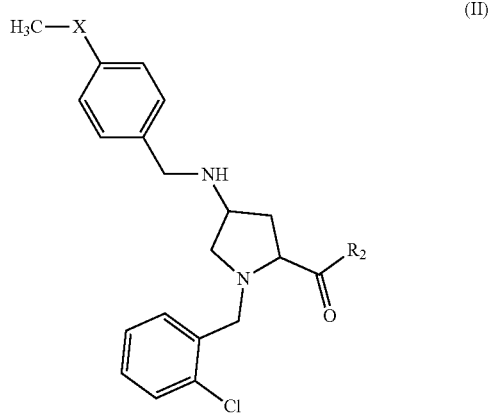

(II)

wherein $R_2$ is selected from —N—$(C_2$-$C_5$alkyl$)_2$, and NH—$R_1$, wherein $R_1$ is selected from $C_2$-$C_9$ alkyl, heterocyclealkyl, cycloalkylalkyl, aminoalkyl, and arylalkyl; and X is S, SO, $SO_2$, O, NH or $CH_2$.

According to some embodiments of Formula II, $R_2$ is NH—$R_1$, wherein $R_1$ is selected from $C_2$-$C_9$ alkyl, heterocyclealkyl, cycloalkylalkyl, aminoalkyl, and arylalkyl; and X is S, SO, $SO_2$, O, NH or $CH_2$. This embodiment is represented by Formula IIA:

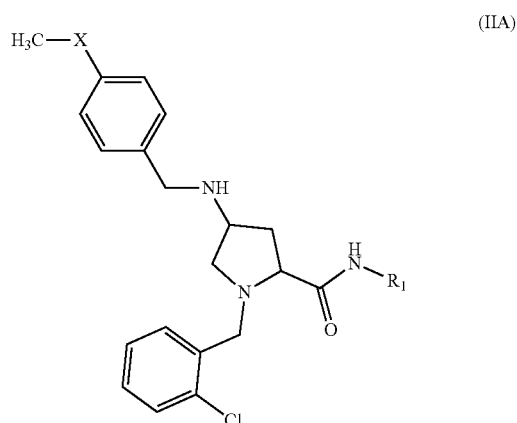

(IIA)

In certain embodiments of Formula IIA, $R_1$ is $C_3$-$C_6$ alkyl; and X is oxygen. In other embodiments of Formula IIA, $R_1$ is benzyl or phenethyl, substituted or unsubstituted and X is oxygen. In certain embodiments where $R_1$ is substituted phenethyl, the phenethyl is substituted by lower alkoxy, such as methoxy, nitro, lower alkyl, halogen, or halogenated lower alkyl such as $CF_3$.

In other embodiments of the method for treating a subject, the NPFF receptor modulators may be according to any of the embodiments disclosed herein for Formulas I, II or IIA.

In certain embodiments of the method for treating a subject, the NPFF receptor modulators may be according to any of Formulas III or IV as described herein.

In certain embodiments of the method for treating a subject, the modulation of neuropeptide FF receptor activity is antagonistic activity.

In a certain embodiment, a method is provided for treating a subject having a condition or disorder where modulation of neuropeptide S receptor activity is of therapeutic benefit comprising administering to said subject having or susceptible to said condition or disorder an effective amount of a compound according to one of Formulas I, II, IIA, III or IV demonstrating selective binding and functional antagonist activity at a neuropeptide FF receptor.

The condition or disorder to be treated may be related to pain management, addiction disorders, anti-inflammation, feeding, blood pressure, insulin release, attenuation of fever, reduction of anxiety, attenuation of limbic seizure activity, attenuation of opioid-induced hypothermia, cardiovascular modulation, attenuation of hyperalgesia and/or opioid tolerance or other conditions or disorder modulated by the NPFF receptors.

In embodiments, the NPFF receptor modulator or antagonist administered is a pharmaceutically acceptable salt, amide, ester or prodrug of any modulators of the foregoing formulas I, II, IIA, III or IV. In this aspect, any of the compounds of Formulas I, II, IIA, III or IV may be combined with a pharmaceutically acceptable carrier.

Salts of the compounds of the present disclosure may be made by methods known to a person skilled in the art. The acid may be an inorganic acid or an organic acid. Suitable acids include, for example, hydrochloric, hydroiodic, hydrobromic, sulfuric, phosphoric, citric, acetic and formic acids.

A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems and administration modalities, see Kirk-Othmer Encyclopedia of Chemical Technology, Fourth Edition, Volume 8, pp. 445-475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this disclosure may include, in admixture, a pharmaceutically acceptable excipient (carrier) and one or more of the NPFF receptor modulators, as described herein as an active ingredient.

The NPFF receptor ligands may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. NPFF receptor modulators active on parenteral administration may be administered by depot injection, implants including Silastic™ and biodegradable implants, skin patches, skin creams, or intramuscular and intravenous injections.

Compositions containing the NPFF receptor modulators may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylenesorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the disclosure suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitolamhydrides, such as sorbitan mono-oleate, and condensation products of these partial esters with ethylene oxide, such as polyoxyethylenesorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as, for example, by aseptic filtration, or irradiation.

Aqueous formulations (i.e., oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The NPFF receptor modulators may also be administered in the form of suppositories for rectal administration of the drug. These compositions can be prepared by mixing the drug with a suitable nonirritating excipient which is solid at ordinary temperatures but liquid at rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products as disclosed herein which are preferably administered by the topical route may be administered as applicator sticks, solutions, suspensions, emulsions, gels, creams, ointments, pastes, jellies, paints, powders, and aerosols.

The compositions may, if desired, the person or dispenser device which may contain one or more unit dosage forms containing an active ingredient. Pharmaceutical compositions comprising an NPFF modulator as described herein and formulated in a compatible pharmaceutical carrier may also be prepared, placed in an appropriate container, and labeled for treatment of an indicated condition.

The advantages and features of the disclosure are further illustrated with reference to the following examples, which are not to be construed as in any way limiting the scope of the disclosure but rather as illustrative of embodiments of the disclosure.

EXAMPLES

Chemistry. Compounds 10-48 were synthesized following procedures depicted in Scheme 1. trans-4-Hydroxy-L-proline methyl ester (2) underwent reductive amination by sodium triacetoxyborohydride in 1,2-dichloroethane to give the intermediate 3 which was then converted to a tosylated derivative 4 in the presence of pyridine in dichloromethane. $S_N2$ substitution with sodium azide provided azide 5 which subsequently underwent Staudinger reduction with triphenylphosphine to give amine 6. A second reductive amination yielded 7a and 7b, respectively. This three-step conversion from the tosylate 4 to amines 7a-b gave higher yields than the direct displacement with 4-methoxybenzylamine or 4-(methylthio)benzylamine. The free amino group was then protected with a Boc group and the resulted intermediates 8a-b were subsequently hydrolyzed under basic conditions to give acids 9a-b. HBTU-assisted amide coupling between 9a-b and corresponding amines followed by cleavage of the Boc protective group provided the final products (10-48). All target compounds were characterized by $^1H$ and $^{13}C$ NMR, MS and HPLC.

Scheme 1. Synthesis of compounds 10-48.

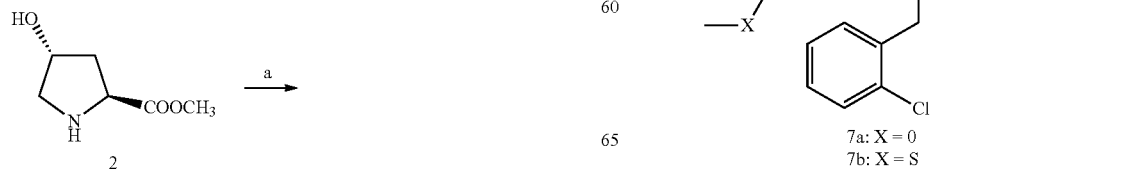

7a: X = O
7b: X = S

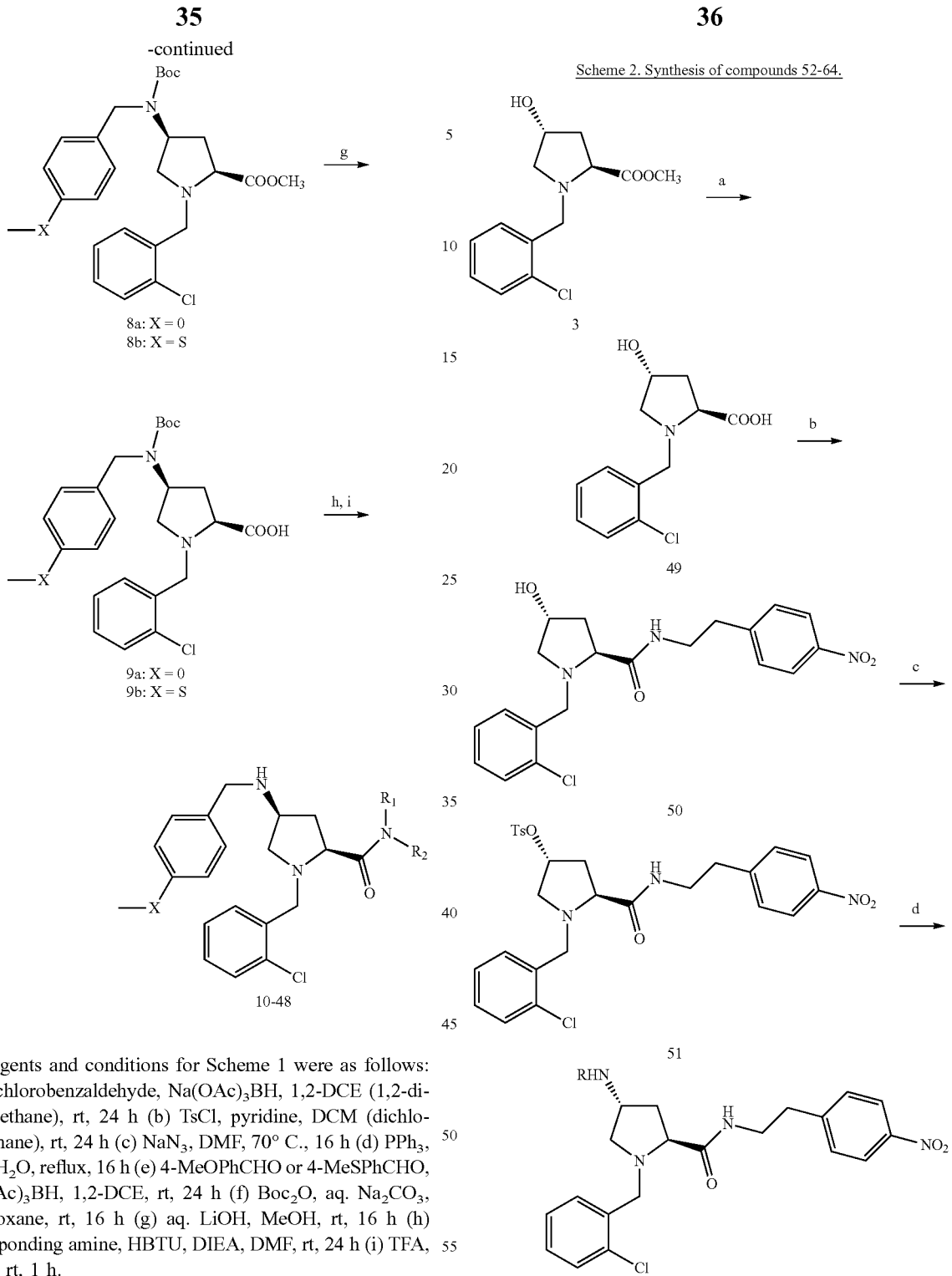

Reagents and conditions for Scheme 1 were as follows: (a) 2-chlorobenzaldehyde, Na(OAc)$_3$BH, 1,2-DCE (1,2-dichloroethane), rt, 24 h (b) TsCl, pyridine, DCM (dichloromethane), rt, 24 h (c) NaN$_3$, DMF, 70° C., 16 h (d) PPh$_3$, THF, H$_2$O, reflux, 16 h (e) 4-MeOPhCHO or 4-MeSPhCHO, Na(OAc)$_3$BH, 1,2-DCE, rt, 24 h (f) Boc$_2$O, aq. Na$_2$CO$_3$, 1,4-dioxane, rt, 16 h (g) aq. LiOH, MeOH, rt, 16 h (h) corresponding amine, HBTU, DIEA, DMF, rt, 24 h (i) TFA, DCM, rt, 1 h.

Compounds 52-654 were obtained via a slightly different route (Scheme 2). The ester 3 was hydrolyzed to give acid 49. HBTU-assisted amide coupling of 49 with 4-nitrophenylethylamine yielded the intermediate 50. 50 was converted to the tosylated derivative 51 before undergoing S$_N$2 displacement with corresponding amines to give the final products 52-64. The low yields of this S$_N$2 substitution were improved upon addition of more amine equivalents. However, the excess unreacted amines complicated the purification of the final product.

Reagents and conditions for Scheme 2 were as follows: (a) aq. LiOH, MeOH, rt, 16 h (b) 4-NO$_2$CH$_2$CH$_2$PhNH$_2$, HBTU, DIEA, DMF, rt, 24 h (c) TsCl, pyridine, DCM, rt, 24 h (d) corresponding amine, Et$_3$N, THF, reflux, 24 h.

Scheme 3 illustrates the synthesis of compounds 74-88. Trans-4-hydroxy-L-proline methyl ester (5) was N-Boc protected as the intermediate 65 and converted to 4-tosyl derivative 66 which underwent S$_N$2 displacement with sodium azide (67) and Staudinger reduction to provide the intermediate 68. Reductive amination with 4-methoxybenzaldehyde by sodium triacetoxyboron hydride give the secondary amine 69 which was subsequently protected with an N-Troc protective group as the intermediate 70. Hydrolysis of the methyl ester (71) followed by HBTU-assisted amide coupling with phenethylamine led to intermediate 72. Removal of the N-Boc group by TFA yielded the intermediate 73, which was used to prepare a series of analogs at the region 3. These analogs (74-88) were attained by reductive amination of 73 with corresponding aldehydes and removal of the N-Troc group by Zn in the presence of acetic acid in methanol under reflux.

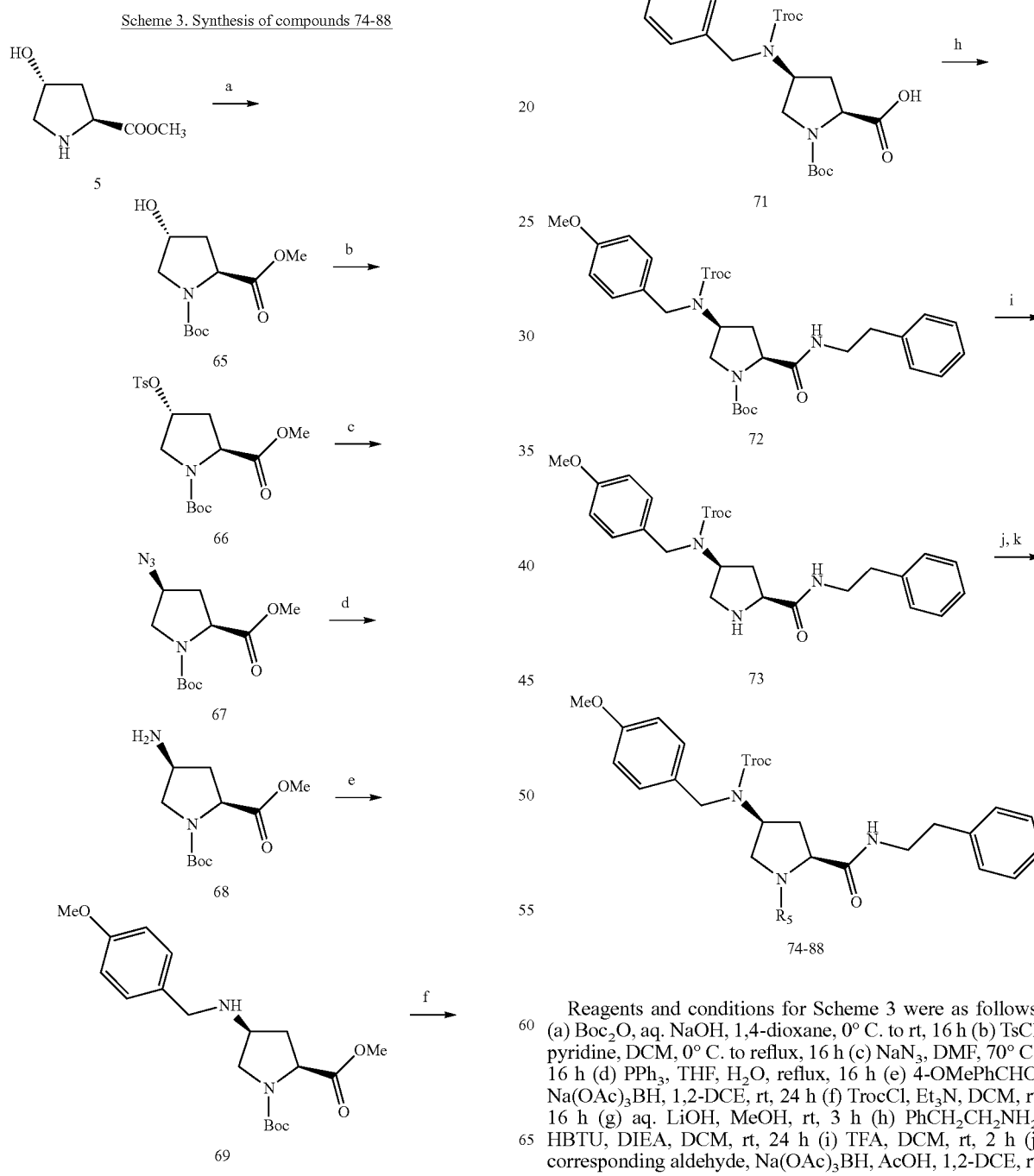

Scheme 3. Synthesis of compounds 74-88

Reagents and conditions for Scheme 3 were as follows: (a) Boc$_2$O, aq. NaOH, 1,4-dioxane, 0° C. to rt, 16 h (b) TsCl, pyridine, DCM, 0° C. to reflux, 16 h (c) NaN$_3$, DMF, 70° C., 16 h (d) PPh$_3$, THF, H$_2$O, reflux, 16 h (e) 4-OMePhCHO, Na(OAc)$_3$BH, 1,2-DCE, rt, 24 h (f) TrocCl, Et$_3$N, DCM, rt, 16 h (g) aq. LiOH, MeOH, rt, 3 h (h) PhCH$_2$CH$_2$NH$_2$, HBTU, DIEA, DCM, rt, 24 h (i) TFA, DCM, rt, 2 h (j) corresponding aldehyde, Na(OAc)$_3$BH, AcOH, 1,2-DCE, rt, 48 h (k) Zn, AcOH, MeOH, reflux, 1 h.

Experimental Section

Chemistry. All solvents and chemicals were reagent grade. Unless otherwise mentioned, all reagents and solvents were purchased from commercial vendors and used as received. Flash column chromatography was carried out on a Teledyne ISCO CombiFlash Rf system using prepacked columns. Solvents used include hexane, ethyl acetate (EtOAc), dichloromethane, methanol, and chloroform/methanol/ammonium hydroxide (80:18:2) (CMA-80). Purity and characterization of compounds were established by a combination of HPLC, TLC, mass spectrometry, and NMR analyses. $^1$H and $^{13}$C NMR spectra were recorded on a Bruker Avance DPX-300 (300 MHz) spectrometer and were determined in $CDCl_3$, DMSO-d6, or $CD_3OD$ with tetramethylsilane (TMS) (0.00 ppm) or solvent peaks as the internal reference. Chemical shifts are reported in ppm relative to the reference signal, and coupling constant (J) values are reported in hertz (Hz). Thin layer chromatography (TLC) was performed on EMD precoated silica gel 60 F254 plates, and spots were visualized with UV light or iodine staining. Low resolution mass spectra were obtained using a Waters Alliance HT/Micromass ZQ system (ESI). All test compounds were greater than 95% pure as determined by HPLC on an Agilent 1100 system using an Agilent Zorbax SB-Phenyl, 2.1 mm×150 mm, 5 m, column with gradient elution using the mobile phases (A) $H_2O$ containing 0.1% $CF_3COOH$ and (B) MeCN, with a flow rate of 1.0 mL/min.

Methyl (2S,4R)-1-[(2-chlorophenyl)methyl]-4-hydroxy-pyrrolidine-2-carboxylate (3). To a solution of methyl trans-4-hydroxy-L-proline (16.5 mmol, 3.00 g) and 2-chlorobenzaldehyde (21.5 mmol, 2.1 ml) in 1,2-dichloroethane (55 ml) was added acetic acid (0.9 ml) and sodium triacetoxyborohydride (24.8 mmol, 5.26 g). The reaction was stirred at room temperature for 24 h. After quenching with saturated solution of sodium bicarbonate, the reaction mixture was extracted three times with dichloromethane. The combined organic layers were washed sequentially with water and brine, dried over anhydrous magnesium sulfate, filtered, and concentrated in vacuo. The residue was purified by column chromatography to give the desired product as yellow liquid (4.00 g, 90%). $^1$H NMR (300 MHz, $CDCl_3$) δ 7.44 (dd, J=1.98, 7.44 Hz, 1H), 7.34 (m, 1H), 7.20 (m, 2H), 4.43 (m, 1H), 3.92 (m, 2H), 3.63-3.74 (m, 4H), 3.35 (dd, J=5.56, 10.08 Hz, 1H), 2.52 (dd, J=3.58, 10.17 Hz, 1H), 2.24 (m, 1H), 2.12 (m, 1H). MS (ESI) $[M]^+$ 270.2.

Methyl (2S,4R)-1-[(2-chlorophenyl)methyl]-4-[(4-methylbenzenesulfonyl)oxy]pyrrolidine-2-carboxylate (4). To a solution of 13821-125 (14.8 mmol, 4.00 g) in pyridine (11.4 ml) and anhydrous dichloromethane (11.4 ml) at 0° C. was added dropwise tosyl chloride (17.8 mmol, 3.39 g). The reaction was refluxed for 24 h. After removal of the solvent in vacuo, the residue was dissolved in dichloromethane and washed with saturated copper sulfate, water, and brine. The combined organic layers were dried over anhydrous magnesium sulfate, filtered, and concentrated in vacuo. The residue was purified by column chromatography (silica gel, ethyl acetate/hexanes) to provide the desired product as colorless liquid (3.77 g, 60%). $^1$H NMR (300 MHz, $CDCl_3$) δ 7.74-7.79 (m, 2H), 7.37-7.46 (m, 1H), 7.28-7.35 (m, 3H), 7.17-7.23 (m, 2H), 5.01 (d, J=5.46 Hz, 1H), 3.74-4.04 (m, 2H), 3.69 (s, 1H), 3.66 (s, 3H), 3.29 (dd, J=6.03, 11.11 Hz, 1H), 2.67-2.73 (m, 1H), 2.44 (s, 3H), 2.28 (dd, J=5.46, 7.54 Hz, 2H). MS (ESI) $[M]^+$ 424.2.

Methyl (2S,4S)-4-azido-1-[(2-chlorophenyl)methyl]pyrrolidine-2-carboxylate (5). To a solution of 4 (6.87 mmol, 2.91 g) in DMF (40 ml) was added sodium azide (13.74 mmol, 0.89 g). After stirring at 65° C. for 16 h, the reaction mixture was diluted with water, and extracted three times with ethyl acetate. The combined organic layers were dried over anhydrous magnesium sulfate, filtered, and concentrated in vacuo. The residue was purified by column chromatography ($SiO_2$, hexanes/ethyl acetate) to give the desired product as yellow liquid (1.47 g, 73%). $^1$H NMR (300 MHz, $CDCl_3$) δ 7.54 (dd, J=1.70, 7.54 Hz, 1H), 7.34 (dd, J=1.51, 7.72 Hz, 1H), 7.16-7.29 (m, 2H), 4.02-4.09 (m, 1H), 3.90-3.98 (m, 1H), 3.81-3.87 (m, 1H), 3.72 (s, 3H), 3.45 (dd, J=6.03, 9.23 Hz, 1H), 3.13 (dd, J=1.51, 10.36 Hz, 1H), 2.71 (dd, J=5.75, 10.27 Hz, 1H), 2.54 (ddd, J=7.72, 9.23, 14.13 Hz, 1H), 2.12-2.21 (m, J=0.90, 3.20, 6.10, 14.10 Hz, 1H) MS (ESI) $[M]^+$ 295.1.

Methyl (2S,4S)-4-amino-1-[(2-chlorophenyl)methyl]pyrrolidine-2-carboxylate (6). To a solution of azide 5 (4.3 mmol, 1.27 g) in THF (19 ml) under nitrogen was added $PPh_3$ (8.6 mmol, 2.26 g) and water (0.2 ml). The reaction mixture was refluxed with stirring for 6 h. After the solvent was removed, the residue was dissolved in diethyl ether, treated with 0.1N HCl for 5 min, and then extracted twice with diethyl ether. The aqueous layer was then treated with 1N NaOH until pH 10, and then extracted with dichloromethane. The combined dichloromethane fractions were dried over anhydrous $MgSO_4$, concentrated in vacuo to afford the desired product as yellow liquid (1 g, 86%). $^1$H NMR (300 MHz, $CDCl_3$) δ 7.50 (dd, J=1.9, 7.54 Hz, 1H), 7.33 (m, 1H), 7.16-7.20 (m, 2H), 3.95 (d, J=14.7 Hz, 1H), 3.81 (d, J=13.9 Hz, 1H), 3.66 (s, 3H), 3.45 (m, 1H), 3.39 (dd, J=5.5, 9.6 Hz, 1H), 2.85 (m, 1H), 2.68 (dd, J=5.5, 9.4 Hz, 1H), 2.48 (m, 1H), 1.79 (m, 1H), 1.74 (br, 2H). MS (ESI) $[M+H]^+$: 269.3.

Methyl (2S,4S)-1-[(2-chlorophenyl)methyl]-4-{[(4-methoxyphenyl)methyl]amino}pyrrolidine-2-carboxylate (7a). To a solution of amine 6 (3.72 mmol, 1 g) in 1,2-dichloroethane (12.4 ml) was added 4-methoxybenzaldehyde (3.72 mmol, 0.45 ml), sodium triacetoxyborohydride (5.58 mmol, 1.18 g) and glacial acetic acid (3.72 mmol, 0.21 ml). After stirring at room temperature for 16 h, the reaction was quenched with saturated sodium bicarbonate, extracted three times with dichloromethane. The combined organic layers were dried over anhydrous magnesium sulfate, filtered, and concentrated in vacuo. The residue was purified by column chromatography ($SiO_2$, dichloromethane/methanol) to give the desired product as colorless liquid (0.68 g, 47%). $^1$H NMR (300 MHz, $CDCl_3$) δ 7.49 (dd, J=1.79, 7.44 Hz, 1H), 7.33 (m, 1H), 7.16-7.25 (m, 4H), 6.84 (m, 2H), 3.95 (d, J=14.30 Hz, 1H), 3.78-3.84 (m, 4H), 3.67 (d, J=3.20 Hz, 5H), 3.39 (dd, J=6.03, 9.04 Hz, 1H), 3.28 (m, 1H), 3.03 (dd, J=2.54, 9.51 Hz, 1H), 2.61 (dd, J=6.12, 9.51 Hz, 1H), 2.40 (m, 1H), 1.93 (m, 1H). MS (ESI) $[M+H]^+$ 389.4.

Methyl (2S,4S)-1-[(2-chlorophenyl)methyl]-4-{[(4-(methylsulfanyl)phenyl)methyl]amino}pyrrolidine-2-carboxylate (7b) was synthesized from 6 and 4-(methylthio)benzaldehyde according to the procedure for the synthesis of 7a as yellow liquid (450% yield). $^1$H NMR (300 MHz, $CDCl_3$) δ 7.42 (br. s., OH), 7.32 (d, J=6.78 Hz, OH), 7.13-7.24 (m, 6H), 3.90 (d, J=7.91 Hz, 1H), 3.66 (s, 3H), 3.64 (br. s., 1H), 3.22-3.30 (m, 1H), 2.87-2.97 (m, 1H), 2.47-2.50 (m, 2H), 2.46 (s, 3H), 2.02-2.12 (m, 1H). MS (ESI) $[M+H]^+$ 405.3.

Methyl (2S,4S)-4-{[(tert-butoxy)carbonyl][(4-methoxyphenyl)methyl]amino}-1-[(2-chlorophenyl)methyl]pyrrolidine-2-carboxylate (8a). To a solution of amine 7 (1.75 mmol, 0.68 g) in 1,4-dioxane (10 ml) was added 10% w/v $Na_2CO_3$ solution (2 ml) and $Boc_2O$ (1.92 mmol, 0.42 g). After stirring at room temperature after 16 h, 1,4-dioxane was removed under reduced pressure. The remaining aqueous solution was extracted three times with dichloromethane. The combined organic layers were dried over anhydrous MgSO$_4$, filtered, and concentrated in vacuo and the crude was used for the next step without further purification. $^1$H NMR (300 MHz, CDCl$_3$) δ 7.30-7.38 (m, 2H), 7.16-7.22 (m, 2H), 7.06 (d, J=8.67 Hz, 2H), 6.80 (d, J=8.67 Hz, 2H), 4.47-4.63 (m, 1H), 4.26-4.44 (m, 2H), 3.83 (d, J=6.97 Hz, 2H), 3.78 (s, 3H), 3.65 (s, 3H), 3.61 (d, J=6.97 Hz, 1H), 3.06 (t, J=8.29 Hz, 1H), 2.67 (dd, J=7.44, 8.95 Hz, 1H), 2.13-2.25 (m, 2H), 1.53 (s, 9H). MS (ESI) [M]$^+$ 489.6.

Methyl (2S,4S)-4-{[(tert-butoxy)carbonyl][(4-(methylsulfanyl)phenyl)methyl]amino}-1-[(2-chlorophenyl)methyl]pyrrolidine-2-carboxylate (8b) was synthesized from 7b according to the procedure for the synthesis of 8a as yellow liquid (quant. yield). $^1$H NMR (300 MHz, CDCl$_3$) δ 7.34 (d, J=6.22 Hz, 1H), 7.26-7.32 (m, 1H), 7.08-7.19 (m, 4H), 7.01-7.06 (m, 2H), 4.79-5.03 (m, 1H), 4.58 (s, 2H), 3.91 (d, J=13.75 Hz, 1H), 3.64 (s, 3H), 3.58 (d, J=13.94 Hz, 1H), 3.27 (t, J=8.29 Hz, 1H), 2.87-2.96 (m, 1H), 2.49-2.60 (m, 2H), 2.45 (s, 3H), 1.87-1.99 (m, 1H), 1.34 (s, 9H). MS (ESI) [M]$^+$ 505.6.

(2S,4S)-4-{[(tert-butoxy)carbonyl][(4-methoxyphenyl)methyl]amino}-1-[(2-chlorophenyl)methyl]pyrrolidine-2-carboxylic acid (9a) To a solution of ester 8 (1.75 mmol, 0.86 g) in methanol (16 ml) and water (16 ml) was added LiOH (8.75 mmol, 0.21 g). After stirring at room temperature for 3 h, methanol was removed under reduced pressure. The remaining solution was diluted in water and acidified with 1N HCl to pH 5. The mixture was then extracted with ethyl acetate. The combined organic layers were washed with water and brine, dried over anhydrous MgSO$_4$, filtered, and concentrated in vacuo to provide the desired product as white solid (0.83 g, quantitative yield). $^1$H NMR (300 MHz, CDCl$_3$) δ 7.35 (d, J=8.10 Hz, 2H), 7.17-7.24 (m, 2H), 7.02 (d, J=8.48 Hz, 2H), 6.77 (d, J=8.48 Hz, 2H), 4.26-4.55 (m, 3H), 4.06-4.17 (m, 1H), 3.71-3.82 (m, 4H), 3.40-3.52 (m, 1H), 3.08 (d, J=6.40 Hz, 1H), 2.70-2.82 (m, 1H), 2.44-2.58 (m, 1H), 2.07-2.17 (m, 1H), 1.40 (s, 9H). MS (ESI) [M]$^+$ 475.7, [M–H]$^-$ 473.8.

(2S,4S)-4-{[(tert-butoxy)carbonyl][(4-(methylsulfanyl)phenyl)methyl]amino}-1-[(2-chlorophenyl)methyl]pyrrolidine-2-carboxylic acid (9b) was synthesized from 8b according to the procedure for the synthesis of 9a as white solid (quant. yield). $^1$H NMR (300 MHz, CDCl$_3$) δ 7.42 (br. s., 1H), 7.34 (d, J=7.72 Hz, 1H), 7.16-7.26 (m, 2H), 7.13 (d, J=8.10 Hz, 2H), 7.02 (d, J=8.10 Hz, 2H), 4.47-4.61 (m, 1H), 4.31-4.46 (m, 2H), 4.23 (d, J=10.93 Hz, 1H), 3.77-3.88 (m, 1H), 3.58 (d, J=10.74 Hz, 1H), 3.02-3.13 (m, 1H), 2.81 (d, J=10.36 Hz, 1H), 2.52-2.66 (m, 1H), 2.44 (s, 3H), 2.06-2.17 (m, 1H), 1.38 (s, 8H). MS (ESI) [M–H]$^-$ 489.5.

General procedure A: To a solution of acid 9 (0.2 mmol, 1 eq) in DMF (0.6 ml, 0.3 M) was added HBTU (0.22 mmol, 1.1 eq), corresponding amine (0.22 mmol, 1.1 eq), DIEA (0.66 mmol, 3 eq). After stirring at room temperature for 16 h, the reaction mixture was diluted with water, extracted three times with ethyl acetate. The combined organic fractions were dried over anhydrous magnesium sulfate and concentrated in vacuo. The residue was dissolved in 20% v/v trifluoroacetic acid (1 ml) in dichloromethane and stirred at room temperature for 16 h. The reaction mixture was concentrated under reduced pressure and the residue was purified on column chromatography (SiO$_2$, methanol/dichloromethane) to afford the desired product.

(2S,4S)-1-[(2-Chlorophenyl)methyl]-4-{[(4-methoxyphenyl)methyl]amino}-N-methylpyrrolidine-2-carboxamide (10) was prepared according to the general procedure A as yellow oil (9%). $^1$H NMR (300 MHz, CDCl$_3$) δ 7.43 (dd, J=1.79, 7.44 Hz, 1H), 7.28-7.34 (m, 2H), 7.12-7.25 (m, 3H), 6.87 (s, 2H), 3.90-3.96 (m, 2H), 3.75 (s, 3H), 3.58-3.69 (m, 2H), 3.28 (s, 2H), 3.09 (dd, J=4.14, 7.54 Hz, 1H), 2.68 (d, J=4.90 Hz, 3H), 2.43-2.59 (m, 1H), 2.03-2.14 (m, 2H). $^{13}$C NMR (75 MHz, CDCl$_3$) δ 173.3, 160.5, 134.4, 133.9, 131.4, 131.0, 129.6, 129.0, 127.1, 114.6, 66.2, 55.6, 55.2, 54.9, 54.8, 53.6, 42.0, 33.5, 11.8. MS (ESI) [M]$^+$ 388.3.

(2S,4S)-1-[(2-Chlorophenyl)methyl]-N-ethyl-4-{[(4-methoxyphenyl)methyl]amino}pyrrolidine-2-carboxamide (11) was prepared according to the general procedure A as yellow oil (32%). $^1$H NMR (300 MHz, CDCl$_3$) δ 7.41 (br. s., 1H), 7.30-7.38 (m, 2H), 7.14-7.25 (m, 4H), 6.84 (d, J=8.67 Hz, 1H), 3.83-3.91 (m, 1H), 3.79 (s, 3H), 3.58-3.73 (m, 3H), 3.33 (td, J=2.80, 5.89 Hz, 1H), 3.19-3.28 (m, 1H), 3.10-3.19 (m, 2H), 3.00 (d, J=9.98 Hz, 1H), 2.62 (dd, J=5.56, 10.08 Hz, 1H), 2.49 (ddd, J=6.40, 9.84, 13.70 Hz, 1H), 1.87-1.97 (m, 1H), 1.02 (t, J=14.70 Hz, 3H). $^{13}$C NMR (75 MHz, CDCl$_3$) δ 173.9, 158.9, 135.7, 134.3, 131.1, 129.7, 129.5, 128.9, 126.9, 113.9, 67.1, 59.5, 57.4, 56.2, 55.3, 51.1, 37.0, 33.7, 14.6. MS (ESI) [M]$^+$ 402.2.

(2S,4S)-1-[(2-Chlorophenyl)methyl]-4-{[(4-methoxyphenyl)methyl]amino}-N-propylpyrrolidine-2-carboxamide (12) was prepared according to the general procedure A as yellow oil (48%). $^1$H NMR (300 MHz, CDCl$_3$) δ 7.82 (t, J=5.27 Hz, 1H), 7.29-7.50 (m, 4H), 7.24 (d, J=8.67 Hz, 2H), 6.85 (d, J=8.67 Hz, 2H), 4.26-4.46 (m, 3H), 4.14 (d, J=13.00 Hz, 2H), 3.94-4.03 (m, 1H), 3.78 (s, 3H), 3.46 (d, J=5.09 Hz, 2H), 3.07-3.22 (m, 2H), 2.88-3.02 (m, 1H), 2.27-2.40 (m, 1H), 1.42-1.54 (m, 2H), 0.87 (t, J=7.44 Hz, 3H). $^{13}$C NMR (75 MHz, CDCl3) δ 174.0, 158.9, 135.7, 134.1, 131.0, 129.7, 129.6, 128.8, 126.9, 113.9, 67.1, 59.2, 57.2, 56.1, 55.3, 51.0, 40.7, 36.8, 22.7, 11.4. MS (ESI) [M]$^+$ 416.5.

(2S,4S)—N-Butyl-1-[(2-chlorophenyl)methyl]-4-{[(4-methoxyphenyl)methyl]amino}pyrrolidine-2-carboxamide (13) was prepared according to the general procedure A as yellow oil (12%). $^1$H NMR (300 MHz, CDCl$_3$) δ 7.74 (br. s., 1H), 7.47 (d, J=7.72 Hz, 1H), 7.39-7.45 (m, 2H), 7.34 (dd, J=2.07, 7.16 Hz, 1H), 7.24 (d, J=8.67 Hz, 2H), 6.87 (d, J=8.29 Hz, 2H), 4.34-4.56 (m, 3H), 4.19 (d, J=13.37 Hz, 2H), 3.99-4.07 (m, 1H), 3.78 (s, 3H), 3.56 (d, J=3.20 Hz, 2H), 3.13-3.27 (m, 2H), 2.94-3.08 (m, 1H), 2.33-2.46 (m, 1H), 1.38-1.50 (m, 2H), 1.29 (dd, J=6.97, 14.88 Hz, 2H), 0.90 (t, J=7.25 Hz, 3H). $^{13}$C NMR (75 MHz, CDCl$_3$) δ 173.2, 159.8, 135.1, 133.9, 130.8, 130.6, 129.6, 128.8, 127.0, 114.3, 66.7, 57.2, 55.8, 55.5, 55.2, 49.6, 39.0, 34.8, 31.4, 20.0, 13.6. MS (ESI) [M]$^+$ 430.1.

(2S,4S)—N-(Butan-2-yl)-1-[(2-chlorophenyl)methyl]-4-{[(4-methoxyphenyl)methyl]amino}pyrrolidine-2-carboxamide (14) was prepared according to the general procedure A as colorless oil (74%). $^1$H NMR (300 MHz, CDCl$_3$) δ 7.29-7.39 (m, 3H), 7.16-7.25 (m, 4H), 6.83 (d, J=8.67 Hz, 1H), 3.87-3.94 (m, 1H), 3.74-3.84 (m, 5H), 3.61-3.72 (m, 3H), 3.20-3.33 (m, 2H), 2.97 (td, J=1.62, 10.13 Hz, 1H), 2.60 (ddd, J=3.01, 5.60, 10.03 Hz, 1H), 2.45-2.54 (m, 1H), 1.87-1.96 (m, 1H), 1.76 (br. s., 1H), 1.29-1.39 (m, 2H), 1.02 (d, J=6.59 Hz, 2H), 0.94 (d, J=6.59 Hz, 2H), 0.74-0.85 (m, 5H). $^{13}$C NMR (75 MHz, CDCl3) δ 173.4, 173.4, 158.7, 158.7, 135.9, 134.3, 134.2, 131.9, 131.2, 130.9, 129.8, 129.8, 129.4, 128.9, 128.8, 126.9, 126.9, 113.8, 113.8, 67.3, 67.2, 59.7, 59.6, 57.7, 57.5, 56.2, 56.1, 55.3, 51.3, 46.0, 45.8, 37.4, 37.2, 29.6, 20.1, 10.5, 10.4. MS (ESI) [M]$^+$ 430.4.

(2S,4S)—N-tert-Butyl-1-[(2-chlorophenyl)methyl]-4-{[(4-methoxyphenyl)methyl]amino}pyrrolidine-2-carboxamide (15) was prepared according to the general procedure A as colorless oil (88%). $^1$H NMR (300 MHz, CDCl$_3$) δ 7.30-7.39 (m, 2H), 7.15-7.25 (m, 5H), 6.82-6.87 (m, 2H), 3.76-3.82 (m, 5H), 3.60-3.75 (m, 2H), 3.28-3.36 (m, 1H), 3.14 (dd, J=5.27, 9.80 Hz, 1H), 3.06 (d, J=10.17 Hz, 1H), 2.64 (dd, J=5.65, 9.98 Hz, 1H), 2.47 (ddd, J=6.40, 9.80, 13.56 Hz, 1H), 1.89 (td, J=3.67, 13.56 Hz, 1H), 1.18 (s, 9H). $^{13}$C NMR (75 MHz, CDCl3) δ 173.5, 158.8, 136.0, 134.8, 131.0, 129.7, 129.4, 128.9, 127.0, 113.9, 67.8, 59.9, 57.6, 56.2, 55.3, 51.2, 50.2, 37.2, 28.5. MS (ESI) [M]$^+$ 430.0.

(2S,4S)-1-[(2-Chlorophenyl)methyl]-4-{[(4-methoxyphenyl)methyl]amino}-N-pentylpyrrolidine-2-carboxamide (16) was prepared according to the general procedure A as yellow oil (25%). $^1$H NMR (300 MHz, CDCl$_3$) δ 7.32-7.43 (m, 3H), 7.17-7.24 (m, 4H), 6.81-6.86 (m, 2H), 3.84-3.91 (m, 1H), 3.78 (s, 3H), 3.64-3.74 (m, 3H), 3.31-3.38 (m, 1H), 3.25 (dd, J=5.65, 9.80 Hz, 1H), 2.99-3.16 (m, 3H), 2.61 (dd, J=5.56, 10.27 Hz, 1H), 2.48 (dd, J=2.83, 6.78 Hz, 1H), 1.92 (d, J=18.08 Hz, 1H), 1.31-1.43 (m, 2H), 1.16-1.30 (m, 4H), 0.84 (t, J=6.97 Hz, 3H). $^{13}$C NMR (75 MHz, CDCl3) δ 173.9, 158.9, 135.7, 134.1, 130.9, 129.7, 129.6, 128.8, 126.9, 113.9, 67.1, 59.2, 57.2, 56.1, 55.3, 51.0, 38.9, 36.8, 29.1, 29.1, 22.3, 13.9. MS (ESI) [M]$^+$ 444.4.

(2S,4S)-1-[(2-Chlorophenyl)methyl]-4-{[(4-methoxyphenyl)methyl]amino}-N-(3-methylbutyl)pyrrolidine-2-carboxamide (17) was prepared according to the general procedure A as colorless oil (71%). $^1$H NMR (300 MHz, CDCl$_3$) δ 7.23-7.34 (m, 3H), 7.10-7.18 (m, 4H), 6.76 (d, J=8.67 Hz, 2H), 3.77-3.83 (m, 1H), 3.71 (s, 3H), 3.57-3.67 (m, 3H), 3.27 (td, J=2.87, 5.93 Hz, 1H), 3.17 (dd, J=5.46, 9.80 Hz, 1H), 3.05 (dt, J=7.72, 12.90 Hz, 2H), 2.92-2.98 (m, 1H), 2.54 (dd, J=5.65, 10.17 Hz, 1H), 2.42 (ddd, J=6.59, 9.80, 13.75 Hz, 1H), 1.80-1.89 (m, 1H), 1.44 (td, J=6.69, 13.37 Hz, 1H), 1.16-1.23 (m, 2H), 0.77 (dd, J=3.39, 6.59 Hz, 6H). $^{13}$C NMR (75 MHz, CDCl3) δ 172.9, 157.9, 134.7, 133.1, 130.0, 128.7, 128.6, 127.8, 125.9, 112.9, 66.1, 58.2, 56.2, 55.1, 54.2, 49.9, 37.3, 36.2, 35.8, 24.8, 21.4. MS (ESI) [M]$^+$ 444.7.

(2S,4S)-1-[(2-Chlorophenyl)methyl]-4-{[(4-methoxyphenyl)methyl]amino}-N-hexylpyrrolidine-2-carboxamide (18) was prepared according to the general procedure A as colorless oil (49%). $^1$H NMR (300 MHz, CDCl$_3$) δ 7.45 (t, J=5.65 Hz, 1H), 7.31-7.38 (m, 2H), 7.16-7.24 (m, 4H), 6.81-6.85 (m, 2H), 3.84-3.91 (m, 1H), 3.79 (s, 3H), 3.58-3.72 (m, 3H), 3.31 (td, J=2.76, 5.98 Hz, 1H), 3.25 (dd, J=5.56, 9.89 Hz, 1H), 3.11 (dt, J=7.06, 12.86 Hz, 2H), 3.00 (d, J=10.17 Hz, 1H), 2.60 (dd, J=5.56, 10.08 Hz, 1H), 2.49 (ddd, J=6.50, 9.84, 13.61 Hz, 1H), 1.90 (td, J=3.84, 13.61 Hz, 2H), 1.31-1.41 (m, 2H), 1.17-1.29 (m, 6H), 0.85 (t, J=13.40 Hz, 3H). $^{13}$C NMR (75 MHz, CDCl$_3$) δ 174.0, 158.8, 135.8, 134.2, 131.8, 131.0, 129.7, 129.4, 128.8, 126.9, 113.9, 67.2, 59.6, 57.4, 56.2, 55.2, 51.2, 38.9, 37.2, 31.5, 29.4, 26.6, 22.5, 14.0. MS (ESI) [M]$^+$ 458.0.

(2S,4S)-1-[(2-Chlorophenyl)methyl]-N-decyl-4-{[(4-methoxyphenyl)methyl]amino}pyrrolidine-2-carboxamide (19) was prepared according to the general procedure A as colorless oil (58%). $^1$H NMR (300 MHz, CDCl$_3$) δ 7.42 (t, J=5.75 Hz, 1H), 7.33-7.37 (m, 2H), 7.16-7.25 (m, 5H), 6.83 (d, J=8.67 Hz, 1H), 3.84-3.91 (m, 1H), 3.78 (s, 3H), 3.62-3.75 (m, 4H), 3.33-3.40 (m, 1H), 3.25 (dd, J=5.65, 9.61 Hz, 1H), 2.90-3.16 (m, 6H), 2.61 (dd, J=5.65, 10.17 Hz, 1H), 2.49 (ddd, J=6.59, 9.61, 13.75 Hz, 1H), 1.89-1.97 (m, 1H), 1.16-1.42 (m, 18H), 0.85-0.90 (m, 3H). $^{13}$C NMR (75 MHz, CDCl$_3$) δ 173.9, 159.0, 135.7, 134.1, 130.9, 129.7, 129.7, 128.8, 127.0, 114.0, 67.1, 59.1, 57.1, 56.1, 55.3, 50.9, 39.0, 36.7, 31.9, 29.6, 29.5, 29.5, 29.3, 27.0, 22.7, 14.1. MS (ESI) [M]$^+$ 514.8.

(2S,4S)-1-[(2-Chlorophenyl)methyl]-4-{[(4-methoxyphenyl)methyl]amino}-N-[2-(morpholin-4-yl)ethyl]pyrrolidine-2-carboxamide (20) was prepared according to the general procedure A as colorless oil (18%). $^1$H NMR (300 MHz, CDCl$_3$) δ 7.52 (t, J=5.27 Hz, 1H), 7.34-7.38 (m, 2H), 7.18-7.25 (m, 4H), 6.84 (d, J=8.67 Hz, 2H), 3.84-3.91 (m, 1H), 3.74-3.78 (m, 4H), 3.68-3.73 (m, 4H), 3.59-3.65 (m, 4H), 3.42 (t, J=7.72 Hz, 1H), 3.22-3.37 (m, 4H), 2.35-2.45 (m, 7H), 2.13-2.21 (m, J=1.00, 1.00 Hz, 2H). $^{13}$C NMR (75 MHz, CDCl$_3$) δ 173.5, 159.2, 135.6, 134.2, 130.9, 129.8, 129.7, 128.9, 126.9, 114.0, 66.8, 66.4, 57.4, 57.3, 55.4, 55.2, 53.4, 51.4, 36.7, 35.3, 30.9. MS (ESI) [M]$^+$ 487.6.

(2S,4S)-1-[(2-Chlorophenyl)methyl]-N-(2-cyclohexylethyl)-4-{[(4-methoxyphenyl)methyl]amino}pyrrolidine-2-carboxamide (21) was prepared according to the general procedure A as colorless oil (53%). $^1$H NMR (300 MHz, CDCl$_3$) δ 7.32-7.41 (m, 3H), 7.15-7.25 (m, 4H), 6.84 (d, J=8.67 Hz, 2H), 3.83-3.90 (m, 1H), 3.79 (s, 3H), 3.59-3.73 (m, 3H), 3.32 (td, J=2.80, 5.89 Hz, 1H), 3.25 (dd, J=5.56, 9.70 Hz, 1H), 3.08-3.19 (m, 2H), 3.02 (d, J=10.17 Hz, 1H), 2.60 (dd, J=5.65, 9.98 Hz, 1H), 2.49 (ddd, J=6.50, 9.80, 13.66 Hz, 1H), 1.86-1.95 (m, 1H), 1.56-1.70 (m, 5H), 1.08-1.30 (m, 6H), 0.76-0.93 (m, 2H). $^{13}$C NMR (75 MHz, CDCl$_3$) δ 173.9, 158.8, 135.8, 134.1, 130.9, 129.7, 129.5, 128.8, 126.9, 113.9, 67.2, 59.4, 57.3, 56.2, 55.2, 51.1, 37.0, 36.8, 36.7, 35.3, 33.1, 33.1, 30.9, 26.5, 26.2. MS (ESI) [M]$^+$ 484.4.

(2S,4S)-1-[(2-Chlorophenyl)methyl]-N,N-diethyl-4-{[(4-methoxyphenyl)methyl]amino}pyrrolidine-2-carboxamide (22) was prepared according to the general procedure A as colorless oil (11%). $^1$H NMR (300 MHz, CDCl$_3$) δ 7.78 (br. s., 1H), 7.46 (dd, J=2.26, 6.97 Hz, 1H), 7.33-7.38 (m, 1H), 7.16-7.25 (m, 4H), 6.80-6.88 (m, 2H), 3.83-3.91 (m, 1H), 3.79 (s, 3H), 3.64-3.76 (m, 3H), 3.16-3.36 (m, 4H), 3.03 (d, J=9.61 Hz, 1H), 2.43-2.61 (m, 7H), 1.79-2.05 (m, 3H), 0.96 (t, J=7.06 Hz, 6H). $^{13}$C NMR (75 MHz, CDCl$_3$) δ 174.2, 158.8, 135.8, 134.0, 130.8, 129.5, 129.4, 128.6, 126.9, 113.9, 67.2, 56.8, 56.1, 55.3, 51.5, 51.2, 46.6, 37.3, 36.2, 11.1. MS (ESI) [M]$^+$ 473.5.

(2S,4S)—N-Benzyl-1-[(2-chlorophenyl)methyl]-4-{[(4-methoxyphenyl)methyl]amino}pyrrolidine-2-carboxamide (23) was prepared according to the general procedure A as yellow oil (44%). $^1$H NMR (300 MHz, CDCl$_3$) δ 7.82 (t, J=5.75 Hz, 1H), 7.22-7.27 (m, 5H), 7.10-7.21 (m, 6H), 6.77-6.83 (m, 2H), 4.32 (dd, J=5.93, 8.95 Hz, 2H), 3.87 (d, J=13.19 Hz, 1H), 3.77 (s, 3H), 3.58-3.71 (m, 3H), 3.34-3.41 (m, 1H), 3.31 (dd, J=5.56, 9.70 Hz, 1H), 2.98 (d, J=10.36 Hz, 1H), 2.60 (dd, J=5.46, 10.36 Hz, 1H), 2.49 (ddd, J=6.78, 9.70, 13.85 Hz, 1H), 1.92-2.02 (m, 1H). $^{13}$C NMR (75 MHz, CDCl$_3$) δ 173.9, 159.1, 138.3, 135.4, 134.1, 131.0, 129.7, 129.7, 128.8, 128.6, 127.8, 127.3, 126.9, 114.0, 67.0, 58.7, 56.9, 56.0, 55.3, 50.7, 43.1, 36.3. MS (ESI) [M]$^+$ 464.4.

(2S,4S)-1-[(2-Chlorophenyl)methyl]-4-{[(4-methoxyphenyl)methyl]amino}-N-(2-phenylethyl)pyrrolidine-2-carboxamide (24) was prepared according to the general procedure A as yellow oil (59%). $^1$H NMR (300 MHz, CDCl$_3$) δ 7.52 (t, J=5.84 Hz, 1H), 7.32-7.37 (m, 1H), 7.09-7.24 (m, 11H), 6.83 (d, J=8.67 Hz, 1H), 3.73-3.81 (m, 4H), 3.63-3.67 (m, 1H), 3.56-3.62 (m, 2H), 3.43-3.55 (m, 1H), 3.30-3.42 (m, 1H), 3.19-3.28 (m, 2H), 2.92 (d, J=10.17 Hz, 1H), 2.67-2.76 (m, 2H), 2.42-2.55 (m, 2H), 1.96 (br. s., 1H), 1.81 (m, 1H). $^{13}$C NMR (75 MHz, CDCl$_3$) δ 174.1, 158.7, 138.9, 135.8, 134.1, 132.0, 130.7, 129.6, 129.4, 128.7, 128.6, 128.5, 126.9, 126.4, 113.9, 67.3, 59.5, 57.2, 56.0, 55.3, 51.2, 39.8, 37.3, 35.5. MS (ESI) [M]$^+$ 478.4.

(2S,4S)-1-[(2-Chlorophenyl)methyl]-4-{[(4-methoxyphenyl)methyl]amino}-N-(3-phenylpropyl)pyrrolidine-2-carboxamide (25) was prepared according to the general procedure A as colorless oil (70%). $^1$H NMR (300 MHz, CDCl$_3$) δ 7.44 (t, J=5.37 Hz, 1H), 7.13-7.36 (m, 10H), 7.09 (d, J=6.78 Hz, 1H), 6.80 (d, J=8.67 Hz, 2H), 3.83-3.90 (m, 1H), 3.75 (s, 3H), 3.66-3.73 (m, 3H), 3.34-3.41 (m, 1H), 3.25 (dd, J=5.56, 9.70 Hz, 1H), 3.11-3.20 (m, 2H), 3.05 (d, J=10.55 Hz, 1H), 2.43-2.64 (m, 4H), 1.96 (d, J=3.20 Hz, 1H), 1.65-1.77 (m, 2H). $^{13}$C NMR (75 MHz, CDCl$_3$) δ 173.9, 159.1, 141.5, 135.6, 134.1, 130.9, 129.8, 129.7, 128.9, 128.4, 128.3, 127.0, 125.9, 114.0, 67.0, 58.9, 56.9, 56.0, 55.2, 50.8, 38.6, 36.5, 33.2, 31.1. MS (ESI) [M]$^+$ 492.7.

(2S,4S)-1-[(2-Chlorophenyl)methyl]-N-[2-(4-methoxyphenyl)ethyl]-4-{[(4-methoxyphenyl)methyl]amino}pyrrolidine-2-carboxamide (26) was prepared according to the general procedure A as colorless oil (20%). $^1$H NMR (300 MHz, CDCl$_3$) δ 7.40 (t, J=5.65 Hz, 1H), 7.32-7.36 (m, 1H), 7.15-7.22 (m, 4H), 7.10-7.14 (m, 1H), 7.05 (d, J=8.67 Hz, 2H), 6.85 (d, J=8.67 Hz, 2H), 6.77 (d, J=8.48 Hz, 2H), 3.78 (s, 3H), 3.75 (s, 3H), 3.70-3.73 (m, 1H), 3.65 (d, J=9.04 Hz, 2H), 3.42-3.52 (m, 1H), 3.37 (dd, J=5.65, 9.61 Hz, 1H), 3.23-3.32 (m, 1H), 3.10-3.22 (m, 2H), 2.67 (dt, J=3.30, 7.02 Hz, 2H), 2.25 (t, J=8.01 Hz, 1H), 2.01-2.16 (m, 2H), 1.40-1.68 (m, 2H). $^{13}$C NMR (75 MHz, CDCl$_3$) δ 173.8, 158.8, 158.2, 135.7, 134.2, 132.1, 131.0, 130.9, 129.6, 129.6, 129.2, 128.8, 126.9, 114.0, 113.9, 66.7, 60.1, 57.8, 56.1, 55.3, 55.2, 52.1, 40.0, 37.9, 34.8, 30.9. MS (ESI) [M]$^+$ 508.6.

(2S,4S)—N-[2-(4-Chlorophenyl)ethyl]-1-[(2-chlorophenyl)methyl]-4-{[(4-methoxyphenyl)methyl]amino}pyrrolidine-2-carboxamide (27) was prepared according to the general procedure A as colorless oil (55%). $^1$H NMR (300 MHz, CDCl$_3$) δ 7.46 (t, J=5.93 Hz, 1H), 7.27-7.31 (m, 1H), 7.08-7.25 (m, 7H), 7.00-7.04 (m, 2H), 6.81-6.86 (m, 2H), 3.75-3.80 (m, OH), 3.73 (s, 3H), 3.68 (d, J=13.19 Hz, 2H), 3.53-3.60 (m, 1H), 3.31-3.50 (m, 3H), 3.18 (dd, J=6.78, 9.04 Hz, 1H), 3.08 (d, J=10.93 Hz, 1H), 2.69 (q, J=7.03 Hz, 2H), 2.42-2.55 (m, 2H), 1.92 (dt, J=3.20, 7.06 Hz, 1H). $^{13}$C NMR (75 MHz, CDCl$_3$) δ 173.1, 159.8, 137.2, 134.9, 133.7, 132.1, 130.6, 130.2, 130.0, 129.6, 128.7, 128.5, 126.9, 114.3, 67.1, 57.3, 55.8, 55.2, 55.2, 49.7, 39.7, 34.9, 34.7. MS (ESI) [M]$^+$ 512.4.

(2S,4S)-1-[(2-Chlorophenyl)methyl]-N-[2-(3,4-dimethoxyphenyl)ethyl]-4-{[(4-methoxyphenyl)methyl]amino}pyrrolidine-2-carboxamide (28) was prepared according to the general procedure A as white solid (61%). $^1$H NMR (300 MHz, CDCl$_3$) δ 7.29-7.35 (m, 1H), 7.18-7.25 (m, 3H), 7.09-7.15 (m, 2H), 6.82 (d, J=8.67 Hz, 2H), 6.68 (s, 3H), 3.63-3.88 (m, 13H), 3.45-3.60 (m, 3H), 3.28-3.41 (m, 1H), 3.12-3.20 (m, 2H), 2.70 (qd, J=7.21, 14.93 Hz, 2H), 2.43-2.58 (m, 2H), 1.99 (ddd, J=3.49, 6.26, 13.99 Hz, 1H). $^{13}$C NMR (75 MHz, CDCl$_3$) δ 172.6, 160.3, 148.9, 147.6, 134.6, 133.6, 131.2, 131.1, 130.4, 129.5, 128.7, 126.9, 120.6, 114.5, 111.8, 111.1, 66.8, 56.0, 55.8, 55.2, 55.0, 54.9, 48.9, 40.1, 34.8, 33.8. MS (ESI) [M]$^+$ 538.4.

(2S,4S)-1-[(2-Chlorophenyl)methyl]-N-{2-[4-(dimethylamino)phenyl]ethyl}-4-{[(4-methoxyphenyl)methyl]amino}pyrrolidine-2-carboxamide (29) was prepared according to the general procedure A as yellow oil (25%). $^1$H NMR (300 MHz, CDCl$_3$) δ 7.30-7.34 (m, 1H), 7.15-7.25 (m, 5H), 6.98 (d, J=8.67 Hz, 2H), 6.84 (d, J=8.67 Hz, 2H), 6.59 (d, J=8.48 Hz, 2H), 3.62-3.81 (m, 7H), 3.33-3.45 (m, 3H), 3.20 (dd, J=5.46, 9.42 Hz, 1H), 3.05 (d, J=10.36 Hz, 1H), 2.86 (s, 6H), 2.53-2.69 (m, 3H), 2.40-2.51 (m, 1H), 1.91 (d, J=13.56 Hz, 1H). $^{13}$C NMR (75 MHz, CDCl$_3$) δ 173.7, 159.3, 149.4, 135.4, 133.9, 130.8, 130.1, 129.5, 129.2, 128.6, 126.9, 126.5, 114.1, 112.9, 66.8, 58.2, 56.1, 55.8, 55.3, 50.3, 40.7, 40.3, 35.8, 34.4. MS (ESI) [M]$^+$ 521.8.

(2S,4S)-1-[(2-Chlorophenyl)methyl]-N-[2-(4-acetamidophenyl)ethyl]-4-{[(4-methoxyphenyl)methyl]amino}pyrrolidine-2-carboxamide (30) was prepared according to the general procedure A as colorless liquid (50%). $^1$H NMR (300 MHz, CDCl$_3$) δ 8.44 (br. s., 1H), 7.67 (t, J=5.75 Hz, 1H), 7.37 (dd, J=1.60, 7.44 Hz, 1H), 7.23-7.31 (m, 6H), 7.11-7.21 (m, 2H), 7.03 (d, J=8.29 Hz, 2H), 6.86 (d, J=8.67 Hz, 2H), 3.84 (s, 2H), 3.76 (s, 3H), 3.62-3.74 (m, 2H), 3.39-3.48 (m, 2H), 3.34 (td, J=6.31, 12.62 Hz, 1H), 3.11-3.23 (m, 2H), 2.66-2.75 (m, 2H), 2.54 (dd, J=5.56, 11.02 Hz, 1H), 2.28-2.41 (m, 1H), 2.07 (s, 3H), 1.76 (d, J=14.32 Hz, 1H). $^{13}$C NMR (75 MHz, CDCl$_3$) δ 173.1, 168.9, 160.1, 136.1, 134.5, 134.5, 133.5, 130.9, 130.5, 129.2, 129.0, 128.5, 126.8, 120.6, 114.3, 65.6, 55.0, 54.8, 54.4, 53.5, 48.7, 39.8, 34.4, 33.7, 23.9. MS (ESI) [M]$^+$ 535.6.

(2S,4S)-1-[(2-Chlorophenyl)methyl]-4-{[(4-methoxyphenyl)methyl]amino}-N-{2-[4-(methylcarbamoyl)phenyl]ethyl}pyrrolidine-2-carboxamide (31) was prepared according to the general procedure A as colorless oil (28%). $^1$H NMR (300 MHz, CDCl$_3$) δ 7.75 (t, J=5.84 Hz, 1H), 7.53 (d, J=8.10 Hz, 2H), 7.37 (dd, J=2.17, 6.88 Hz, 1H), 7.22 (d, J=8.67 Hz, 2H), 7.09-7.18 (m, 4H), 6.82 (d, J=8.48 Hz, 3H), 3.86 (d, J=2.45 Hz, 2H), 3.71-3.77 (m, 3H), 3.57-3.68 (m, 2H), 3.33-3.54 (m, 3H), 3.12-3.23 (m, 2H), 3.06 (q, J=7.41 Hz, 1H), 2.89 (d, J=4.71 Hz, 3H), 2.74-2.83 (m, 2H), 2.38-2.55 (m, 2H), 1.94 (dd, J=3.58, 14.13 Hz, 1H), 1.34-1.45 (m, 5H). $^{13}$C NMR (75 MHz, CDCl$_3$) δ 173.0, 168.3, 160.4, 142.5, 134.7, 133.6, 132.7, 131.3, 130.5, 129.5, 128.8, 128.7, 127.1, 114.5, 66.5, 55.2, 54.9, 54.7, 53.7, 48.9, 42.0, 39.8, 35.0, 33.8, 26.7, 11.8. MS (ESI) [M]$^+$ 535.5.

(2S,4S)—N-[2-(4-tert-Butylphenyl)ethyl]-1-[(2-chlorophenyl)methyl]-4-{[(4-methoxyphenyl)methyl]amino}pyrrolidine-2-carboxamide (32) was prepared according to the general procedure A as colorless oil (36%). $^1$H NMR (300 MHz, CDCl$_3$) δ 7.51 (br. s., 1H), 7.31-7.36 (m, 1H), 7.14-7.25 (m, 8H), 7.05 (d, J=8.29 Hz, 2H), 6.83 (d, J=8.67 Hz, 2H), 3.75-3.83 (m, 5H), 3.57-3.67 (m, 3H), 3.40-3.50 (m, 1H), 3.30-3.39 (m, 1H), 3.20-3.26 (m, 2H), 2.92 (d, J=10.17 Hz, 1H), 2.67 (q, J=7.03 Hz, 2H), 2.41-2.56 (m, 2H), 1.80-1.89 (m, 1H), 1.26 (s, 9H). $^{13}$C NMR (75 MHz, CDCl$_3$) δ 174.1, 158.7, 149.2, 135.8, 135.8, 134.1, 132.1, 130.9, 129.6, 129.3, 128.7, 128.3, 126.9, 125.4, 113.8, 67.2, 59.6, 57.2, 56.1, 55.2, 51.2, 39.9, 37.3, 35.1, 34.3, 31.3. MS (ESI) [M]$^+$ 534.3.

(2S,4S)-1-[(2-Chlorophenyl)methyl]-N-[2-(4-methoxyphenyl)ethyl]-4-{[(4-nitrophenyl)methyl]amino}pyrrolidine-2-carboxamide (33) was prepared according to the general procedure A as yellow oil (22%). $^1$H NMR (300 MHz, CDCl$_3$) δ 8.06 (d, J=8.67 Hz, 2H), 7.45-7.51 (m, 1H), 7.31-7.36 (m, 1H), 7.27 (s, 1H), 7.13-7.26 (m, 6H), 6.82-6.89 (m, 2H), 3.79 (s, 3H), 3.62-3.74 (m, 4H), 3.34-3.53 (m, 3H), 3.11-3.22 (m, 2H), 2.83 (dt, J=2.92, 6.92 Hz, 2H), 2.22-2.33 (m, 1H), 2.08 (t, J=7.54 Hz, 2H), 1.46-1.72 (m, 2H). $^{13}$C NMR (75 MHz, CDCl$_3$) δ 174.1, 158.9, 146.7, 146.7, 135.5, 134.1, 130.9, 129.7, 129.5, 129.2, 129.0, 128.8, 127.0, 123.7, 113.9, 66.6, 60.1, 58.1, 55.9, 55.3, 52.0, 39.2, 37.8, 35.6. MS (ESI) [M]$^+$ 523.7.

(2S,4S)-1-[(2-Chlorophenyl)methyl]-N-[2-(3,4-difluorophenyl)ethyl]-4-{[(4-methoxyphenyl)methyl]amino}pyrrolidine-2-carboxamide (34) was prepared according to the general procedure A as white solid (62%). $^1$H NMR (300 MHz, CDCl$_3$) δ 7.55 (t, J=6.03 Hz, 1H), 7.29 (d, J=2.26 Hz, 1H), 7.11-7.25 (m, 5H), 6.88-6.96 (m, 2H), 6.75-6.86 (m, 3H), 3.72-3.79 (m, 4H), 3.54-3.71 (m, 3H), 3.30-3.47 (m, 3H), 3.19 (dd, J=6.69, 9.14 Hz, 1H), 3.07 (d, J=10.93 Hz, 1H), 2.67 (q, J=6.91 Hz, 2H), 2.43-2.56 (m, 2H), 1.94 (dd, J=3.11, 6.50 Hz, 1H). $^{13}$C NMR (75 MHz, CDCl$_3$) δ 173.2, 159.7, 135.8, 135.0, 133.7, 130.5, 130.2, 129.6, 128.7, 126.9, 124.5, 124.5, 124.4, 124.4, 117.5, 117.2, 117.1, 116.9, 114.2, 67.2, 57.6, 56.0, 55.3, 55.2, 49.8, 39.6, 38.6, 35.1, 34.5. MS (ESI) [M]+ 514.5.

(2S,4S)-1-[(2-Chlorophenyl)methyl]-N-[2-(4-fluorophenyl)ethyl]-4-{[(4-methoxyphenyl)methyl]amino}pyrrolidine-2-carboxamide (35) was prepared according to the general procedure A as colorless oil (74%). $^1$H NMR (300 MHz, CDCl$_3$) δ 7.38 (t, J=5.84 Hz, 1H), 7.16-7.26 (m, 4H), 7.01-7.12 (m, 4H), 6.77-6.86 (m, 4H), 3.73-3.87 (m, 2H), 3.70 (s, 3H), 3.60-3.67 (m, 1H), 3.47-3.58 (m, 3H), 3.24-3.37 (m, 1H), 3.10-3.21 (m, 2H), 2.63-2.81 (m, 2H), 2.44-2.56 (m, 2H), 1.93-2.04 (m, 1H). $^{13}$C NMR (75 MHz, CDCl$_3$) δ 172.3, 160.5, 134.4, 134.3, 134.3, 133.5, 131.4, 130.0, 129.9, 129.5, 128.6, 126.9, 121.8, 115.3, 115.0, 114.5, 67.1, 55.8, 55.2, 54.9, 54.6, 48.7, 40.1, 34.4, 33.4. MS (ESI) [M]+ 496.7.

(2S,4S)-1-[(2-Chlorophenyl)methyl]-4-{[(4-methoxyphenyl)methyl]amino}-N-{2-[4-(trifluoromethyl)phenyl]ethyl}pyrrolidine-2-carboxamide (36) was prepared according to the general procedure A as yellow oil (69%). $^1$H NMR (300 MHz, CDCl$_3$) δ 7.54 (t, J=5.84 Hz, 1H), 7.43 (d, J=8.10 Hz, 2H), 7.32 (dd, J=1.88, 7.35 Hz, 1H), 7.14-7.24 (m, 7H), 6.81-6.86 (m, 2H), 3.73-3.80 (m, 4H), 3.57-3.70 (m, 3H), 3.38-3.48 (m, 2H), 3.29-3.36 (m, 1H), 3.23 (dd, J=5.84, 9.80 Hz, 1H), 3.00 (s, 1H), 2.71-2.81 (m, 2H), 2.42-2.58 (m, 2H), 1.80-1.90 (m, 1H). $^{13}$C NMR (75 MHz, CDCl$_3$) δ 174.0, 159.0, 143.0, 135.5, 134.0, 130.6, 129.6, 129.0, 128.8, 126.9, 125.4, 125.3, 114.0, 67.1, 59.0, 57.0, 56.0, 55.2, 50.9, 39.5, 36.7, 35.4. MS (ESI) [M]+ 546.7.

(2S,4S)-1-[(2-Chlorophenyl)methyl]-4-{[(4-methoxyphenyl)methyl]amino}-N-[2-(pyridin-4-yl)ethyl]pyrrolidine-2-carboxamide (37) was prepared according to the general procedure A as white solid (73%). $^1$H NMR (300 MHz, CDCl$_3$) δ 8.34 (d, J=5.84 Hz, 2H), 7.65 (t, J=5.93 Hz, 1H), 7.24-7.33 (m, 3H), 7.20 (d, J=8.67 Hz, 2H), 7.10-7.15 (m, 2H), 7.05 (d, J=6.03 Hz, 2H), 6.82 (d, J=8.67 Hz, 2H), 3.75-3.86 (m, 2H), 3.67 (br. s., 5H), 3.50 (quin, J=6.83 Hz, 2H), 3.35-3.44 (m, 1H), 3.10-3.20 (m, 2H), 2.76 (dt, J=2.83, 7.06 Hz, 2H), 2.44-2.57 (m, 2H), 1.93 (ddd, J=2.73, 7.16, 14.22 Hz, 1H). $^{13}$C NMR (75 MHz, CDCl$_3$) δ 172.7, 160.3, 149.4, 148.3, 134.5, 133.6, 131.2, 130.2, 129.6, 128.7, 126.9, 124.2, 114.5, 67.1, 56.2, 55.2, 54.8, 49.1, 38.9, 34.6, 34.0. MS (ESI) [M]+ 479.3.

(2S,4S)—N-[2-(4-Acetylphenyl)ethyl]-1-[(2-chlorophenyl)methyl]-4-{[(4-methoxyphenyl)methyl]amino}pyrrolidine-2-carboxamide (38) was prepared according to the general procedure A as colorless liquid (35%). $^1$H NMR (300 MHz, CDCl$_3$) δ 7.65-7.72 (m, 2H), 7.35-7.42 (m, 1H), 7.18-7.24 (m, 3H), 7.05-7.16 (m, 4H), 6.83 (d, J=8.67 Hz, 2H), 3.78-3.89 (m, 2H), 3.66-3.74 (m, 4H), 3.48-3.61 (m, 3H), 3.37 (d, J=5.65 Hz, 1H), 3.18 (d, J=8.10 Hz, 2H), 2.74-2.87 (m, 2H), 2.43-2.60 (m, 2H), 2.18 (d, J=5.84 Hz, 3H), 1.93-2.06 (m, 1H). $^{13}$C NMR (75 MHz, CDCl$_3$) δ 172.4, 160.5, 157.6, 140.4, 136.6, 134.4, 133.7, 131.5, 130.5, 129.5, 128.7, 128.6, 127.0, 126.7, 121.7, 114.6, 66.9, 55.5, 55.2, 54.7, 54.2, 48.6, 40.0, 35.1, 33.4, 14.8. MS (ESI) [M]+ 519.5.

(2S,4S)-1-[(2-Chlorophenyl)methyl]-N-[2-(4-methanesulfonylphenyl)ethyl]-4-{[(4-methoxyphenyl)methyl]amino}pyrrolidine-2-carboxamide (39) was prepared according to the general procedure A as colorless oil (55%). $^1$H NMR (300 MHz, CDCl$_3$) δ 7.75 (d, J=8.29 Hz, 2H), 7.64 (t, J=5.93 Hz, 1H), 7.25-7.35 (m, 5H), 7.16-7.22 (m, 4H), 6.81-6.86 (m, 2H), 3.76 (s, 3H), 3.59-3.74 (m, 4H), 3.42 (q, J=6.97 Hz, 2H), 3.32-3.37 (m, 1H), 3.23 (dd, J=5.84, 9.61 Hz, 1H), 3.01 (d, J=1.70 Hz, 1H), 2.98 (s, 3H), 2.79 (qd, J=6.99, 14.46 Hz, 2H), 2.55 (dd, J=5.65, 10.55 Hz, 1H), 2.41-2.50 (m, 1H), 1.81-1.91 (m, 1H). $^{13}$C NMR (75 MHz, CDCl$_3$) δ 174.0, 159.2, 145.6, 138.7, 135.4, 133.9, 130.7, 129.9, 129.7, 129.6, 128.9, 127.5, 127.0, 114.1, 67.0, 58.6, 56.7, 55.9, 55.3, 50.7, 44.5, 39.5, 36.3, 35.5. MS (ESI) [M]+ 557.1.

(2S,4S)-1-[(2-Chlorophenyl)methyl]-N,N-diethyl-4-{[(4-methoxyphenyl)methyl]amino}pyrrolidine-2-carboxamide (40) was prepared according to the general procedure A as yellow oil (54%). $^1$H NMR (300 MHz, CDCl$_3$) δ 7.37-7.44 (m, 3H), 7.31-7.35 (m, 1H), 7.18-7.23 (m, 2H), 6.87-6.93 (m, 2H), 4.09 (d, J=2.07 Hz, 2H), 3.91-4.00 (m, 3H), 3.82-3.86 (m, 1H), 3.81 (s, 3H), 3.39-3.51 (m, 2H), 3.18-3.29 (m, 1H), 2.88-3.08 (m, 3H), 2.36-2.48 (m, 1H), 2.14 (d, J=14.69 Hz, 1H), 1.04 (t, J=7.25 Hz, 3H), 0.97 (t, J=7.16 Hz, 3H). $^{13}$C NMR (75 MHz, CDCl$_3$) δ 174.0, 160.3, 135.1, 133.6, 131.3, 130.7, 129.5, 128.8, 127.1, 123.1, 114.6, 59.0, 56.7, 56.4, 55.3, 54.3, 48.5, 42.4, 41.6, 33.7, 15.0, 12.8. MS (ESI) [M]+ 430.4.

(2S,4S)-1-[(2-Chlorophenyl)methyl]-4-{[(4-methoxyphenyl)methyl]amino}-N,N-dipropylpyrrolidine-2-carboxamide (41) was prepared according to the general procedure A as colorless oil (63%). $^1$H NMR (300 MHz, CDCl$_3$) δ 7.55 (dd, J=1.70, 7.54 Hz, 1H), 7.13-7.34 (m, 6H), 6.85 (d, J=8.48 Hz, 2H), 3.73-3.92 (m, 7H), 3.70 (dd, J=4.52, 8.85 Hz, 1H), 3.44 (d, J=5.84 Hz, 1H), 2.99-3.35 (m, 6H), 2.81 (dd, J=6.03, 9.61 Hz, 1H), 2.40 (td, J=8.34, 13.28 Hz, 1H), 1.80-1.89 (m, 1H), 1.43-1.57 (m, 4H), 0.86 (dt, J=4.52, 7.44 Hz, 6H). $^{13}$C NMR (75 MHz, CDCl$_3$) δ 173.4, 158.9, 136.4, 133.6, 130.8, 129.7, 129.2, 128.1, 126.8, 113.9, 60.9, 58.3, 56.3, 55.3, 53.9, 50.7, 49.4, 48.3, 36.3, 22.8, 20.9, 11.4, 11.2. MS (ESI) [M]+ 458.2.

(3S,5S)-1-[(2-Chlorophenyl)methyl]-N-[(4-methoxyphenyl)methyl]-5-(4-phenylpiperazine-1-carbonyl)pyrrolidin-3-amine (42) was prepared according to the general procedure A as colorless oil (23%). $^1$H NMR (300 MHz, CDCl$_3$) δ 7.45 (dd, J=1.79, 7.44 Hz, 1H), 7.27-7.39 (m, 5H), 7.14-7.25 (m, 2H), 6.84-6.95 (m, 5H), 3.90-3.99 (m, 4H), 3.85 (dd, J=3.49, 9.14 Hz, 1H), 3.80 (s, 3H), 3.77 (s, 1H), 3.54-3.71 (m, 3H), 3.46 (br. s., 1H), 3.35 (d, J=10.55 Hz, 1H), 2.88-3.10 (m, 5H), 2.37-2.49 (m, 1H), 2.06 (d, J=14.13 Hz, 1H). $^{13}$C NMR (75 MHz, CDCl$_3$) δ 172.6, 159.7, 150.7, 135.4, 133.7, 130.9, 130.6, 129.6, 129.3, 128.8, 127.0, 120.7, 116.6, 114.3, 57.5, 56.4, 55.3, 54.6, 49.7, 49.6, 49.3, 45.6, 42.2, 34.7. MS (ESI) [M]+ 519.8.

(2S,4S)-1-[(2-Chlorophenyl)methyl]-N-ethyl-4-{[(4-(methylthio)phenyl)methyl]amino}pyrrolidine-2-carboxamide (43) was prepared according to the general procedure A as colorless oil (52%). $^1$H NMR (300 MHz, CDCl$_3$) δ 7.45 (br. s., 1H), 7.37 (dd, J=3.67, 5.56 Hz, 1H), 7.29-7.33 (m, 1H), 7.23 (dd, J=3.58, 5.84 Hz, 2H), 7.16-7.21 (m, 4H), 3.83-3.90 (m, 1H), 3.63-3.73 (m, 3H), 3.29 (d, J=5.84 Hz, 1H), 3.24 (dd, J=5.46, 9.98 Hz, 1H), 3.10-3.19 (m, 2H), 2.98 (d, J=9.98 Hz, 1H), 2.61 (dd, J=5.56, 10.08 Hz, 1H), 2.49-2.54 (m, 1H), 2.46 (s, 3H), 1.91 (dd, J=2.73, 8.76 Hz, 3H), 1.02 (t, J=7.35 Hz, 3H). $^{13}$C NMR (75 MHz, CDCl$_3$) δ 173.5, 136.6, 136.3, 135.3, 133.8, 130.7, 129.3, 128.5, 128.3, 126.5, 126.5, 66.6, 59.2, 57.1, 55.8, 50.8, 36.7, 33.2, 15.6, 14.1. MS (ESI) [M]+ 418.3.

(2S,4S)-1-[(2-Chlorophenyl)methyl]-4-{[(4-(methylthio)phenyl)methyl]amino}-N-pentylpyrrolidine-2-carboxamide (44) was prepared according to the general procedure A as colorless oil (62%). $^1$H NMR (300 MHz, CDCl$_3$) δ 7.47 (br. s., 1H), 7.31-7.39 (m, 2H), 7.21-7.26 (m, 2H), 7.17-7.20 (m, 4H), 3.84-3.91 (m, 1H), 3.59-3.75 (m, 3H), 3.30 (br. s., 1H), 3.25 (dd, J=5.46, 9.80 Hz, 1H), 3.10 (dt, J=6.97, 12.72 Hz, 2H), 2.99 (d, J=10.17 Hz, 1H), 2.60 (dd, J=5.46, 9.98 Hz, 1H), 2.48-2.54 (m, 1H), 2.46 (s, 3H), 1.91 (d, J=10.36 Hz, 2H), 1.32-1.43 (m, 2H), 1.17-1.29 (m, 4H), 0.84 (t, J=6.78

Hz, 3H). $^{13}$C NMR (75 MHz, CDCl$_3$) δ 174.0, 137.1, 136.7, 135.8, 134.2, 131.0, 129.7, 128.9, 128.7, 126.9, 67.1, 59.6, 57.5, 56.3, 51.3, 38.9, 37.1, 29.2, 29.1, 22.3, 16.1, 13.9. MS (ESI) [M]$^+$ 460.3.

(2S,4S)-1-[(2-Chlorophenyl)methyl]-4-{[(4-(methylthio)phenyl)methyl]amino}-N-(2-phenylethyl)pyrrolidine-2-carboxamide (45) was prepared according to the general procedure A as colorless oil (46%). $^1$H NMR (300 MHz, CDCl$_3$) δ 7.40 (br. s., 1H), 7.33 (dd, J=2.92, 4.43 Hz, 1H), 7.09-7.24 (m, 12H), 3.60-3.79 (m, 4H), 3.37-3.50 (m, 2H), 3.34 (d, J=6.03 Hz, 1H), 3.21 (dd, J=5.75, 9.51 Hz, 1H), 2.98 (d, J=10.36 Hz, 1H), 2.67-2.76 (m, 2H), 2.47-2.58 (m, 2H), 2.45 (s, 3H), 1.86 (d, J=12.62 Hz, 1H). $^{13}$C NMR (75 MHz, CDCl$_3$) δ 173.8, 138.8, 137.8, 135.5, 134.7, 134.0, 130.7, 129.6, 129.1, 128.7, 128.6, 128.5, 126.9, 126.8, 126.4, 67.0, 58.6, 56.6, 55.9, 50.7, 39.9, 36.4, 35.4, 15.9. MS (ESI) [M]$^+$ 494.7.

(2S,4S)-1-[(2-Chlorophenyl)methyl]-N-[2-(4-(methylthio)phenyl)ethyl]-4-{[(4-methoxyphenyl)methyl]amino}pyrrolidine-2-carboxamide (46) was prepared according to the general procedure A as colorless oil (50%). $^1$H NMR (300 MHz, CDCl$_3$) δ 7.47 (br. s., 1H), 7.32-7.38 (m, 1H), 7.15-7.24 (m, 7H), 7.02 (d, J=8.48 Hz, 2H), 6.73 (d, J=8.67 Hz, 2H), 3.71-3.80 (m, 4H), 3.59-3.69 (m, 3H), 3.42 (dd, J=6.69, 13.28 Hz, 1H), 3.32-3.38 (m, 1H), 3.26 (d, J=4.14 Hz, 1H), 3.19-3.24 (m, 1H), 2.93 (d, J=9.98 Hz, 1H), 2.61-2.71 (m, 2H), 2.51 (dd, J=5.37, 10.08 Hz, 2H), 2.45 (s, 3H), 2.04 (br. s., 2H), 1.78-1.88 (m, 1H). $^{13}$C NMR (75 MHz, CDCl$_3$) δ 174.0, 158.2, 137.2, 136.5, 135.7, 134.0, 130.8, 130.7, 129.6, 129.5, 128.8, 128.7, 126.9, 113.9, 67.2, 59.3, 57.1, 56.1, 55.2, 51.2, 40.0, 37.1, 34.6, 16.0. MS (ESI) [M]$^+$ 524.5.

(2S,4S)-1-[(2-Chlorophenyl)methyl]-N-[2-(4-(methylthio)phenyl)ethyl]-4-{[(4-nitrophenyl)methyl]amino}pyrrolidine-2-carboxamide (47) was prepared according to the general procedure A as colorless oil (44%). $^1$H NMR (300 MHz, CDCl$_3$) δ 7.93 (d, J=8.67 Hz, 2H), 7.53 (t, J=6.03 Hz, 1H), 7.23-7.28 (m, 1H), 7.06-7.18 (m, 8H), 3.51-3.70 (m, 4H), 3.37 (q, J=6.78 Hz, 2H), 3.22 (d, J=3.20 Hz, 1H), 3.17 (dd, J=5.65, 9.80 Hz, 1H), 2.88 (d, J=10.17 Hz, 1H), 2.72 (qd, J=7.10, 14.13 Hz, 2H), 2.40-2.49 (m, 2H), 2.39 (s, 3H), 1.85 (br. s., 1H), 1.70-1.79 (m, 1H). $^{13}$C NMR (75 MHz, CDCl$_3$) δ 173.3, 145.7, 145.6, 136.4, 135.4, 134.6, 132.9, 129.4, 128.7, 128.4, 127.8, 127.7, 125.9, 125.8, 122.6, 66.1, 58.4, 56.3, 55.3, 50.3, 38.2, 36.1, 34.5, 14.9. MS (ESI) [M]$^+$ 539.2.

(2S,4S)-1-[(2-Chlorophenyl)methyl]-N-[2-(3,4-difluorophenyl)ethyl]-4-{[(4-(methylthio)phenyl)methyl]amino}pyrrolidine-2-carboxamide (48) was prepared according to the general procedure A as colorless liquid (56%). $^1$H NMR (300 MHz, CDCl$_3$) δ 7.58 (br. s., 1H), 7.34 (d, J=7.35 Hz, 1H), 7.15-7.25 (m, 7H), 6.88-7.00 (m, 2H), 6.75-6.83 (m, 1H), 3.70-3.80 (m, 1H), 3.59-3.69 (m, 3H), 3.35-3.45 (m, 1H), 3.33 (d, J=6.97 Hz, 2H), 3.24 (dd, J=5.65, 9.61 Hz, 1H), 2.96 (d, J=9.80 Hz, 1H), 2.60-2.70 (m, 2H), 2.54 (dd, J=5.56, 10.46 Hz, 2H), 2.41-2.49 (m, 4H), 1.85 (d, J=13.00 Hz, 1H). $^{13}$C NMR (75 MHz, CDCl$_3$) δ 174.1, 137.5, 135.9, 135.6, 134.0, 130.6, 129.7, 128.8, 128.8, 126.9, 126.9, 124.5, 124.5, 124.4, 124.4, 117.5, 117.3, 117.2, 117.0, 67.1, 59.2, 57.1, 56.1, 51.2, 39.6, 36.9, 34.7, 15.9. MS (ESI) [M]$^+$ 530.9.

(2S,4R)-1-[(2-Chlorophenyl)methyl]-4-hydroxypyrrolidine-2-carboxylic acid (49). To a solution of 3 (0.87 g, 3.22 mmol) in methanol (30 ml) was added lithium hydroxide (0.386 g, 16.12 mmol). After stirring at room temperature for 3 h, the reaction mixture was concentrated in vacuo. The residue was dissolved in water and the pH was adjusted to 5 with 3N HCl aqueous solution. The reaction mixture was extracted three times with ethyl acetate. The combined organic layers were dried over anhydrous magnesium sulfate and concentrated in vacuo to provide the product as white solid (0.63 g, 76%). $^1$H NMR (300 MHz, CDCl$_3$) δ 7.74-7.79 (m, 2H), 7.37-7.46 (m, 1H), 7.28-7.35 (m, 3H), 7.17-7.23 (m, 2H), 5.01 (d, J=5.46 Hz, 1H), 3.74-4.04 (m, 2H), 3.69 (s, 1H), 3.66 (s, 1H), 3.29 (dd, J=6.03, 11.11 Hz, 1H), 3.12-3.17 (m, 1H), 2.67-2.73 (m, 1H), 2.44 (s, 3H), 2.28 (dd, J=5.46, 7.54 Hz, 2H). MS (ESI) [M]+256.4, [M−H]$^-$ 254.3.

(2S,4R)-1-[(2-Chlorophenyl)methyl]-4-hydroxy-N-[2-(4-nitrophenyl)ethyl]pyrrolidine-2-carboxamide (50). To a solution of 49 (0.825 g, 3.2 mmol) in DMF (10 ml) was added 4-nitrophenethylamine (0.981 g, 4.8 mmol), HBTU (1.346 g, 3.5 mmol), and diisopropylethylamine (2.8 ml, 16.1 mmol). After stirring at room temperature for 24 h, the reaction mixture was diluted with ethyl acetate, washed water (100 ml each, three times) and brine (100 ml). The organic layer was dried over anhydrous magnesium sulfate, and concentrated in vacuo. The residue was purified by flash column chromatography (silica gel, methanol/dichloromethane) to provide the product as white solid (0.55 g, 42%). $^1$H NMR (300 MHz, CDCl$_3$) δ 8.02 (d, J=8.67 Hz, 2H), 7.53 (t, J=6.03 Hz, 1H), 7.16-7.35 (m, 6H), 4.28-4.37 (m, 1H), 3.72-3.87 (m, 2H), 3.56 (t, J=8.10 Hz, 1H), 3.44 (q, J=6.78 Hz, 2H), 3.23 (dd, J=4.90, 10.55 Hz, 1H), 2.77-2.89 (m, 2H), 2.53 (dd, J=4.14, 10.55 Hz, 1H), 2.28 (ddd, J=4.24, 8.62, 12.95 Hz, 1H), 1.86-1.98 (m, 1H). MS (ESI) [M]$^+$ 404.3.

(3R,5S)-1-[(2-Chlorophenyl)methyl]-5-{[2-(4-nitrophenyl)ethyl]carbamoyl}pyrrolidin-3-yl 4-methylbenzene-1-sulfonate (51). To a solution of 50 (0.550 g, 1.36 mmol) in dichloromethane (5 ml) was added toluenesulfonyl chloride (0.519 g, 2.72 mmol) and pyridine (5 ml). After stirring at room temperature for 24 h, the reaction mixture was concentrated in vacuo. The residue was dissolved in dichloromethane, washed with aqueous saturated copper sulfate solution twice. The combined organic fractions were pooled, washed with brine, dried over anhydrous magnesium sulfate, and concentrated in vacuo. The residue was purified by flash column chromatography (silica gel, ethyl acetate/hexanes) to afford the product as white solid (0.44 g, 58%). $^1$H NMR (300 MHz, CDCl$_3$) δ 7.76 (d, J=8.29 Hz, 2H), 7.30-7.37 (m, 4H), 7.15-7.25 (m, 4H), 4.86-4.94 (m, J=5.65 Hz, 1H), 3.75 (d, J=2.64 Hz, 2H), 3.39-3.52 (m, 3H), 3.17 (dd, J=4.90, 11.87 Hz, 1H), 2.73-2.88 (m, 3H), 2.45 (s, 3H), 2.32-2.42 (m, 1H), 1.90-2.01 (m, 1H).

General procedure B: To a solution of 45 (0.12 mmol, 0.068 g) in THF (2 ml) was added corresponding amine (1.2 mmol) and triethylamine (0.36 mmol, 0.05 ml). The reaction was refluxed for 72 h. After cooling to room temperature, the solvent was evaporated in vacuo. The residue was purified by column chromatography (SiO$_2$, MeOH/DCM) to give the desired product.

(2S,4S)-1-[(2-Chlorophenyl)methyl]-N-[2-(4-nitrophenyl)ethyl]-4-propylamino)pyrrolidine-2-carboxamide (52) was prepared according to the general procedure B as yellow oil (11%). $^1$H NMR (300 MHz, CDCl$_3$) δ 8.02-8.08 (m, 2H), 7.61 (t, J=6.03 Hz, 1H), 7.32-7.36 (m, 1H), 7.29 (d, J=8.67 Hz, 2H), 7.16-7.25 (m, 3H), 3.60-3.77 (m, 2H), 3.47 (dq, J=3.77, 6.72 Hz, 2H), 3.21-3.29 (m, 2H), 2.80-2.95 (m, 3H), 2.38-2.59 (m, 4H), 1.67-1.78 (m, 1H), 1.40 (qd, J=7.29, 14.67 Hz, 3H), 0.87 (t, J=7.35 Hz, 3H). $^{13}$C NMR (75 MHz, CDCl$_3$) δ 174.4, 146.8, 146.7, 135.7, 133.9, 130.4, 129.7, 129.4, 128.8, 126.9, 123.7, 67.4, 59.8, 57.4, 56.9, 49.9, 39.3, 37.6, 35.6, 23.3, 11.7. MS (ESI) [M]$^+$ 445.6.

(2S,4S)-4-(Butylamino)-1-[(2-chlorophenyl)methyl]-N-[2-(4-nitrophenyl)ethyl]pyrrolidine-2-carboxamide (53) was prepared according to the general procedure B as yellow oil (39%). $^1$H NMR (300 MHz, CDCl$_3$) δ 7.88-7.99 (m, 2H), 7.79 (t, J=5.93 Hz, 1H), 7.69 (d, J=7.91 Hz, 1H), 7.29-7.36 (m, 2H), 7.10-7.25 (m, 5H), 3.61-3.66 (m, 2H), 3.56 (dd, J=6.69, 14.03 Hz, 1H), 3.44-3.51 (m, 1H), 3.34-3.43 (m, 1H), 3.26 (dd, J=6.78, 8.67 Hz, 1H), 3.09 (d, J=10.55 Hz, 1H), 2.82 (qd, J=7.08, 13.99 Hz, 2H), 2.61-2.70 (m, 2H), 2.48-2.58 (m, 2H), 2.39 (s, 1H), 1.86-1.98 (m, 1H), 1.52 (quin, J=7.49 Hz, 2H), 1.27 (qd, J=7.42, 15.05 Hz, 2H), 0.85 (t, J=7.44 Hz, 3H). $^{13}$C NMR (75 MHz, CDCl$_3$) δ 173.6, 146.8, 146.5, 142.0, 140.7, 135.1, 133.7, 130.3, 129.6, 129.4, 129.0, 128.7, 126.9, 125.7, 123.5, 66.9, 56.7, 55.8, 46.9, 39.3, 35.8, 35.2, 30.0, 21.3, 20.1, 13.6. MS (ESI) [M]$^+$ 459.3.

(2S,4S)-1-[(2-Chlorophenyl)methyl]-N-[2-(4-nitrophenyl)ethyl]-4-(pentylamino) pyrrolidine-2-carboxamide (54) was prepared according to the general procedure B as colorless oil (59%). $^1$H NMR (300 MHz, CDCl$_3$) δ 8.05 (d, J=8.67 Hz, 2H), 7.62 (t, J=5.93 Hz, 1H), 7.26-7.36 (m, 3H), 7.16-7.25 (m, 2H), 3.59-3.76 (m, 2H), 3.47 (td, J=6.57, 12.67 Hz, 2H), 3.21-3.29 (m, 2H), 2.81-2.96 (m, 3H), 2.42-2.58 (m, 3H), 1.72 (ddd, J=3.77, 5.75, 13.28 Hz, 1H), 1.19-1.44 (m, 6H), 0.87 (t, J=6.88 Hz, 3H). $^{13}$C NMR (75 MHz, CDCl$_3$) δ 174.4, 146.8, 146.7, 135.7, 133.9, 130.4, 129.7, 129.4, 128.8, 126.9, 123.7, 67.4, 59.7, 57.3, 56.9, 48.0, 39.3, 37.6, 35.6, 29.9, 29.5, 22.5, 14.0. MS (ESI) [M]$^+$ 473.8.

(2S,4S)-1-[(2-Chlorophenyl)methyl]-4-(hexylamino)-N-[2-(4-nitrophenyl)ethyl]pyrrolidine-2-carboxamide (55) was prepared according to the general procedure B as colorless oil (25%). $^1$H NMR (300 MHz, CDCl$_3$) δ 8.05 (d, J=8.67 Hz, 2H), 7.54 (t, J=5.93 Hz, 1H), 7.27-7.36 (m, 3H), 7.15-7.25 (m, 3H), 3.61-3.77 (m, 2H), 3.46 (td, J=6.73, 13.28 Hz, 2H), 3.22-3.33 (m, 2H), 2.75-2.99 (m, 3H), 2.43-2.60 (m, 3H), 1.64-1.80 (m, 4H), 1.36-1.45 (m, 2H), 1.21-1.32 (m, 6H), 0.84-0.91 (m, 3H). $^{13}$C NMR (75 MHz, CDCl$_3$) δ 174.4, 146.7, 135.6, 133.9, 130.4, 129.7, 129.4, 128.8, 126.9, 123.7, 67.2, 59.5, 57.2, 57.0, 48.0, 39.3, 37.4, 35.5, 31.6, 30.0, 27.0, 22.6, 14.0. MS (ESI) [M]$^+$ 487.4.

(2S,4S)-4-(Benzylamino)-1-[(2-chlorophenyl)methyl]-N-[2-(4-nitrophenyl)ethyl]pyrrolidine-2-carboxamide (56) was prepared according to the general procedure B as colorless oil (81%). $^1$H NMR (300 MHz, CDCl$_3$) δ 7.96-8.03 (m, 2H), 7.62 (t, J=5.75 Hz, 1H), 7.15-7.37 (m, 11H), 3.59-3.78 (m, 4H), 3.45 (q, J=6.97 Hz, 2H), 3.22-3.34 (m, 2H), 2.96 (d, J=10.17 Hz, 1H), 2.79 (qd, J=7.07, 14.20 Hz, 2H), 2.43-2.60 (m, 2H), 1.82 (td, J=3.72, 13.47 Hz, 1H), 1.53 (br. s., 2H). $^{13}$C NMR (75 MHz, CDCl$_3$) δ 174.4, 146.7, 146.6, 140.0, 135.7, 134.0, 130.5, 129.7, 129.4, 128.8, 128.5, 128.1, 127.2, 126.9, 123.6, 67.2, 59.6, 57.4, 56.4, 52.0, 39.2, 37.4, 35.5. MS (ESI) [M]$^+$ 493.8.

(2S,4S)-4-(Benzylamino)-1-[(2-chlorophenyl)methyl]-N-[2-(4-nitrophenyl)ethyl]pyrrolidine-2-carboxamide (57) was prepared according to the general procedure B as colorless oil (13%). $^1$H NMR (300 MHz, CDCl$_3$) δ 8.00 (d, J=8.85 Hz, 1H), 7.16-7.42 (m, 12H), 3.62-3.75 (m, 1H), 3.46-3.60 (m, 3H), 3.32 (t, J=8.10 Hz, 1H), 3.19-3.28 (m, 1H), 3.14 (dd, J=4.24, 10.64 Hz, 1H), 2.86 (dt, J=4.43, 6.83 Hz, 2H), 2.54-2.64 (m, 1H), 2.49 (dd, J=6.03, 13.37 Hz, 1H), 2.10-2.17 (m, 2H), 1.88-2.00 (m, 1H). $^{13}$C NMR (75 MHz, CDCl$_3$) δ 173.7, 146.7, 146.6, 135.5, 133.8, 130.2, 129.7, 129.4, 129.3, 128.8, 128.5, 127.7, 127.0, 125.5, 123.7, 67.8, 62.7, 59.5, 57.6, 56.9, 39.3, 38.6, 35.4, 34.5. MS (ESI) [M]$^+$ 507.2.

(2S,4S)-1-[(2-Chlorophenyl)methyl]-N-[2-(4-nitrophenyl)ethyl]-4-[(2-(phenylethyl)amino]pyrrolidine-2-carboxamide (58) was prepared according to the general procedure B as yellow oil (30%). $^1$H NMR (300 MHz, CDCl$_3$) δ 7.99-8.06 (m, 1H), 7.48 (t, J=5.93 Hz, 1H), 7.28-7.36 (m, 3H), 7.13-7.25 (m, 7H), 3.60-3.71 (m, 2H), 3.48 (td, J=6.90, 13.89 Hz, 1H), 3.28-3.35 (m, 1H), 3.18-3.25 (m, 1H), 2.88-3.02 (m, 2H), 2.70-2.83 (m, 6H), 2.44-2.56 (m, 2H), 1.85 (d, J=6.97 Hz, 1H), 1.63-1.73 (m, 1H). $^{13}$C NMR (75 MHz, CDCl$_3$) δ 174.2, 146.7, 139.7, 135.6, 133.9, 130.3, 129.7, 129.4, 128.8, 128.8, 128.6, 128.6, 128.5, 128.5, 126.9, 126.3, 123.6, 67.3, 59.2, 57.2, 56.7, 48.9, 39.2, 37.6, 36.2, 35.5. MS (ESI) [M]$^+$ 507.2.

(2S,4S)-1-[(2-Chlorophenyl)methyl]-4-{[(3-methoxyphenyl)methyl]amino}-N-[2-(4-nitrophenyl)ethyl]pyrrolidine-2-carboxamide (59) was prepared according to the general procedure B as yellow oil (20%). $^1$H NMR (300 MHz, CDCl$_3$) δ 8.01 (d, J=8.67 Hz, 2H), 7.60 (t, J=5.93 Hz, 1H), 7.31-7.35 (m, 1H), 7.18-7.25 (m, 6H), 6.74-6.88 (m, 4H), 3.79 (s, 3H), 3.69-3.72 (m, 1H), 3.62-3.69 (m, 3H), 3.45 (q, J=6.97 Hz, 2H), 3.32 (td, J=2.99, 5.51 Hz, 1H), 3.25 (dd, J=5.37, 9.89 Hz, 1H), 2.97 (d, J=9.98 Hz, 1H), 2.80 (q, J=7.35 Hz, 2H), 2.51-2.58 (m, 1H), 2.48 (td, J=3.58, 9.98 Hz, 1H), 1.77-1.81 (m, 1H). $^{13}$C NMR (75 MHz, CDCl3) δ 174.5, 159.8, 146.7, 146.7, 141.1, 135.6, 134.0, 130.5, 129.7, 129.5, 129.4, 128.8, 126.9, 123.6, 120.4, 114.1, 112.4, 67.1, 59.4, 57.2, 56.5, 55.2, 51.8, 39.3, 37.2, 35.5. MS (ESI) [M]$^+$ 523.5.

(2S,4S)-1-[(2-Chlorophenyl)methyl]-4-{[(3,4-dimethoxyphenyl)methyl]amino}-N-[2-(4-nitrophenyl)ethyl]pyrrolidine-2-carboxamide (60) was prepared according to the general procedure B as colorless oil (41%). $^1$H NMR (300 MHz, CDCl$_3$) δ 8.00 (d, J=8.67 Hz, 2H), 7.60 (t, J=6.03 Hz, 1H), 7.30-7.36 (m, 1H), 7.16-7.25 (m, 5H), 6.76-6.84 (m, 4H), 3.82-3.91 (m, 9H), 3.64-3.72 (m, 2H), 3.58-3.63 (m, 2H), 3.45 (q, J=6.78 Hz, 2H), 3.22-3.34 (m, 2H), 2.95 (d, J=10.36 Hz, 1H), 2.79 (q, J=7.10 Hz, 2H), 2.45-2.59 (m, 2H), 1.77-1.96 (m, 2H). $^{13}$C NMR (75 MHz, CDCl$_3$) δ 174.3, 149.1, 148.3, 146.7, 135.7, 134.0, 132.5, 130.5, 129.7, 129.4, 128.9, 126.9, 123.6, 120.2, 111.6, 111.3, 111.1, 67.2, 59.6, 57.5, 56.2, 55.9, 51.8, 39.2, 37.4, 35.5. MS (ESI) [M]$^+$ 553.7.

(2S,4S)-1-[(2-Chlorophenyl)methyl]-4-{[(4-hydroxyphenyl)methyl]amino}-N-[2-(4-nitrophenyl)ethyl]pyrrolidine-2-carboxamide (61) was prepared according to the general procedure B as colorless oil (27%). $^1$H NMR (300 MHz, CDCl$_3$) δ 7.94 (d, J=8.67 Hz, 2H), 7.69 (t, J=7.72 Hz, 1H), 7.28-7.35 (m, 1H), 7.14-7.25 (m, 4H), 7.05 (d, J=8.48 Hz, 2H), 6.61-6.74 (m, 2H), 3.58-3.70 (m, 3H), 3.46 (td, J=6.69, 13.37 Hz, 1H), 3.38 (d, J=6.78 Hz, 1H), 3.24 (dd, J=6.12, 9.32 Hz, 1H), 3.01 (d, J=10.36 Hz, 1H), 2.74-2.82 (m, 2H), 2.42-2.56 (m, 2H), 1.84 (m, 1H). $^{13}$C NMR (75 MHz, CDCl$_3$) δ 174.3, 155.7, 146.7, 135.4, 133.8, 130.4, 129.8, 129.6, 129.4, 129.0, 128.8, 126.9, 125.8, 123.6, 115.6, 67.2, 58.8, 56.9, 56.3, 51.3, 39.3, 36.8, 35.4. MS (ESI) [M]$^+$ 509.4.

(2S,4S)-1-[(2-Chlorophenyl)methyl]-N-[2-(4-nitrophenyl)ethyl]-4-({[4-(trifluoromethyl)phenyl]methyl}amino)pyrrolidine-2-carboxamide (62) was prepared according to the general procedure B as colorless oil (9%). $^1$H NMR (300 MHz, CDCl$_3$) δ 8.02 (d, J=8.67 Hz, 2H), 7.55 (d, J=8.10 Hz, 3H), 7.32-7.38 (m, 3H), 7.16-7.24 (m, 4H), 3.61-3.79 (m, 4H), 3.46 (dd, J=2.54, 6.50 Hz, 2H), 3.26 (dd, J=5.37, 9.89 Hz, 2H), 2.93 (d, J=10.17 Hz, 1H), 2.76-2.85 (m, 2H), 2.44-2.59 (m, 2H), 1.84 (dd, J=4.14, 13.38 Hz, 1H). $^{13}$C NMR (75 MHz, CDCl$_3$) δ 174.2, 146.6, 144.1, 135.5, 134.0, 130.5, 129.8, 129.4, 129.0, 128.2, 126.9, 125.3, 123.6, 67.1, 59.6, 57.6, 56.5, 51.4, 39.2, 37.3, 35.5. MS (ESI) [M]$^+$ 561.3.

(2S,4S)-1-[(2-Chlorophenyl)methyl]-4-{[(4-chlorophenyl)methyl]amino}-N-[2-(4-nitrophenyl)ethyl]pyrrolidine-2-carboxamide (63) was prepared according to the general procedure B as colorless oil (14%). $^1$H NMR (300 MHz, CDCl$_3$) δ 8.02 (d, J=8.67 Hz, 2H), 7.58 (t, J=6.03 Hz, 1H), 7.14-7.36 (m, 10H), 3.85 (s, 2H), 3.59-3.77 (m, 5H), 3.45 (q, J=6.84 Hz, 2H), 3.25 (dd, J=5.37, 9.89 Hz, 2H), 2.92 (d, J=10.17 Hz, 1H), 2.80 (qd, J=6.91, 13.56 Hz, 2H), 2.42-2.57 (m, 2H). $^{13}$C NMR (75 MHz, CDCl$_3$) δ 174.3, 146.6, 138.5, 135.6, 134.0, 132.9, 130.5, 129.7, 129.6, 129.4, 128.9, 128.6, 128.5, 126.9, 123.7, 67.1, 59.6, 57.5, 56.4, 51.3, 39.2, 37.3, 35.5. MS (ESI) [M]$^+$ 527.5.

(2S,4S)-1-[(2-Chlorophenyl)methyl]-4-{[(4-fluorophenyl)methyl]amino}-N-[2-(4-nitrophenyl)ethyl]pyrrolidine-2-carboxamide (64) was prepared according to the general procedure B as colorless oil (55%). $^1$H NMR (300 MHz, CDCl$_3$) δ 8.01 (d, J=8.67 Hz, 2H), 7.59 (t, J=6.12 Hz, 1H), 7.31-7.36 (m, 1H), 7.15-7.28 (m, 7H), 6.95-7.02 (m, 2H), 3.57-3.77 (m, 4H), 3.45 (q, J=6.91 Hz, 2H), 3.21-3.32 (m, 2H), 2.93 (d, J=9.98 Hz, 1H), 2.80 (qd, J=6.92, 13.54 Hz, 2H), 2.42-2.58 (m, 2H), 1.76-1.86 (m, 1H). $^{13}$C NMR (75 MHz, CDCl$_3$) δ 174.3, 146.7, 135.6, 134.0, 130.5, 129.7, 129.7, 129.6, 129.4, 128.9, 126.9, 123.6, 115.4, 115.1, 67.1, 59.6, 57.5, 56.4, 51.2, 39.2, 37.3, 35.5. MS (ESI) [M]$^+$ 511.3.

1-tert-Butyl 2-methyl (2S,4R)-4-hydroxypyrrolidine-1,2-dicarboxylate (65). To a solution of methyl trans-4-hydroxy-L-proline 5 (27.6 mmol, 5.0 g) in 1N NaOH solution (28.5 ml) and 1,4-dioxane (28.5 ml) was added dropwise Boc$_2$O (30.3 mmol, 6.6 g) at 0° C. After stirring at room temperature for 8 h, the solvent was removed under vacuum. The residue was dissolved in ethyl acetate, washed with water and brine. The organic layer was dried over anhydrous MgSO$_4$, and concentrated in vacuo to give the desired product as colorless liquid (6.1 g, 90%). $^1$H NMR (300 MHz, CDCl$_3$) δ 4.51 (m, 1H), 4.43 (m, 1H), 3.74 (s, 3H), 3.64 (m, 2H), 2.29 (d, J=7.54 Hz, 1H), 2.10 (dd, J=4.52, 8.48 Hz, 1H), 1.44 (m, 9H). MS (ESI) [M+H]$^+$ 246.3, [M+Na]+ 268.1.

1-tert-Butyl 2-methyl (2S,4R)-4-[(4-methylbenzenesulfonyl)oxy]pyrrolidine-1,2-dicarboxylate (66). To a solution of 5 (11 g, 45 mmol) in dichloromethane (35 ml) at 0° C. was added toluenesulfonyl chloride (10.27 g, 53.9 mmol) and pyridine (35 ml). After stirring under reflux for 24 h, the reaction mixture was concentrated in vacuo and redissolved in dichloromethane. It was then washed with a saturated aqueous solution of copper sulfate and brine. The organic fraction was dried over anhydrous magnesium sulfate, and concentrated in vacuo. The residue was purified by flash column chromatography (silica gel, ethyl acetate/hexanes) to provide the product as light yellow liquid (12.6 g, 70%). $^1$H NMR (300 MHz, CDCl$_3$) δ 7.79 (d, J=8.29 Hz, 2H), 7.36 (d, J=8.10 Hz, 2H), 4.99-5.09 (m, 1H), 4.32-4.43 (m, 1H), 3.72 (s, 3H), 3.57-3.65 (m, 2H), 2.46 (s, 4H), 2.09-2.22 (m, J=8.70 Hz, 1H), 1.36-1.44 (m, 9H). MS (ESI) [M+H]$^+$ 400.3, [M+Na]+422.3.

1-tert-Butyl 2-methyl (2S,4S)-4-azidopyrrolidine-1,2-dicarboxylate (67). To a solution of 66 (4.28 g, 10.7 mmol) in DMF (40 ml) was added sodium azide (1.393 g, 21.4 mmol). After heating at 70° C. for 16 h, the reaction mixture was diluted with ethyl acetate, washed with water twice and brine once. The organic fraction was dried over anhydrous magnesium sulfate and concentrated in vacuo to provide the desired product as yellow liquid (2.87 g, 99%). $^1$H NMR (300 MHz, CDCl$_3$) δ 4.30-4.47 (m, 1H), 4.10-4.20 (m, 1H), 3.66-3.80 (m, 4H), 3.43-3.54 (m, 1H), 2.47 (ddt, J=6.03, 8.38, 13.89 Hz, 1H), 2.13-2.22 (m, 1H), 1.40-1.51 (m, 9H). MS (ESI) [M+H]$^+$ 271.1, [M+Na]+293.1.

1-tert-Butyl 2-methyl (2S,4S)-4-aminopyrrolidine-1,2-dicarboxylate (68). To a solution of azide 67 (2.87 g, 10.6 mmol) in THF (46 ml) under nitrogen was added PPh$_3$ (5.57 g, 21.2 mmol) and water (0.5 ml). The reaction mixture was refluxed with stirring for 6 h. After the solvent was removed, the residue was dissolved in diethyl ether, treated with 0.1N HCl for 5 min, and then extracted twice with diethyl ether. The aqueous layer was then treated with 1N NaOH until pH 10, and then extracted with dichloromethane. The combined dichloromethane fractions were dried over anhydrous magnesium sulfate, concentrated in vacuo to afford the desired product as yellow liquid (2.08 g, 80%). $^1$H NMR (300 MHz, CDCl$_3$) δ 4.20-4.37 (m, 1H), 3.72-3.79 (m, 3H), 3.63-3.72 (m, 1H), 3.50-3.58 (m, 1H), 3.26 (dd, J=4.99, 10.64 Hz, 1H), 2.38-2.53 (m, 1H), 1.75-1.86 (m, 1H), 1.39-1.48 (m, 9H). MS (ESI) [M+H]$^+$ 245.3.

1-tert-Butyl 2-methyl (2S,4S)-4-{[(4-methoxyphenyl)methyl]amino}pyrrolidine-1,2-dicarboxylate (69). To a solution of 68 (2.08 g, 7.74 mmol) in 1,2-dichloroethane (26 ml) was added 4-methoxybenzaldehyde (0.94 ml, 7.74 mmol), sodium triacetoxy boron hydride (2.461 g, 11.6 mmol) and acetic acid (0.44 ml, 7.74 mmol). After stirring at room temperature for 24 h, the reaction mixture was quenched with saturated sodium bicarbonate solution and extracted three times with dichloromethane. The combined organic layers were dried over anhydrous magnesium sulfate, and concentrated in vacuo. The residue was purified by flash column chromatography (silica gel, ethyl acetate/hexanes) to provide the product as colorless liquid (2.193 g, 73%). $^1$H NMR (300 MHz, CDCl$_3$) δ 7.21 (d, J=8.48 Hz, 2H), 6.85 (d, J=8.67 Hz, 2H), 4.20-4.35 (m, 1H), 3.79 (s, 3H), 3.58-3.75 (m, 6H), 3.25-3.37 (m, 2H), 2.29-2.45 (m, 1H), 1.90-2.01 (m, 1H), 1.39-1.48 (m, 9H). MS (ESI) [M+H]$^+$ 365.9.

1-tert-Butyl 2-methyl (2S,4S)-4-{[(4-methoxyphenyl)methyl][(2,2,2-trichloroethoxy)carbonyl]amino}pyrrolidine-1,2-dicarboxylate (70). To a solution of 69 (0.2 g, 0.5 mmol) in dichloromethane (2.5 ml) at 0° C. was added TrocCl (0.11 ml, 0.77 mmol) and triethylamine (0.14 ml, 1.02 mmol). The reaction mixture was brought to room temperature and stirred for 16 h. The reaction mixture was then washed with saturated aqueous sodium bicarbonate solution. The organic fraction was dried over anhydrous magnesium sulfate and concentrated in vacuo to give the product as colorless liquid (0.23 g, quantitative yield). $^1$H NMR (300 MHz, CDCl$_3$) δ 7.14 (d, J=8.29 Hz, 2H), 6.85 (d, J=8.48 Hz, 2H), 4.73-4.89 (m, 2H), 4.40-4.60 (m, 3H), 4.15-4.26 (m, 1H), 3.79 (s, 3H), 3.67-3.75 (m, 4H), 3.37-3.51 (m, 1H), 2.34-2.46 (m, 1H), 2.06-2.23 (m, 1H), 1.35-1.47 (m, 9H). MS (ESI) [M+H]$^+$ 539.3, [M+Na]+563.3.

(2S,4S)-1-[(tert-Butoxy)carbonyl]-4-{[(4-methoxyphenyl)methyl][(2,2,2-trichloroethoxy)carbonyl]amino}pyrrolidine-2-carboxylic acid (71). To a solution of 70 (0.274 g, 0.5 mmol) in methanol (2 ml) was added lithium hydroxide (0.048 g, 2 mmol). After stirring at room temperature, methanol was removed under reduced pressure. The residue was suspended in water and pH was adjusted to 5 by 1N HCl aqueous solution. The aqueous layer was extracted three times with dichloromethane. The combined organic fractions were dried over anhydrous magnesium sulfate, and concentrated in vacuo to give the product as white solid (0.225 g, 84%). $^1$H NMR (300 MHz, CDCl$_3$) δ 9.02 (br. s., 1H), 7.14 (d, J=4.33 Hz, 2H), 6.86 (d, J=7.16 Hz, 2H), 4.72-4.91 (m, 2H), 4.35-4.63 (m, 3H), 4.16-4.33 (m, 1H), 3.80 (s, 3H), 3.70-3.76 (m, 1H), 3.23-3.54 (m, 1H), 2.20-2.52 (m, 2H), 1.41 (d, J=17.52 Hz, 9H). MS (ESI) [M–H]⁻ 523.1.

tert-Butyl-(2S,4S)-4-{[(4-methoxyphenyl)methyl][(2,2,2-trichloroethoxy)carbonyl]amino}-2-[(2-phenylethyl)carbamoyl]pyrrolidine-1-carboxylate (72). To a solution of 71 (2.629 g, 5 mmol) in anhydrous dichloromethane (17 ml) was added phenethylamine hydrochloride (0.7 ml, 5.5 mmol), HBTU (2.086 g, 5.5 mmol), and diisopropylethylamine (3.2 ml, 18 mmol). After stirring at room temperature for 16 h, the reaction mixture was washed with 1N HCl aqueous solution. The organic layer was dried over anhydrous magnesium sulfate, and concentrated in vacuo. The residue was purified by flash column chromatography (silica gel, ethyl acetate/hexanes) to provide the product as yellow solid (2 g, 64%). $^1$H NMR (300 MHz, CDCl$_3$) δ 7.27 (t, J=3.67 Hz, 2H), 7.12-7.21 (m, 5H), 6.85 (d, J=8.67 Hz, 2H), 4.78 (br. s., 2H), 4.33-4.64 (m, 3H), 3.74-3.83 (m, 4H), 3.50 (d, J=5.84 Hz, 2H), 2.81-2.88 (m, 2H), 2.17-2.55 (m, 2H), 1.33-1.46 (m, 11H).

2,2,2-Trichloroethyl-N-[(4-methoxyphenyl)methyl]-N-[(3S,5S)-5-[(2-phenylethyl) carbamoyl]pyrrolidin-3-yl]carbamate (73). To a 20% v/v solution of trifluoroacetic acid in dichloromethane (4.4 ml) was added 72 (2 g, 3.2 mmol). The reaction mixture was stirred at room temperature overnight. The reaction mixture was then concentrated in vacuo to provide the product as yellow liquid (1.60 g, quantitative yield). MS (ESI) [M]⁺ 528.7.

General procedure C. To a solution of 73 (0.1 g, 0.19 mmol) in 1,2-dichloroethane (4 ml) was added a corresponding aldehyde (0.042 g, 0.28 mmol), sodium triacetoxy boron hydride (0.12 g, 0.57 mmol) and acetic acid (1 drop). After stirring at room temperature for 48 h, the reaction mixture was quenched with saturated aqueous sodium bicarbonate solution, and extracted with three times with dichloromethane. The organic extracts were dried over anhydrous magnesium sulfate, and concentrated in vacuo. The residue was dissolved in methanol (8 ml). Zinc (0.1 g, 1.5 mmol) and acetic acid (2 drops) was added to the reaction mixture. After stirring under reflux for 1 h, the reaction mixture was cooled to room temperature and concentrated in vacuo. The residue was purified by flash column chromatography (SiO$_2$, MeOH/DCM) to afford the desired products.

(2S,4S)-1-Hexyl-4-{[(4-methoxyphenyl)methyl]amino}-N-(2-phenylethyl)pyrrolidine-2-carboxamide (74) was prepared according to the general procedure C as colorless oil (27%). $^1$H NMR (300 MHz, CDCl$_3$) δ 7.50 (t, J=6.03 Hz, 2H), 7.27-7.30 (m, 1H), 7.24 (s, 1H), 7.14-7.22 (m, 6H), 6.83-6.87 (m, 2H), 3.79 (s, 3H), 3.61 (d, J=3.77 Hz, 2H), 3.41-3.59 (m, 2H), 3.23 (dt, J=3.01, 5.84 Hz, 1H), 2.97-3.04 (m, 2H), 2.75-2.82 (m, 2H), 2.33-2.52 (m, 3H), 2.21-2.31 (m, 1H), 1.69-1.78 (m, 1H), 1.07-1.38 (m, 9H), 0.89 (t, J=6.78 Hz, 3H). $^{13}$C NMR (75 MHz, CDCl$_3$) δ 174.8, 158.7, 139.0, 132.3, 129.3, 128.7, 128.5, 126.4, 113.8, 67.6, 59.3, 56.2, 56.0, 55.3, 51.3, 39.8, 37.1, 35.6, 31.7, 28.8, 27.0, 22.6, 14.0. MS (ESI) [M]⁺ 438.5.

(2S,4S)-1-(Cyclohexylmethyl)-4-{[(4-methoxyphenyl)methyl]amino}-N-(2-phenylethyl) pyrrolidine-2-carboxamide (75) was prepared according to the general procedure C as colorless oil (24%). $^1$H NMR (300 MHz, CDCl$_3$) δ 7.41 (t, J=5.84 Hz, 1H), 7.14-7.25 (m, 6H), 6.83-6.89 (m, 2H), 3.76-3.82 (m, 3H), 3.61-3.70 (m, 2H), 3.50-3.59 (m, 2H), 3.24 (td, J=2.76, 5.98 Hz, 1H), 2.94-3.01 (m, 2H), 2.80 (qd, J=6.98, 19.00 Hz, 1H), 2.31-2.45 (m, 2H), 2.08-2.25 (m, 2H), 1.48-1.81 (m, 8H), 1.23-1.37 (m, 1H), 1.04-1.21 (m, 3H), 0.67-0.82 (m, 1H), 0.44 (dd, J=3.20, 11.68 Hz, 1H). $^{13}$C NMR (75 MHz, CDCl$_3$) δ 173.6, 157.6, 137.7, 131.1, 128.2, 127.6, 127.5, 127.4, 125.3, 112.7, 66.9, 61.9, 58.1, 55.2, 54.1, 50.2, 38.5, 35.8, 35.6, 34.4, 30.6, 29.6, 25.5, 24.9, 24.8. MS (ESI) [M]⁺ 450.6.

(2S,4S)-1-Benzyl-4-{[(4-methoxyphenyl)methyl]amino}-N-(2-phenylethyl)pyrrolidine-2-carboxamide (76) was prepared according to the general procedure C as colorless oil (29%). $^1$H NMR (300 MHz, CDCl$_3$) δ 7.44-7.53 (m, 1H), 7.30 (m, 1H), 7.12-7.26 (m, 9H), 7.03-7.09 (m, 2H), 6.83 (d, J=8.48 Hz, 2H), 3.73-3.81 (m, 4H), 3.46-3.60 (m, 4H), 3.36 (d, J=13.00 Hz, 1H), 3.15-3.26 (m, 2H), 2.87 (d, J=10.36 Hz, 1H), 2.72-2.81 (m, 2H), 2.39-2.52 (m, 2H), 1.74-1.83 (m, 1H). $^{13}$C NMR (75 MHz, CDCl$_3$) δ 174.3, 158.7, 138.9, 138.3, 132.2, 129.3, 128.7, 128.6, 128.5, 128.4, 127.2, 126.4, 113.8, 67.1, 59.6, 59.2, 56.0, 55.3, 51.3, 39.7, 37.4, 35.6. MS (ESI) [M]⁺ 444.5.

(2S,4S)-1-[(3-Chlorophenyl)methyl]-4-{[(4-methoxyphenyl)methyl]amino}-N-(2-phenylethyl)pyrrolidine-2-carboxamide (77) was prepared according to the general procedure C as colorless oil (21%). $^1$H NMR (300 MHz, CDCl$_3$) δ 7.45 (t, J=5.18 Hz, 1H), 7.11-7.25 (m, 10H), 6.94 (d, J=6.97 Hz, 1H), 6.80-6.86 (m, 2H), 3.78 (s, 3H), 3.73 (d, J=13.37 Hz, 1H), 3.60 (d, J=5.65 Hz, 2H), 3.51-3.57 (m, 1H), 3.41-3.50 (m, 1H), 3.30 (d, J=13.56 Hz, 1H), 3.22-3.27 (m, 1H), 3.16 (dd, J=6.12, 9.51 Hz, 1H), 2.87 (d, J=10.36 Hz, 1H), 2.78 (dt, J=2.35, 6.92 Hz, 2H), 2.36-2.52 (m, 4H), 1.74-1.83 (m, 1H). $^{13}$C NMR (75 MHz, CDCl$_3$) δ 173.9, 158.9, 140.3, 138.8, 134.3, 131.3, 129.7, 129.5, 128.6, 128.6, 128.5, 127.4, 126.6, 126.5, 113.9, 67.3, 58.9, 55.8, 55.3, 51.1, 39.7, 37.2, 35.5. MS (ESI) [M]⁺ 478.3.

(2S,4S)-1-[(4-Chlorophenyl)methyl]-4-{[(4-methoxyphenyl)methyl]amino}-N-(2-phenylethyl)pyrrolidine-2-carboxamide (78) was prepared according to the general procedure C as colorless oil (19%). $^1$H NMR (300 MHz, CDCl$_3$) δ 7.43 (t, J=5.75 Hz, 1H), 7.10-7.26 (m, 10H), 6.94 (d, J=8.29 Hz, 2H), 6.81-6.86 (m, 2H), 3.75-3.82 (m, 5H), 3.60-3.74 (m, 3H), 3.48-3.60 (m, 4H), 3.26-3.33 (m, 1H), 3.19-3.25 (m, 1H), 3.13-3.18 (m, 1H), 2.67-2.90 (m, 4H), 2.35-2.50 (m, 2H), 1.77 (ddd, J=3.49, 5.13, 13.42 Hz, 1H). $^{13}$C NMR (75 MHz, CDCl$_3$) δ 174.1, 158.8, 138.8, 136.7, 132.9, 132.1, 130.1, 129.8, 129.3, 129.2, 129.1, 128.9, 128.8, 128.7, 128.6, 128.6, 128.5, 126.5, 113.9, 113.8, 67.2, 59.1, 58.8, 56.0, 55.3, 51.3, 39.6, 37.4, 35.5. MS (ESI) [M]⁺ 478.5.

(2S,4S)-1-[(2-Methoxyphenyl)methyl]-4-{[(4-methoxyphenyl)methyl]amino}-N-(2-phenylethyl)pyrrolidine-2-carboxamide (79) was prepared according to the general procedure C as colorless oil (25%). $^1$H NMR (300 MHz, CDCl$_3$) δ 7.82 (t, J=5.84 Hz, 1H), 7.28 (d, J=1.70 Hz, 1H), 7.13-7.24 (m, 7H), 7.10 (dd, J=1.51, 7.35 Hz, 1H), 6.80-6.92 (m, 4H), 3.87 (d, J=12.81 Hz, 1H), 3.77 (s, 3H), 3.72 (s, 3H), 3.51-3.65 (m, 3H), 3.32-3.44 (m, 2H), 3.15-3.24 (m, 2H), 2.85 (d, J=10.17 Hz, 1H), 2.77 (dt, J=1.98, 7.21 Hz, 2H), 2.42-2.54 (m, 2H), 1.82 (ddd, J=3.30, 5.75, 13.56 Hz, 1H). $^{13}$C NMR (75 MHz, CDCl$_3$) δ 173.4, 157.7, 156.6, 138.1, 131.2, 129.6, 128.3, 127.7, 127.6, 127.5, 125.4, 125.3, 119.5, 112.8, 109.5, 65.8, 58.2, 54.8, 54.3, 54.2, 53.6, 50.2, 39.2, 36.4, 34.9. MS (ESI) [M]⁺ 474.6.

(2S,4S)-1-[(3-Methoxyphenyl)methyl]-4-{[(4-methoxyphenyl)methyl]amino}-N-(2-phenylethyl)pyrrolidine-2-carboxamide (80) was prepared according to the general procedure C as colorless oil (45%). $^1$H NMR (300 MHz, CDCl$_3$) δ 7.54 (br. s., 1H), 7.31 (d, J=8.48 Hz, 2H), 7.10-7.24 (m, 6H), 6.69-6.87 (m, 4H), 3.80-3.90 (m, 3H), 3.75 (d, J=15.82 Hz, OH), 3.01-3.65 (m, 6H), 2.74-2.87 (m, 2H), 2.34-2.52 (m, 2H), 1.87-2.04 (m, 2H). $^{13}$C NMR (75 MHz, CDCl$_3$) δ 171.3, 157.7, 157.5, 136.5, 128.8, 127.3, 126.6, 126.3, 124.2, 122.9, 122.6, 118.9, 112.2, 110.9, 107.3, 64.1, 56.0, 54.2, 53.1, 53.1, 52.7, 47.2, 38.1, 33.1, 32.5. MS (ESI) [M]$^+$ 474.9.

(2S,4S)-1-[(3,4-Dimethoxyphenyl)methyl]-4-{[(4-methoxyphenyl)methyl]amino}-N-(2-phenylethyl)pyrrolidine-2-carboxamide (81) was prepared according to the general procedure C as colorless oil (55%). $^1$H NMR (300 MHz, CDCl$_3$) δ 7.02-7.26 (m, 3H), 6.80-6.94 (m, 6H), 6.46-6.79 (m, 2H), 3.83-3.91 (m, 12H), 3.75-3.79 (m, 2H), 3.43-3.73 (m, 2H), 2.95-3.33 (m, 1H), 2.68-2.91 (m, 2H), 1.68-2.50 (m, 4H). $^{13}$C NMR (75 MHz, CDCl$_3$) δ 172.1, 146.8, 146.2, 131.4, 127.0, 126.8, 126.4, 126.3, 126.2, 126.1, 124.0, 118.4, 117.0, 111.5, 111.5, 108.8, 108.2, 62.7, 56.6, 53.6, 53.5, 52.9, 49.6, 48.9, 37.6, 35.0, 33.2, 30.7. MS (ESI) [M]$^+$ 504.7.

(2S,4S)-4-{[(4-Methoxyphenyl)methyl]amino}-1-[(2-methylphenyl)methyl]-N-(2-phenylethyl)pyrrolidine-2-carboxamide (82) was prepared according to the general procedure C as colorless oil (19%). $^1$H NMR (300 MHz, CDCl$_3$) δ 7.36 (t, J=5.75 Hz, 1H), 7.12-7.19 (m, 7H), 7.07-7.11 (m, 2H), 6.84 (d, J=8.48 Hz, 2H), 3.75-3.80 (m, 4H), 3.51-3.70 (m, 5H), 3.45-3.50 (m, 1H), 3.29-3.38 (m, 1H), 3.17-3.28 (m, 2H), 2.95 (d, J=9.98 Hz, 1H), 2.67 (dt, J=2.73, 7.02 Hz, 2H), 2.42-2.51 (m, 2H), 2.21-2.27 (m, 3H), 2.19 (d, J=3.01 Hz, 1H), 1.74-1.82 (m, 1H). $^{13}$C NMR (75 MHz, CDCl$_3$) δ 172.2, 156.5, 136.6, 134.3, 134.0, 129.9, 128.0, 127.1, 126.9, 126.5, 126.4, 126.3, 124.9, 124.1, 123.8, 111.6, 111.6, 65.6, 57.4, 55.4, 53.9, 53.0, 49.1, 37.5, 35.2, 33.3, 16.9. MS (ESI) [M]$^+$ 458.4.

(2S,4S)-4-{[(4-Methoxyphenyl)methyl]amino}-1-[(4-methylphenyl)methyl]-N-(2-phenylethyl)pyrrolidine-2-carboxamide (83) was prepared according to the general procedure C as colorless oil (26%). $^1$H NMR (300 MHz, CDCl$_3$) δ 7.48 (t, J=5.84 Hz, 1H), 7.13-7.25 (m, 6H), 7.07 (d, J=7.91 Hz, 2H), 6.92-6.98 (m, 2H), 6.81-6.86 (m, 2H), 3.78 (s, 3H), 3.72 (d, J=13.00 Hz, 1H), 3.57 (d, J=3.77 Hz, 2H), 3.46-3.54 (m, 2H), 3.33 (d, J=13.00 Hz, 1H), 3.22 (d, J=3.20 Hz, 1H), 3.17 (dd, J=6.03, 9.61 Hz, 1H), 2.87 (d, J=10.17 Hz, 1H), 2.76 (dt, J=4.43, 6.92 Hz, 2H), 2.39-2.50 (m, 2H), 2.33 (s, 3H), 1.73-1.82 (m, 1H). $^{13}$C NMR (75 MHz, CDCl$_3$) δ 173.1, 157.5, 137.7, 135.6, 133.9, 130.8, 128.1, 127.8, 127.4, 127.3, 127.2, 125.2, 112.6, 65.8, 58.0, 57.8, 54.8, 54.0, 50.0, 38.5, 36.1, 34.4, 19.8. MS (ESI) [M]$^+$ 458.4.

(2S,4S)-1-[(4-Hydroxyphenyl)methyl]-4-{[(4-methoxyphenyl)methyl]amino}-N-(2-phenylethyl)pyrrolidine-2-carboxamide (84) was prepared according to the general procedure C as colorless oil (9%). $^1$H NMR (300 MHz, CDCl$_3$) δ 7.50 (t, J=5.56 Hz, 1H), 7.12-7.23 (m, 7H), 6.80-6.89 (m, 4H), 6.60 (d, J=8.29 Hz, 2H), 3.74 (s, 3H), 3.61-3.70 (m, 3H), 3.50 (td, J=7.18, 14.46 Hz, 2H), 3.31 (s, 1H), 3.21 (d, J=13.00 Hz, 1H), 3.09 (dd, J=6.40, 9.42 Hz, 1H), 2.92 (d, J=10.36 Hz, 1H), 2.69-2.85 (m, 3H), 2.36-2.48 (m, 2H), 1.83 (dd, J=4.24, 13.47 Hz, 1H). $^{13}$C NMR (75 MHz, CDCl$_3$) δ 174.1, 159.5, 155.7, 138.7, 130.2, 129.9, 129.0, 128.7, 128.6, 128.6, 126.5, 115.4, 114.2, 66.5, 58.2, 57.8, 55.4, 55.2, 50.3, 40.0, 35.6, 35.4. MS (ESI) [M]$^+$ 460.5.

(2S,4S)-1-{[4-(Dimethylamino)phenyl]methyl}-4-{[(4-methoxyphenyl)methyl]amino}-N-(2-phenylethyl)pyrrolidine-2-carboxamide (85) was prepared according to the general procedure C as colorless oil (3%). $^1$H NMR (300 MHz, CDCl$_3$) δ 7.37 (br. s., 1H), 7.28 (d, J=1.88 Hz, OH), 7.15-7.22 (m, 4H), 6.95 (d, J=8.67 Hz, 1H), 6.82-6.86 (m, 1H), 6.63 (d, J=8.67 Hz, 1H), 3.78 (s, 2H), 3.61-3.69 (m, 2H), 3.44-3.52 (m, 1H), 3.32 (d, J=12.81 Hz, 1H), 3.25 (d, J=5.09 Hz, 1H), 3.15 (d, J=5.84, 9.61 Hz, 1H), 2.89-2.97 (m, 5H), 2.76 (td, J=3.49, 6.97 Hz, 2H), 2.46-2.53 (m, 1H), 2.36-2.45 (m, 1H), 1.81 (s, 1H). $^{13}$C NMR (75 MHz, CDCl3) δ 172.6, 148.1, 137.1, 127.8, 127.7, 126.9, 126.7, 124.6, 124.0, 112.1, 110.7, 64.7, 56.9, 54.1, 53.4, 49.1, 38.8, 38.1, 35.0, 33.8, 29.0. MS (ESI) [M]$^+$ 487.6.

(2S,4S)-1-[(4-Cyanophenyl)methyl]-4-{[(4-methoxyphenyl)methyl]amino}-N-(2-phenylethyl)pyrrolidine-2-carboxamide (86) was prepared according to the general procedure C as colorless oil (27%). $^1$H NMR (300 MHz, CDCl$_3$) δ 7.52 (d, J=8.29 Hz, 2H), 7.44 (t, J=5.75 Hz, 1H), 7.08-7.25 (m, 9H), 6.84 (d, J=8.67 Hz, 2H), 3.75-3.82 (m, 4H), 3.50-3.65 (m, 4H), 3.38 (d, J=13.75 Hz, 1H), 3.23-3.29 (m, 1H), 3.20 (dd, J=5.93, 9.70 Hz, 1H), 2.70-2.89 (m, 3H), 2.42-2.51 (m, 1H), 2.37 (dd, J=5.65, 9.98 Hz, 1H), 1.73-1.83 (m, 1H). $^{13}$C NMR (75 MHz, CDCl3) δ 228.8, 173.8, 158.8, 143.8, 138.8, 132.2, 129.3, 128.9, 128.7, 128.6, 126.5, 113.9, 67.5, 59.2, 59.1, 56.1, 55.3, 51.4, 39.5, 37.4, 35.4. MS (ESI) [M]$^+$ 469.4.

(2S,4S)-4-{[(4-Methoxyphenyl)methyl]amino}-1-(naphthalen-2-ylmethyl)-N-(2-phenylethyl)pyrrolidine-2-carboxamide (87) was prepared according to the general procedure C as colorless oil (23%). $^1$H NMR (300 MHz, CDCl$_3$) δ 7.80-7.84 (m, 1H), 7.72-7.79 (m, 2H), 7.58 (s, 1H), 7.43-7.55 (m, 3H), 7.10-7.24 (m, 8H), 6.82 (d, J=8.67 Hz, 2H), 3.93 (d, J=13.00 Hz, 1H), 3.77 (s, 3H), 3.43-3.59 (m, 5H), 3.21-3.29 (m, 2H), 2.89 (d, J=10.17 Hz, 1H), 2.76 (dt, J=3.20, 6.88 Hz, 2H), 2.42-2.55 (m, 2H), 1.80 (ddd, J=3.49, 5.65, 13.47 Hz, 1H). $^{13}$C NMR (75 MHz, CDCl3) δ 172.5, 157.1, 137.2, 134.1, 131.7, 131.1, 130.1, 127.7, 127.0, 126.9, 126.5, 126.1, 126.0, 125.4, 125.0, 124.8, 124.5, 124.1, 112.2, 65.6, 58.1, 57.4, 54.2, 53.6, 49.5, 38.1, 35.7, 33.9. MS (ESI) [M]$^+$ 494.4.

(2S,4S)-1-(2H-1,3-Benzodioxol-5-ylmethyl)-4-{[(4-methoxyphenyl)methyl]amino}-N-(2-phenylethyl)pyrrolidine-2-carboxamide (88) was prepared according to the general procedure C as colorless oil (11%). $^1$H NMR (300 MHz, CDCl$_3$) δ 7.35 (br. s., 1H), 7.14-7.25 (m, 7H), 6.84 (d, J=8.67 Hz, 2H), 6.69 (d, J=7.91 Hz, 1H), 6.59 (s, 1H), 6.53 (d, J=7.72 Hz, 1H), 5.92 (d, J=2.07 Hz, 2H), 3.78 (s, 3H), 3.61-3.70 (m, 3H), 3.51 (td, J=6.64, 13.09 Hz, 2H), 3.27 (d, J=13.00 Hz, 2H), 3.13 (dd, J=5.84, 9.61 Hz, 1H), 2.92 (d, J=10.93 Hz, 1H), 2.79 (dt, J=3.77, 6.97 Hz, 2H), 2.37-2.49 (m, 2H), 1.82 (d, J=16.39 Hz, 2H). $^{13}$C NMR (75 MHz, CDCl$_3$) δ 172.7, 146.3, 145.4, 137.4, 130.5, 128.3, 127.3, 127.2, 125.1, 120.3, 112.6, 107.6, 106.7, 99.5, 97.0, 65.4, 57.6, 57.1, 54.4, 53.9, 49.4, 38.4, 35.2, 34.1. MS (ESI) [M]$^+$ 488.6.

Calcium mobilization assay. Two individual stable cell lines were created by over-expressing human NPFFR1 and NPFFR2 receptors in CHO-RD-HGA16 (Molecular Devices) cells. The day before the assay, cells were plated into 96-well black-walled assay plates at 30,000 cells/well (100 µL volume) in Ham's F12 supplemented with 10% fetal bovine serum, 100 units of penicillin/streptomycin, and 100 g/mL normocin™.

The cells were incubated overnight at 37° C., 5% CO$_2$. Prior to the assay, Calcium 5 dye (Molecular Devices) was reconstituted according to the manufacturer instructions. The reconstituted dye was diluted 1:40 in warm assay buffer (1× HBSS, 20 mM HEPES, 2.5 mM probenecid, pH 7.4 at 37° C.). Growth medium was removed and the cells were gently washed with 100 µL of warm assay buffer. The cells were incubated for 45 minutes at 37° C., 5% CO$_2$ in 200 µL of the diluted Calcium 5 dye. A single concentration of each test compound was prepared at 10× the desired final concentration in 2.25% BSA/8% DMSO/assay buffer. Serial dilutions of NPFF were prepared at 10× the desired final concentration in 0.25% BSA/1% DMSO/assay buffer, aliquoted into 96-well polypropylene plates, and warmed to 37° C. After the dye-loading incubation period, the cells were pre-treated with 25 μL of the test compounds and incubated for 15 min at 37° C. After the pre-treatment incubation period, the plate was read with a FlexStation® II (Molecular Devices). Calcium-mediated changes in fluorescence were monitored every 1.52 seconds over a 60 second time period, with the FlexStation® II adding 25 μL of the NPFF serial dilutions at the 19 second time point (excitation at 485 nm, detection at 525 nm). Peak kinetic reduction (SoftMax, Molecular Devices) relative fluorescent units (RFU) were plotted against the log of compound concentration.

Data were fit to a three-parameter logistic curve to generate $EC_{50}$ values (GraphPad Prism, GraphPad Software, Inc., San Diego, CA). Apparent $K_e$ values were calculated using the equation $K_e=[L]/((EC_{50}^+/EC_{50}^-)-1)$ where [L] is the concentration of test compound, $EC_{50}^+$ is the $EC_{50}$ of NPFF with test compound, and $EC_{50}^-$ is the $EC_{50}$ of NPFF alone. $K_e$ values were considered valid when the $EC_{50}^+/EC_{50}^-$ ratio was at least 4.

384-Well High Throughput Screening

Stable human NPFFR1 CHO-RD-HGA16 cells were plated in 30 μL/well volume at 5,000 cells/well in Ham's F12 medium supplemented with 1% FBS and 100 units penicillin/streptomycin in 384-well Greiner μClear® black walled microplates using a MicroFlo™ Select dispenser fitted with a 5 μL cassette (BioTek). The plated cells were incubated overnight at 37° C., 5% CO2, 95% relative humidity. The next day, compound test plates were prepared by diluting previously replicated library daughter plates with assay buffer to achieve a 100 μM (10× desired final concentration) working solution and filling columns 1, 2, 23, and 24 with positive and negative controls. An additional compound test plate containing the NPFF $EC_{60}$ concentration (250 nM prepared at 10× the desired final concentration in 1% DMSO/assay buffer) was prepared for the antagonist portion of the screen. Calcium 5 dye (Bulk Kit, Molecular Devices), reconstituted according to the manufacturer's instructions, was diluted 1:20 in pre-warmed (37° C.) assay buffer (1× HBSS, 20 mM HEPES, 2.5 mM probenecid, pH 7.4 at 37° C.) and 30 μL was added to the plate with the Biomek NX, which was then incubated for 45 minutes at 37° C., 5% $CO_2$, 95% relative humidity. Using the Biomek NX, the dye loaded plate was pretreated with 8.5 μL of 8% DMSO/assay buffer and incubated for 15 minutes at 37° C., 5% $CO_2$, 95% relative humidity. After this incubation period, the plate was read with the Tetra to evaluate agonist activity. Calcium-mediated changes in fluorescence were monitored every 1 second over a 60 second time period, with the Tetra adding 8.5 μL from the compound plate at the 10 second time point (excitation at 470-495 nm, detection at 515-575 nm). The cell plate was then incubated for another 15 minutes at 37° C., 5% $CO_2$, 95% relative humidity after which it was read with the Tetra to evaluate antagonist activity. Calcium-mediated changes in fluorescence were monitored every 1 second over a 60 second time period, with the Tetra adding 8.5 μL from the NPFF $EC_{60}$ plate at the 10 second time point (excitation at 470-495 nm, detection at 515-575 nm). Data was exported from ScreenWorks (Molecular Devices) using the response over baseline (ROB) statistic which presents data as a fold-response compared with the baseline sample. Percent inhibition was calculated using the equation (1−(cmpd ROB/NPFF $EC_{60}$ ROB))×100.

cAMP assay. Stable human NPFFR1-CHO (ES-491-C) and NPFFR2-CHO (ES-490-C) cell lines were purchased from PerkinElmer and used with the Lance@ Ultra kit (TRF0262) to detect cAMP accumulation in low volume 96-well plates. Stimulation buffer containing 1× HBSS, 5 mM HEPES, 0.1% BSA stabilizer, and 0.5 mM IBMX was prepared and titrated to 7.4 at room temperature. Serial dilutions of the agonist control NPFF were prepared at 8× the desired final concentration in 2% DMSO/stimulation buffer and 2.5 μL was added to the assay plate.

A single concentration of each test compound was prepared at 4× the desired final concentration in 2% DMSO/stimulation buffer and 5 μL was added to the assay plate. The $EC_{50}$ concentration of forskolin (1 μM) was prepared at 8× in 2% DMSO/stimulation buffer and 2.5 μL was added to the assay plate.

Cells were lifted with versene and spun at 270 g for 10 minutes. The cell pellet was resuspended in stimulation buffer and 4,000 cells (10 μL) were added to each well. After incubating for 30 min at RT, Eu-cAMP tracer and uLIGHT-anti-cAMP working solutions were added per the manufacturer's instructions. After incubation at RT for 1 hour, the TR-FRET signal (ex 337 nm) was read on a CLARIOstar multimode plate reader (BMG Biotech, Cary NC).

Fluorescence values at 665 nm were plotted against the log of compound concentration using a nonlinear regression analysis to generate $EC_{50}$ values (GraphPad Prism, GraphPad Software, Inc., San Diego CA). $K_e$ values were calculated using the same equation as described in the calcium mobilization methods.

Radioligand binding assay. Binding assays were performed according to PerkinElmer's protocol in a final volume of 500 μL of assay buffer (50 mM Tris-HCl, 1 mM $MgCl_2$, 60 mM NaCl, 0.5% BSA, pH 7.4). For NPFF1, the assay mixture contained 25 μL of 0.065 nM [$^{125}$I]NPFF (PerkinElmer, $K_D$=0.11 nM, NEX381), 25 μL of test compounds (prepared at 8× the final desired concentration in 8% DMSO/assay buffer), and 150 μL of CHO-hNPFFR1 membranes (1 μg protein/well, PerkinElmer, RBHNF1M400UA). Specific binding was defined as the difference between [$^{125}$I]NPFF binding in the absence and presence of 100 nM final nonradiolabeled NPFF. After incubating at 27° C. for 120 minutes, the binding assay was terminated by vacuum filtration onto Unifilter GF/C glass-fiber filters (pre-soaked in 0.1% PEI) using a Brandel (Gaithersburg, MD, USA) 96-well harvester, followed by three washes with ice-cold wash buffer (50 mM Tris-HCl, 0.1% BSA, pH 7.4). The filter plate was dried for 1 hr at 55° C. Microscint 20 (50 μL) was added to each well and filter-bound radioactivity was counted on a Packard Top-Count NXT microplate scintillation and luminescence counter. Percentage of specific [$^{125}$I]NPFF binding was plotted against the log of compound concentration.

Data were fit to a one site (fit Ki) competitive binding model, log EC50=log(10^log Ki*(1+RadioligandNM/HotKdNM)), to generate Ki values for the test compounds using GraphPad Prism (GraphPad Software, Inc., San Diego CA). NPFF2 binding assays were conducted with the same protocol, except that 0.1 nM [$^{125}$I]NPFF (PerkinElmer, $K_D$=0.15 nM, NEX381) and CHO-hNPFFR2 membranes (1 μg protein/well, PerkinElmer, RBHNF2M400UA) were used.

Kinetic solubility assay. A 10 μL of test compound stock solution (10 mM DMSO) was combined with 490 μL of PBS (potassium phosphate monobasic 1 mM, sodium phosphate dibasic 3 mM and sodium chloride 155 mM buffer). The solution was agitated on a VX-2500 multi-tube vortexer (VWR) for 2 hours at room temperature. Following agitation, the sample was filtrated on a glass-fiber filter (1 μm) and the eluate was diluted 200-fold with a mixture of acetonitrile: water (1:1). On each experimental occasion, nicardipine and imipramine were assessed as reference compounds for low and high solubility, respectively. All samples were assessed in triplicate and analyzed by LC-MS/MS using electrospray ionization against standards prepared in the same matrix.

Bidirectional MDCK-MDR1 permeability assay. MDCK-mdr1 cells at passage 5 were seeded onto permeable polycarbonate supports in 12-well Costar@ Transwell® plates and allowed to grow and differentiate for 3 days. On day 3, culture medium (DMEM supplemented with 10% FBS) was removed from both sides of the transwell inserts and cells were rinsed with warm HBSS. After the rinse step, the chambers were filled with warm transport buffer (HBSS containing 10 mM HEPES, 0.25% BSA, pH 7.4) and the plates were incubated at 37° C. for 30 min prior to TEER (Trans Epithelial Electric Resistance) measurements.

The buffer in the donor chamber (apical side for A-to-B assay, basolateral side for B-to-A assay) was removed and replaced with the working solution (10 µM test article in transport buffer). The plates were then placed at 37° C. under light agitation. At designated time points (30, 60 and 90 min), an aliquot of transport buffer from the receiver chamber was removed and replenished with fresh transport buffer. Samples were quenched with ice-cold ACN containing internal standard and then centrifuged to pellet protein. Resulting supernatants are further diluted with 50/50 ACN/H$_2$O(H$_2$O only for Atenolol) and submitted for LC-MS/MS analysis. Reported apparent permeability (Papp) values were calculated from single determination. Atenolol and propranolol were tested as low and moderate permeability references. Bidirectional transport of digoxin was assessed to demonstrate Pgp activity/expression.

The apparent permeability (Papp, measured in cm/s) of a compound is determined according to the following formula:

$$Papp = \frac{(dQ)/(dt)}{A * C * 60}$$

dQ/dt is the net rate of appearance in the receiver compartment
A is the area of the Transwell measured in cm$^2$ (1.12 cm$^2$)
Ci is the initial concentration of compound added to the donor chamber
60 is the conversion factor for minutes to seconds.

In Vivo Pharmacology.

Animals. Adult male (n=18) Sprague-Dawley rats (Harlan, Indianapolis, IN) weighing 225-300 g were individually housed on a 12/12-hour light/dark cycle with behavioral experiments conducted during the light period. Rats had free access to food and water except during test sessions, and were maintained and experiments were conducted in accordance with guidelines of the International Association for the Study of Pain (Zimmermann, M., *Ethical guidelines for investigations of experimental pain in conscious animals*, Pain, 16, 109-110, 1983) and with the 2011 Guide for the Care and Use of Laboratory Animals (Institute of Laboratory Animal Resources on Life Sciences, National Research Council, National Academy of Sciences, Washington, DC), and were approved by the Institutional Animal Care and Use Committee, University at Buffalo, the State University of New York (Buffalo, NY).

Drugs. Fentanyl was purchased from Sigma-Aldrich (St. Louis, MO), dissolved in 0.9% saline, and injected subcutaneously in a volume of 1 ml/kg. Compounds 16 and 33 were dissolved in a vehicle of 20% dimethyl sulfoxide in saline and injected intraperitoneally in a volume of 1 ml/kg.

Fentanyl-induced hyperalgesia. Nociceptive thresholds were measured using calibrated von Frey filaments (1.4-26 g; North Coast Medical, Morgan Hill, CA). Rats (n=6 per group) were placed in elevated plastic chambers with a wire mesh floor (IITC Life Science Inc., Woodland Hills, CA) and allowed to habituate prior to testing. Filaments were applied perpendicularly to the medial plantar surface of the hind paw from below the mesh floor in an ascending order of filament force, beginning with the lowest filament. Filaments were applied until buckling occurred for approximately two seconds. Mechanical paw withdrawal thresholds (PWTs) correspond to the lowest force that elicited a withdrawal of the hind paw in at least two out of three applications. Forces larger than 26 g would physically elevate the non-CFA-treated paw and did not reflect pain-like behavior.

After a nociceptive baseline was established for each rat on day prior to and the day of fentanyl treatment (D$_1$ and D$_0$), four subcutaneous injections of 0.06 mg/kg fentanyl each were injected at 15 min intervals for a total dose of 0.24 mg/kg. In one group of rats, PWT measurements were taken on days 1-5 to monitor the onset of and recovery from the fentanyl-induced hyperalgesia. In the other two groups of rats, antinociceptive dose-effect curves for compounds 16 and 33 were established on day 1 using a multi-cycle cumulative dosing procedure, in which measurements were taken immediately prior to drug administration then 30 min after drug administration before the next injection, and continued for doses ranging from 3.2-32 mg/kg.

Data analysis. PWTs were averaged within each group and plotted as a function of dose. Repeated measures one-way ANOVAs, with time or treatment entered as the within-subject factor, followed by Bonferroni's post-hoc test were used to determine the statistical significances. P<0.05 was considered statistically significant for all tests.

Pharmacological Evaluation of Compounds 16 and 33

Compounds 16 and 33 were identified as potent NPFF1 antagonists, and selected for further characterization and assessment.

Figure 4:
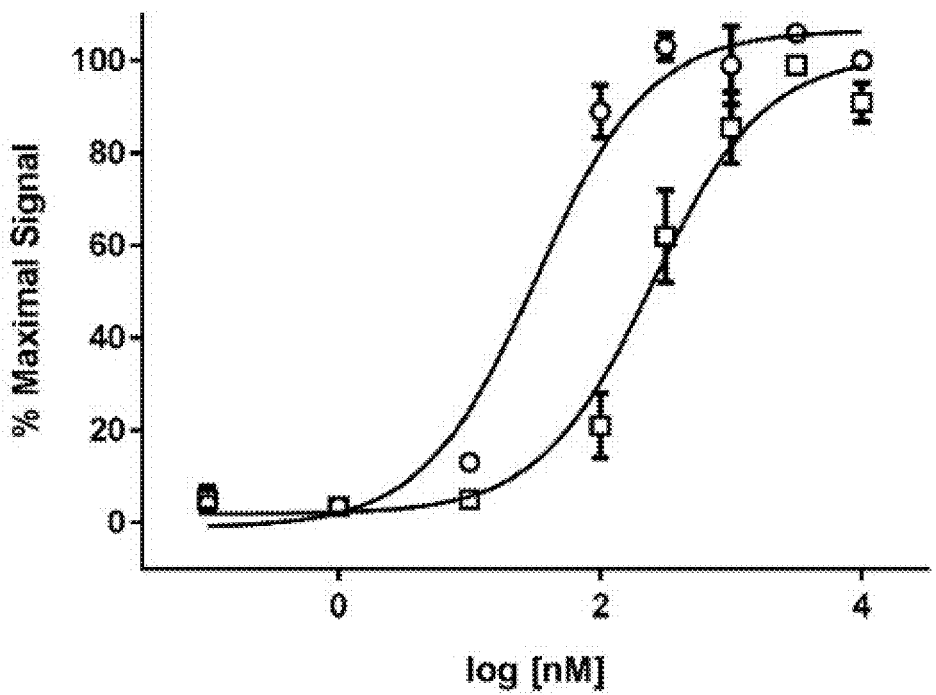
FIG. 4 shows concentration-response curves of compound 16 in the NPFF1 and NPFF2 calcium mobilization assays, with graph A showing the antagonist activity of compound 16 in the NPFF1 calcium mobilization functional $K_e$ assay, for NPFF alone (○) and NPFF+5 µM final 16 (□) in stable NPFF1-RD-HGA16 cells, and with graph B showing the antagonist activity of compound 16 in the NPFF2 calcium mobilization functional $K_e$ assay, for NPFF alone (○) and NPFF+10 µM final 16 (□) in stable NPFF2-RD-HGA16 cells.
Figure 4:
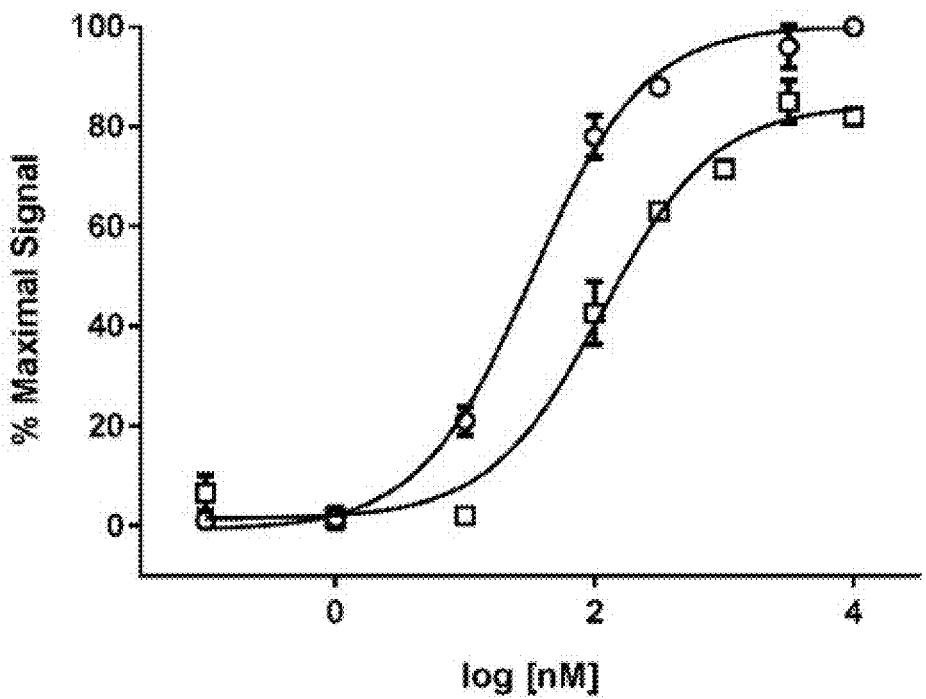

The concentration-response curve of compound 16 in the NPFF1 and NPFF2 calcium mobilization assays is shown in FIG. 4, in which graph A shows the antagonist activity of compound 16 in the NPFF1 calcium mobilization functional K$_e$ assay, and graph B shows the antagonist activity of compound 16 in the NPFF2 calcium mobilization functional K$_e$ assay. Graph A shows the concentration-response curves of NPFF alone (○) and NPFF+5 µM final 16 (□) in stable NPFF1-RD-HGA16 cells. Graph B shows the concentration-response curves of NPFF alone (○) and NPFF+10 µM final 16 (□) in stable NPFF2-RD-HGA16 cells. The right shift of the NPFF curve in the presence of the test compound was used to calculate K$_e$ values. Representative data from one experiment are shown and each data point is mean±SD of duplicate determinations.

Figure 5:
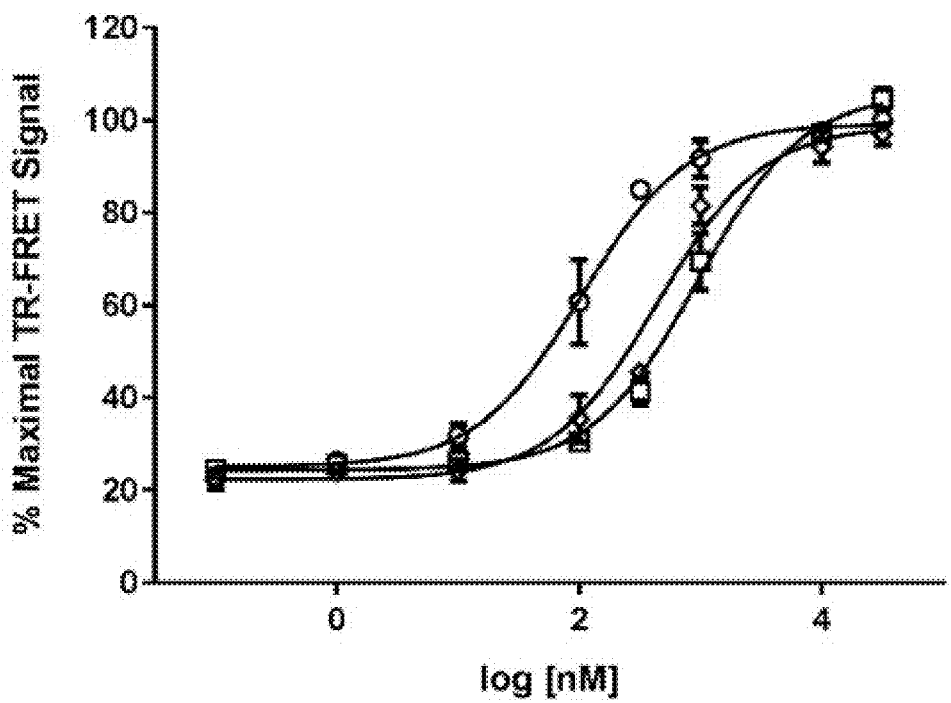
FIG. 5 shows concentration-response curves of compounds 16 and 33 in the NPFF1 and NPFF2 cAMP assays, with graph A showing the antagonist activity of compounds 16 and 33 in the NPFF1 cAMP functional $K_e$ assay, for NPFF alone (○), NPFF+4 µM final 16 (□), and NPFF+2 µM final 33 (◇) in stable NPFF1-CHO cells, and with graph B showing the antagonist activity of compounds 16 and 33 in the NPFF2 cAMP functional $K_e$ assay, for NPFF alone (○), NPFF+10 µM final 16 (□), and NPFF+10 µM final 33 (◇) in stable NPFF2-CHO cells.
Figure 5:
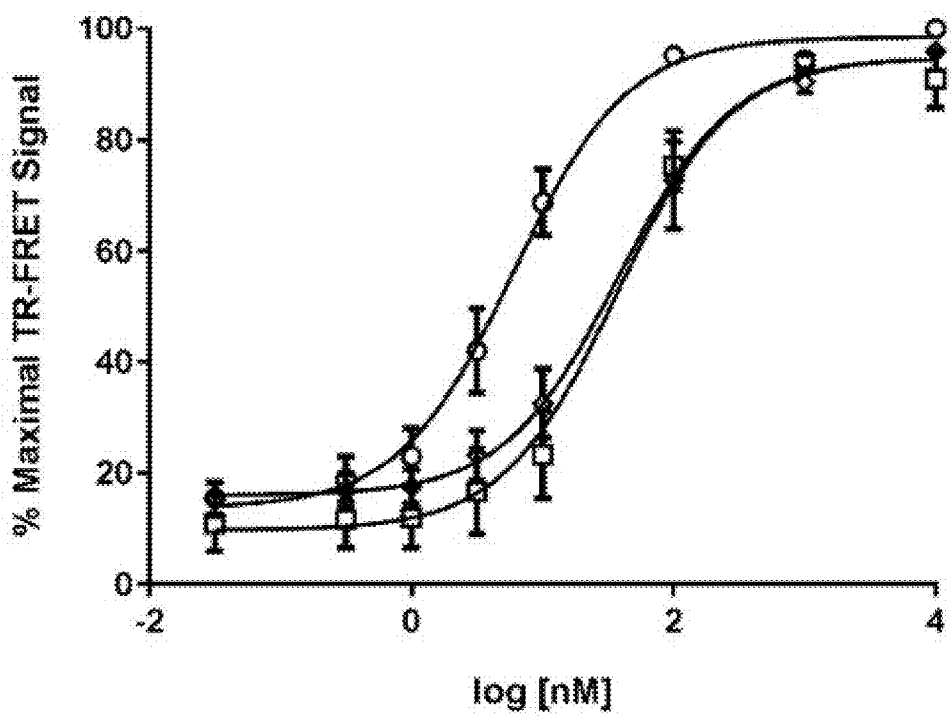

The concentration-response curves of compounds 16 and 33 in the NPFF1 and NPFF2 cAMP assays are shown in FIG. 5, in which graph A shows the antagonist activity of compounds 16 and 33 in the NPFF1 cAMP functional K$_e$ assay, and graph B shows the antagonist activity of compounds 16 and 33 in the NPFF2 cAMP functional K$_e$ assay. Graph A shows the concentration-response curves of NPFF alone (○), NPFF+4 µM final 16 (□), and NPFF+2 µM final 33 (◇) in stable NPFF1-CHO cells. Graph B shows the concentration-response curves of NPFF alone (○), NPFF+10 µM final 16 (□), and NPFF+10 µM final 33 (◇) in stable NPFF2-CHO cells. The right shift of the NPFF curve in the presence of the test compound was used to calculate $K_e$ values. Each data point is mean±SEM of at least N=3 conducted in duplicate.

In the cAMP assay, the NPFF+16 curve had a Hill slope of 1.3 in both NPFF1 and NPFF2 cells while the NPFF+33 curve had a Hill slope of 1.4 and 1 in NPFF1 and NPFF2 cells, respectively, thus indicating that the activity of these compounds is not due to the formation of aggregates. These results correlate with those from the calcium mobilization assays where the NPFF+16 curve had a Hill slope of 1.7 and 1.1 in NPFF1 and FF2 cells, respectively, and the NPFF+33 curve had a Hill slope of 1.4 in both cell lines.

Table 6 below sets out selected physicochemical and preliminary ADME (absorption, distribution, metabolism, and excretion) properties determined for compounds 1, 16, and 33.

TABLE 6

| Parameter | Desired value | Compound 1 | Compound 16 | Compound 33 |
|---|---|---|---|---|
| Molecular weight | <500 | 418 | 444 | 523 |
| ClogP | 1-4 | 3.57 | 4.59 | 4.37 |
| PSA | <70 | 69.7 | 53.6 | 54.4 |
| PKa | <8 | 8.6, 5.0 | 9.1, 4.8 | 9.1, 4.8 |
| HBD | <3 | 2 | 2 | 2 |
| HBA | <7 | 4 | 5 | 8 |
| Solubility (μM) | >60 | N.D. | 146.8 ± 6.9 | 45.9 ± 7.7 |
| $P_{app}$ ($10^{-6}$ cm/sec) A-to-B | >2 | N.D. | 7.6 | 2.7 |
| $P_{app}$ ($10^{-6}$ cm/sec) B-to-A | | N.D. | 6.7 | 3.6 |
| Efflux ratio | <2.5 | N.D. | 0.9 | 1.3 |

HBD: H-bond donor;
HBA: H-bond acceptor.
N.D.: Not determined.

The compounds 16 and 33 were tested as free base forms in kinetic solubility and bidirectional MDCK-MDR1 permeability assays. As seen in Table 6, compound 16 was soluble in aqueous solutions, displaying a kinetic solubility of 146.8±6.9 μM (Mean±% CV) which falls in the range of compounds with good solubility, while compound 33 had a lower solubility of 45.9±7.7 μM, which is expected for a larger molecule with a higher molecular weight. Moreover, these compounds contain multiple protonable nitrogen atoms which can be converted to salt forms, to enhance solubility and bioavailability.

One of the major challenges for central nervous system (CNS) drugs is their ability to cross the blood-brain barrier (BBB) and reach the CNS. For the majority of drugs, the BBB permeability is affected by two factors: the ability to permeate through the BBB passively and the avoidance of being effluxed out by the transport proteins such as P-glycoprotein. Compounds 16 and 33 were evaluated in the bidirectional transport assay using MDCK-MDR1 cells which are stably transfected with human MDR1 cDNA and express a higher level of the P-glycoprotein (Pgp) compared to the wild type. Table 6 shows that compound 16 traversed the cell barrier from the apical (A) to basolateral (B) at a rate of $7.6 \times 10^{-6}$ cm/s, and the reverse direction B to A at a rate of $6.7 \times 10^{-6}$ cm/s, demonstrating a moderate BBB permeability (within the range of $3-6 \times 10^{-6}$ cm/s). Compound 33 is also able to penetrate the BBB albeit at lower permeability compared to compound 16. Both compounds were not Pgp substrates as indicated by the efflux ratio ($P_{B \to A}/P_{A \to B}$). Together, the data evidence the character of these compounds as CNS positive ligands.

Anti-Hyperalgesia Effects of Compounds 16 and 33 in Rats

Figure 6:
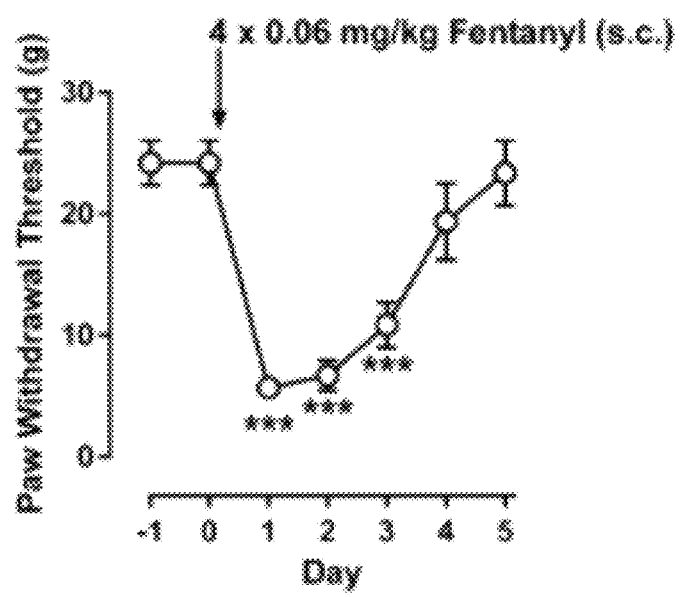
FIG. 6 shows the results of testing in a fentanyl-induced hyperalgesia model in rats, in which graph A shows results for fentanyl-induced mechanical hyperalgesia, and in which graph B shows the anti-hyperalgesic effects of compounds 16 and 33 (N=6 per group).
Figure 6:
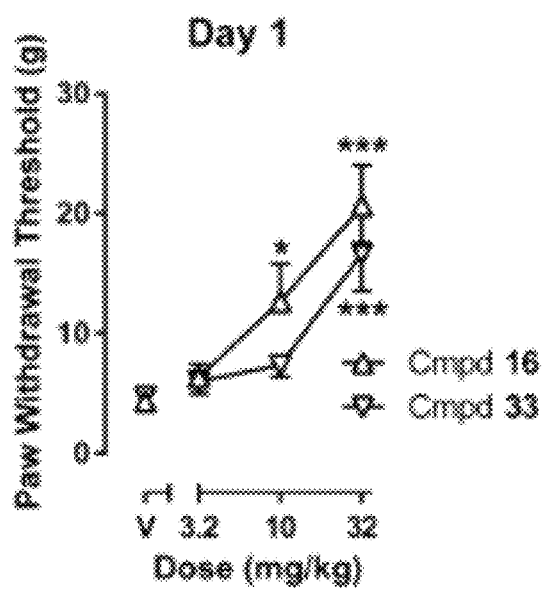

Compounds 16 and 33 were tested in a fentanyl-induced hyperalgesia model in rats, with the results shown in FIG. 6, in which graph A shows results for fentanyl-induced mechanical hyperalgesia, and graph B shows the anti-hyperalgesic effects of compounds 16 and 33 (N=6 per group). The ordinate in the graphs is paw withdrawal threshold, in grams, and the abscissa is time. P<0.05 compared to pre-fentanyl treatment (Day 0) or compared to "V" (vehicle) treatment.

Prior to fentanyl treatment, administered i.p., the test rats displayed a mean paw withdrawal threshold (PWT) of 24.2±1.8 g, which decreased to 5.7±0.8 g on day 1 after fentanyl administration. One-way repeated measures ANOVA, with time entered as the repeated measure factor, revealed a significant main effect of fentanyl treatment on paw withdrawal threshold ($F(6, 35)=23.42$, $p<0.0001$). Bonferroni's post hoc tests revealed significant differences on days 1-3 as compared to day 0.

Both compounds 16 and 33 dose-dependently increased PWT over a dose range of 3.2-32 mg/kg when tested on day 1, as shown in FIG. 6. Treatment with compound 16 produced a significant main effect as determined by one-way repeated measures ANOVA, with treatment entered as the within subject factor: $F(3, 20)=15.10$, $p<0.0001$. Additionally, Bonferroni's post hoc tests revealed significant differences at 10 and 32 mg/kg of 16 as compared to the vehicle. Similarly, treatment with compound 33 produced a significant main effect ($F(3, 20)=12.45$, $p<0.001$) and Bonferroni's post hoc tests revealed significant differences at 32 mg/kg of 33 as compared to the vehicle.

The foregoing results evidence the effectiveness of compounds 16 and 33 to reverse opioid-induced hyperalgesia in rats, as a model system for human response to such compounds.

The present disclosure therefore contemplates a neuropeptide FF receptor modulator comprising a compound according to Formula (I) herein, wherein $R_2$ is selected from —N—($C_2$-$C_5$alkyl)$_2$ and NH—$R_1$, wherein $R_1$ is selected from $C_2$-$C_9$ alkyl, heterocyclealkyl, cycloalkylalkyl, aminoalkyl, and arylalkyl; $R_3$ is selected from $C_3$-$C_9$ alkyl, aryl, heteroaryl, heterocycle, heteroarylalkyl, heterocyclealkyl, and arylalkyl; $R_4$ is selected from H and $C_1$-$C_2$ alkyl; and $R_5$ is selected from $C_3$-$C_9$ alkyl, heteroarylalkyl, heteroaryl, heterocyclealkyl, heterocycle, cycloalkylalkyl, and arylalkyl; or a pharmaceutically acceptable salt thereof. Such neuropeptide FF receptor modulator may be constituted with $R_2$ being NH—$R_1$, wherein $R_1$ is selected from $C_3$-$C_9$ alkyl, heterocyclealkyl, cycloalkylalkyl, aminoalkyl, and arylalkyl; for example, $R_1$ may be $C_3$-$C_6$ alkyl, or alternatively, $R_1$ may be phenethyl, substituted by lower alkoxy, nitro, lower alkyl, halogen or halogenated lower alkyl.

The neuropeptide FF receptor modulator may be constituted as comprising a compound of Formula II, wherein $R_2$ is selected from —N—($C_2$-$C_5$alkyl)$_2$; and X is S, SO, SO$_2$, O, NH or CH$_2$.

Alternatively, the neuropeptide FF receptor modulator may be constituted as comprising a compound of Formula IIA, wherein $R_1$ is selected from $C_2$-$C_9$ alkyl, heterocyclealkyl, cycloalkylalkyl, aminoalkyl, and arylalkyl; and X is S, SO, SO$_2$, O, NH or CH$_2$; for example, $R_1$ may be $C_3$-$C_6$ alkyl, benzyl or phenethyl, substituted or unsubstituted, and X may be oxygen. More specifically, $R_1$ may be $C_3$-$C_6$ alkyl, or $R_1$ may be phenethyl, substituted by lower alkoxy, nitro, lower alkyl, halogen or halogenated lower alkyl.

The neuropeptide FF receptor modulator may be constituted as comprising a compound of Formula III, wherein $R_3$ is selected from $C_3$-$C_9$ alkyl, aryl, heteroaryl, heterocycle, heteroarylalkyl, heterocyclealkyl, and arylalkyl; and $R_4$ is selected from H and $C_1$-$C_2$ alkyl. Such modulator may be constituted wherein $R_3$ is benzyl or substituted benzyl, phenethyl or substituted phenethyl, and $R_4$ is H. Alternatively, such modulator may be constituted wherein $R_3$ is benzyl mono-substituted by methoxy; and $R_4$ is H. As another alternative, such modulator may be constituted wherein $R_3$ is benzyl or substituted benzyl and $R_4$ is methyl. As a still further alternative, such modulator may be constituted wherein $R_3$ is $C_3$-$C_6$ alkyl.

The neuropeptide FF receptor modulator may be constituted as comprising a compound of Formula IV, wherein $R_5$ is selected from $C_3$-$C_9$ alkyl, heteroarylalkyl, heteroaryl, heterocyclealkyl, heterocycle, cycloalkylalkyl, and arylalkyl; and X is S, SO, $SO_2$, O, NH or $CH_2$. Such modulator may be constituted wherein $R_5$ is benzyl or substituted benzyl, e.g., wherein $R_5$ is monosubstituted benzyl and the substituents are halogen or methoxy at the 2- or 3-position.

The neuropeptide FF receptor modulator in another aspect may be constituted with the compound having the structure set out in Table 1 hereof, wherein $R_2$ is selected from the group consisting of the $R_2$ species set out in such table.

The neuropeptide FF receptor modulator in a further aspect may be constituted with the compound having the structure set out in Table 2 hereof, wherein $R_1$ is selected from the group consisting of the $R_1$ species set out in such table.

The neuropeptide FF receptor modulator in an additional aspect may be constituted with the compound having the structure set out in Table 3 hereof, wherein $R_3$ and $R_4$ are selected from the group consisting of the $R_3$ and $R_4$ species set out in such table.

The neuropeptide FF receptor modulator in yet another aspect may be constituted with the compound having the structure set out in Table 4 hereof, wherein $R_5$ is selected from the group consisting of the $R_5$ species set out in such table.

The neuropeptide FF receptor modulator in a further aspect may be constituted with the compound being

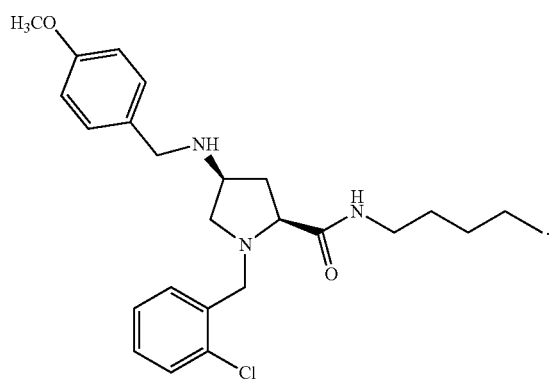 [SMILES: CCCCCNC(=O)[C@@H]1C[C@H](NCc2ccc(OC)cc2)CN1Cc1ccccc1Cl]

The neuropeptide FF receptor modulator in a still further aspect may be constituted with the compound being

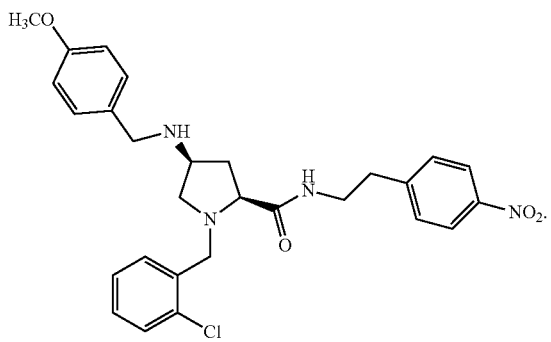 [SMILES: COc1ccc(CN[C@H]2C[C@@H](C(=O)NCCc3ccc([N+](=O)[O-])cc3)N(Cc3ccccc3Cl)C2)cc1]

The disclosure further contemplates a pharmaceutical composition comprising a neuropeptide FF receptor modulator as variously described herein, and a pharmaceutically acceptable carrier. The pharmaceutical composition may further comprise an opioid drug, e.g., at least one selected from the group consisting of fentanyl, morphine, oxycodone, hydrocodone, and buprenorphine. Alternatively, the pharmaceutical composition may further comprise an antipsychotic drug, e.g., at least one selected from the group consisting of haloperidol and aripiperazole. As a still further alternative, the pharmaceutical composition may further comprise a monoamine reuptake inhibitor, e.g., at least one selected from the group consisting of fluoxetine and sertraline.

The disclosure also contemplates a method for treating a subject having or susceptible to a condition or disorder where modulation of neuropeptide FF receptor activity is of therapeutic benefit, comprising administering to the subject having or susceptible to such condition or disorder a therapeutically effective amount of a neuropeptide FF receptor modulator as variously described herein. In such method, the condition or disorder may comprise the use or abuse of one or more opioid drugs, e.g., fentanyl, morphine, oxycodone, hydrocodone, buprenorphine, heroin, and opioid derivatives of the foregoing. In the method broadly described above, the therapeutic benefit may comprise at least partial attenuation of opioid-induced hyperalgesia, e.g., wherein the opioid-induced hyperalgesia is induced by an opioid drug comprising at least one selected from the group consisting of fentanyl, morphine, oxycodone, hydrocodone, and buprenorphine.

The method broadly described above may be carried out, wherein the administering of a neuropeptide FF receptor modulator, constituted as variously described herein, is performed in a therapeutic intervention comprising coadministration of a drug for which the neuropeptide FF receptor modulator attenuates a side effect, e.g., wherein the drug for which the neuropeptide FF receptor modulator attenuates a side effect is a drug producing tolerance or hyperalgesia as the side effect.

The method broadly described above may be carried out in specific implementations, as further comprising administering an effective amount of a second therapeutically effective agent. Alternatively, the method broadly described above may be carried out in other specific implementations, wherein the condition or disorder where modulation of neuropeptide FF receptor activity is of therapeutic benefit is selected from the group consisting of attenuation of opioid tolerance and attenuation of hyperalgesia.

It therefore will be appreciated that the present disclosure contemplates a wide variety of compounds, neuropeptide FF receptor modulator agents, pharmaceutical and therapeutic compositions and formulations, and methods of making and using the foregoing.

Accordingly, while the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present disclosure, based on the description herein. Correspondingly, the subject matter as hereinafter claimed is intended to be broadly construed and interpreted, as including all such variations, modifications and alternative embodiments, within its spirit and scope.

What is claimed is:

1. A method for treating a subject to at least partially attenuate opioid tolerance or opioid-induced hyperalgesia, comprising administering to said subject a therapeutically effective amount of a neuropeptide FF receptor modulator comprising a compound selected from the group consisting of:

(2S,4S)-1-[(2-Chlorophenyl) methyl]-4-{[(4-methoxyphenyl) methyl] amino}-N-pentylpyrrolidine-2-carboxamide (16);

(2S,4S)-1-[(2-Chlorophenyl) methyl]-4-{[(4-methoxyphenyl) methyl] amino}-N-hexylpyrrolidine-2-carboxamide (18);

(2S,4S)—N-Benzyl-1-[(2-chlorophenyl) methyl]-4-{[(4-methoxyphenyl) methyl] amino} pyrrolidine-2-carboxamide (23);

(2S,4S)-1-[(2-Chlorophenyl) methyl]-4-{[(4-methoxyphenyl) methyl] amino}-N-(2-phenylethyl)-pyrrolidine-2-carboxamide (24);

(2S,4S)-1-[(2-Chlorophenyl) methyl]-N-[2-(4-methoxyphenyl) ethyl]-4-{[(4-methoxyphenyl)-methyl] amino} pyrrolidine-2-carboxamide (26);

(2S,4S)-1-[(2-Chlorophenyl) methyl]-N-[2-(4-methoxyphenyl) ethyl]-4-{[(4-nitrophenyl)-methyl|amino} pyrrolidine-2-carboxamide (33);

(2S,4S)-1-[(2-Chlorophenyl) methyl]-N-[2-(3.4-difluorophenyl) ethyl]-4-{[(4-methoxyphenyl)-methyl|amino} pyrrolidine-2-carboxamide (34);

(2S,4S)-1-[(2-Chlorophenyl) methyl]-4-{[(4-methoxyphenyl) methyl] amino}-N,N-dipropyl-pyrrolidine-2-carboxamide (41);

(2S,4S)-1-[(2-Chlorophenyl) methyl]-4-{[(4-(methylthio) phenyl) methyl|amino}-N-pentyl-pyrrolidine-2-carboxamide (44);

(2S,4S)-1-[(2-Chlorophenyl) methyl]-4-{[(4-(methylthio) phenyl) methyl] amino}-N-(2-phenyl-ethyl) pyrrolidine-2-carboxamide (45);

(2S,4S)-1-[(2-Chlorophenyl) methyl]-N-[2-(4-(methylthio) phenyl) ethyl]-4-{[(4-methoxyphenyl)-methylamino} pyrrolidine-2-carboxamide (46);

(2S,4S)-1-[(2-Chlorophenyl) methyl]-N-[2-(4-(methylthio) phenyl) ethyl]-4-{[(4-nitrophenyl)-methylamino} pyrrolidine-2-carboxamide (47);

(2S,4S)-1-[(2-Chlorophenyl) methyl]-N-[2-(3,4-difluorophenyl) ethyl]-4-{[] (4-(methylthio) phenyl)-methylamino} pyrrolidine-2-carboxamide (48);

(2S,4S)-1-[(2-Chlorophenyl) methyl]-4-{[(4-chlorophenyl) methyl] amino}-N-[2-(4-nitrophenyl)-ethyl|pyrrolidine-2-carboxamide (63);

(2S,4S)-1-[(3-Chlorophenyl) methyl]-4-{[(4-methoxyphenyl) methyl|amino}-N-(2-phenylethyl)-pyrrolidine-2-carboxamide (77); and (2S,4S)-4-{[(4-Methoxyphenyl) methyl]amino}-1-[(2-methylphenyl) methyl]-N-(2-phenylethyl)-pyrrolidine-2-carboxamide (82).

2. The method of claim 1, wherein the opioid tolerance or opioid-induced hyperalgesia is caused by use or abuse of one or more opioid drugs.

3. The method of claim 2, wherein the one or more opioid drugs comprises at least one selected from the group consisting of fentanyl, morphine, oxycodone, hydrocodone, buprenorphine, heroin, and opioid derivatives of the foregoing.

4. The method of claim 1, wherein said administering is performed in a therapeutic intervention comprising coadministration of a drug for which the neuropeptide FF receptor modulator attenuates a side effect.

5. The method of claim 4, wherein the drug produces tolerance or hyperalgesia as the side effect.

6. The method of claim 1, further comprising administering an effective amount of a second therapeutically effective agent.

7. The method of claim 6, wherein the second therapeutically effective agent is an opioid, an antipsychotic, or a monoamine reuptake inhibitor.

8. A method for treating opioid-induced hyperalgesia in a subject, comprising administering to the subject a therapeutically effective amount of (2S,4S)-1-[(2-chlorophenyl) methyl]-4-{[(4-methoxyphenyl) methyl] amino}-N-pentylpyrrolidine-2-carboxamide or (2S,4S)-1-[(2-chlorophenyl) methyl]-N-[2-(4-methoxyphenyl) ethyl]-4-{[(4-nitrophenyl) methyl] amino} pyrrolidine-2-carboxamide, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 12,390,446 B2 |
| APPLICATION NO. | : 18/484116 |
| DATED | : August 19, 2025 |
| INVENTOR(S) | : Yanan Zhang et al. |

It is certified that error appears in the above-identified patent and that said Letters Patent is hereby corrected as shown below:

In the Specification

Column 2, Line 17, "*Proc. Natd. Acad. Sci. USA*" should be -- *Proc. Natl. Acad. Sci. USA* --.

Column 39, Line 25, "5 m" should be -- 5 μm --.

Column 63, Line 49, "barner" should be -- barrier --.

Signed and Sealed this
Twenty-fifth Day of November, 2025

John A. Squires
*Director of the United States Patent and Trademark Office*